United States Patent
Zemel et al.

(10) Patent No.: US 9,943,517 B2
(45) Date of Patent: *Apr. 17, 2018

(54) COMPOSITIONS AND METHODS FOR INCREASING ENERGY METABOLISM

(71) Applicant: NuSirt Sciences, Inc., Nashville, TN (US)

(72) Inventors: Michael Zemel, Knoxville, TN (US); Antje Bruckbauer, Knoxville, TN (US); Brooke Baggett, Knoxville, TN (US)

(73) Assignee: NuSirt Sciences, Inc., Nashville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/442,711

(22) PCT Filed: Nov. 13, 2013

(86) PCT No.: PCT/US2013/069957
§ 371 (c)(1),
(2) Date: May 13, 2015

(87) PCT Pub. No.: WO2014/078459
PCT Pub. Date: May 22, 2014

(65) Prior Publication Data
US 2016/0279130 A1    Sep. 29, 2016

Related U.S. Application Data

(60) Provisional application No. 61/726,006, filed on Nov. 13, 2012.

(51) Int. Cl.
| | | |
|---|---|---|
| *A61K 31/519* | (2006.01) | |
| *A61K 31/198* | (2006.01) | |
| *A61K 31/05* | (2006.01) | |
| *A61K 31/675* | (2006.01) | |
| *A61K 31/7048* | (2006.01) | |
| *A61K 31/19* | (2006.01) | |
| *A61K 9/00* | (2006.01) | |
| *A61K 45/06* | (2006.01) | |
| *A61K 31/4415* | (2006.01) | |

(52) U.S. Cl.
CPC .......... *A61K 31/519* (2013.01); *A61K 9/0053* (2013.01); *A61K 31/05* (2013.01); *A61K 31/19* (2013.01); *A61K 31/198* (2013.01); *A61K 31/4415* (2013.01); *A61K 31/675* (2013.01); *A61K 31/7048* (2013.01); *A61K 45/06* (2013.01)

(58) Field of Classification Search
CPC .............. A61K 31/519; A61K 31/7048; A61K 31/198; A61K 31/19; A61K 31/05; A61K 31/675; A61K 9/0053; A61K 2300/00
USPC .......................................................... 514/27
See application file for complete search history.

(56) References Cited

U.S. PATENT DOCUMENTS

| | | |
|---|---|---|
| 3,810,994 A | 5/1974 | Wiegand |
| 3,936,527 A | 2/1976 | Alper |
| 4,606,909 A | 8/1986 | Bechgaard et al. |
| 4,769,027 A | 9/1988 | Baker et al. |
| 4,803,080 A | 2/1989 | Benedikt et al. |
| 4,897,268 A | 1/1990 | Tice et al. |
| 4,992,470 A | 2/1991 | Nissen |
| 5,069,204 A | 12/1991 | Smith et al. |
| 5,087,624 A | 2/1992 | Boynton et al. |
| 5,250,534 A | 10/1993 | Bell et al. |
| 5,339,771 A | 8/1994 | Axelrod |
| 5,395,626 A | 3/1995 | Kotwal et al. |
| 5,419,283 A | 5/1995 | Leo |
| 5,616,569 A | 4/1997 | Reinhart |
| 5,776,913 A | 7/1998 | Ogilvie et al. |
| 5,886,012 A | 3/1999 | Pang et al. |
| 5,968,569 A | 10/1999 | Cavadini et al. |
| 6,004,996 A | 12/1999 | Shah et al. |
| 6,031,000 A | 2/2000 | Nissen et al. |
| 6,048,903 A | 4/2000 | Toppo |
| 6,063,414 A | 5/2000 | Jones et al. |
| 6,063,820 A | 5/2000 | Cavazza |
| 6,224,861 B1 | 5/2001 | Abe et al. |
| 6,280,779 B1 | 8/2001 | Nadeau et al. |
| 6,338,862 B1 | 1/2002 | Niazi |
| 6,369,042 B1 | 4/2002 | Oberthur et al. |
| 6,384,087 B1 | 5/2002 | Zemel et al. |
| 6,387,419 B1 | 5/2002 | Christensen |

(Continued)

FOREIGN PATENT DOCUMENTS

| | | |
|---|---|---|
| CN | 1504424 A | 6/2004 |
| CN | 102077936 A | 6/2011 |

(Continued)

OTHER PUBLICATIONS

European search report and opinion dated Sep. 28, 2015 for EP Application No. 13758140.1.
Notice of allowance dated Sep. 1, 2015 for U.S. Appl. No. 13/662,345.
Notice of allowance dated Sep. 11, 2015 for U.S. Appl. No. 14/746,516.
U.S. Appl. No. 15/164,647, filed May 25, 2016, Zemel et al.

(Continued)

*Primary Examiner* — Yih-Horng Shiao
(74) *Attorney, Agent, or Firm* — Wilson Sonsini Goodrich & Rosati

(57) ABSTRACT

Compositions and methods useful for inducing an increase in fatty acid oxidation or mitochondrial biogenesis, reducing weight gain, inducing weight loss, or increasing Sirt1, Sirt3, or AMPK activity are provided herein. Such compositions comprise a combination of a PDE 5 inhibitor, such as sildenafil or icariin, and resveratrol, and a branched amino acid such as leucine, or its metabolite.

21 Claims, 16 Drawing Sheets

(56) References Cited

U.S. PATENT DOCUMENTS

| | | | |
|---|---|---|---|
| 6,426,091 B1 | 7/2002 | Okumura et al. | |
| 6,469,012 B1 | 10/2002 | Ellis et al. | |
| 6,517,877 B2 | 2/2003 | Gannon | |
| 6,527,711 B1 | 3/2003 | Stivoric et al. | |
| 6,595,929 B2 | 7/2003 | Stivoric et al. | |
| 6,605,038 B1 | 8/2003 | Teller et al. | |
| 6,635,268 B2 | 10/2003 | Peery et al. | |
| 6,638,545 B1 | 10/2003 | Rombi | |
| 6,676,967 B1 | 1/2004 | Cefali et al. | |
| 6,764,697 B1 | 7/2004 | Jao et al. | |
| 6,790,869 B2 | 9/2004 | Ghai et al. | |
| 6,797,283 B1 | 9/2004 | Edgren et al. | |
| 6,919,373 B1 | 7/2005 | Lam et al. | |
| 6,923,800 B2 | 8/2005 | Chen et al. | |
| 6,929,803 B2 | 8/2005 | Wong et al. | |
| 6,939,556 B2 | 9/2005 | Lautenbach | |
| 7,020,508 B2 | 3/2006 | Stivoric et al. | |
| 7,109,198 B2 | 9/2006 | Gadde et al. | |
| 7,141,254 B2 | 11/2006 | Bhaskaran et al. | |
| 7,153,262 B2 | 12/2006 | Stivoric et al. | |
| 7,230,009 B2 | 6/2007 | Haque et al. | |
| 7,261,690 B2 | 8/2007 | Teller et al. | |
| 7,285,090 B2 | 10/2007 | Stivoric et al. | |
| 7,354,738 B2 | 4/2008 | Spielgelman et al. | |
| 7,495,101 B2 | 2/2009 | Fischesser et al. | |
| 7,502,643 B2 | 3/2009 | Farringdon et al. | |
| 7,674,485 B2 | 3/2010 | Bhaskaran et al. | |
| 7,689,437 B1 | 3/2010 | Teller et al. | |
| 7,722,905 B2 | 5/2010 | Khoo | |
| 7,744,930 B2 | 6/2010 | Fisher et al. | |
| 7,829,556 B2 | 11/2010 | Bemis et al. | |
| 7,855,289 B2 | 12/2010 | Nunes et al. | |
| 7,870,856 B2 | 1/2011 | Boeck | |
| 7,893,086 B2 | 2/2011 | Bemis et al. | |
| 7,959,567 B2 | 6/2011 | Stivoric et al. | |
| 7,989,007 B2 | 8/2011 | Giuliano et al. | |
| 8,008,458 B2 | 8/2011 | Zaloga et al. | |
| 8,017,634 B2 | 9/2011 | Sinclair et al. | |
| 8,044,198 B2 | 10/2011 | Nunes et al. | |
| 8,073,707 B2 | 12/2011 | Teller et al. | |
| 8,088,043 B2 | 1/2012 | Andren et al. | |
| 8,088,044 B2 | 1/2012 | Tchao et al. | |
| 8,088,928 B2 | 1/2012 | Nunes et al. | |
| 8,093,401 B2 | 1/2012 | Nunes et al. | |
| 8,106,097 B2 | 1/2012 | Najib | |
| 8,157,731 B2 | 4/2012 | Teller et al. | |
| 8,192,767 B2 | 6/2012 | Carta | |
| 8,275,635 B2 | 9/2012 | Stivoric et al. | |
| 8,299,083 B2 | 10/2012 | Kass et al. | |
| 8,369,936 B2 | 2/2013 | Farringdon et al. | |
| 8,370,549 B2 | 2/2013 | Burton et al. | |
| 8,378,090 B2 | 2/2013 | Petiard et al. | |
| 8,382,590 B2 | 2/2013 | Stivoric et al. | |
| 8,398,546 B2 | 3/2013 | Pacione et al. | |
| 8,403,845 B2 | 3/2013 | Stivoric et al. | |
| 8,408,436 B2 | 4/2013 | Berry et al. | |
| 8,469,862 B2 | 6/2013 | Andren et al. | |
| 8,517,896 B2 | 8/2013 | Robinette et al. | |
| 8,557,869 B2 | 10/2013 | Yamka et al. | |
| 8,562,489 B2 | 10/2013 | Burton et al. | |
| 8,597,677 B2 | 12/2013 | Yamka et al. | |
| 8,617,886 B2 | 12/2013 | Zemel et al. | |
| 8,623,924 B2 | 1/2014 | Zemel et al. | |
| 9,072,692 B2 | 7/2015 | Zemel et al. | |
| 9,198,454 B2 | 12/2015 | Zemel et al. | |
| 9,198,883 B1 | 12/2015 | Zemel et al. | |
| 9,351,967 B2 | 5/2016 | Zemel et al. | |
| 9,408,410 B2 | 8/2016 | Zemel et al. | |
| 9,408,834 B2 | 8/2016 | Zemel et al. | |
| 9,585,876 B2 | 3/2017 | Zemel et al. | |
| 9,682,053 B2 | 6/2017 | Zemel et al. | |
| 9,707,213 B2 | 7/2017 | Zemel et al. | |
| 2001/0043983 A1 | 11/2001 | Hamilton | |
| 2003/0035882 A1 | 2/2003 | McDaniel et al. | |
| 2003/0166662 A1* | 9/2003 | Fryburg | A61K 31/505 514/252.16 |
| 2003/0187055 A1 | 10/2003 | Riker et al. | |
| 2004/0028751 A1 | 2/2004 | Mae et al. | |
| 2004/0120983 A1 | 6/2004 | Connolly | |
| 2004/0186046 A1 | 9/2004 | Burgess et al. | |
| 2005/0042362 A1 | 2/2005 | Clark et al. | |
| 2005/0064070 A1 | 3/2005 | Liebrecht | |
| 2005/0100617 A1 | 5/2005 | Malnoe et al. | |
| 2005/0181097 A1 | 8/2005 | Townsend et al. | |
| 2005/0215882 A1 | 9/2005 | Chenevert et al. | |
| 2006/0051416 A1 | 3/2006 | Rastogi et al. | |
| 2006/0111435 A1 | 5/2006 | Sinclair et al. | |
| 2006/0159746 A1 | 7/2006 | Troup et al. | |
| 2006/0165824 A1 | 7/2006 | Khambe | |
| 2006/0188611 A1 | 8/2006 | Unlu et al. | |
| 2006/0194743 A1 | 8/2006 | Oku et al. | |
| 2006/0205633 A1 | 9/2006 | Nishitani et al. | |
| 2007/0014833 A1 | 1/2007 | Milburn et al. | |
| 2007/0065512 A1 | 3/2007 | Dedhiya et al. | |
| 2007/0077310 A1 | 4/2007 | Zemel et al. | |
| 2007/0092577 A1 | 4/2007 | Zemel et al. | |
| 2007/0110850 A1 | 5/2007 | Rifkin | |
| 2007/0190171 A1 | 8/2007 | Yamka et al. | |
| 2007/0203083 A1 | 8/2007 | Mootha et al. | |
| 2007/0244202 A1 | 10/2007 | Murase | |
| 2007/0286909 A1 | 12/2007 | Smith et al. | |
| 2008/0069862 A1 | 3/2008 | Hurwitz | |
| 2008/0076828 A1 | 3/2008 | Dalton et al. | |
| 2008/0102137 A1 | 5/2008 | Guffey | |
| 2008/0176822 A1 | 7/2008 | Chen | |
| 2008/0220092 A1 | 9/2008 | Dipierro et al. | |
| 2008/0233245 A1 | 9/2008 | White et al. | |
| 2008/0242727 A1* | 10/2008 | Romero | A61K 31/164 514/561 |
| 2008/0268038 A1 | 10/2008 | Wolfe | |
| 2008/0286254 A1 | 11/2008 | Sakamoto et al. | |
| 2009/0012183 A1 | 1/2009 | Draijer et al. | |
| 2009/0017130 A1 | 1/2009 | Yamka et al. | |
| 2009/0054450 A1 | 2/2009 | Currie | |
| 2009/0074827 A1 | 3/2009 | Scherl et al. | |
| 2009/0105246 A1 | 4/2009 | Bemis et al. | |
| 2009/0142336 A1 | 6/2009 | Walsh et al. | |
| 2009/0156648 A1 | 6/2009 | Molino et al. | |
| 2009/0163476 A1 | 6/2009 | Milburn et al. | |
| 2009/0182036 A1 | 7/2009 | Krammer-Lukas | |
| 2009/0197820 A1 | 8/2009 | Wolfe et al. | |
| 2009/0230013 A1 | 9/2009 | Born et al. | |
| 2010/0009992 A1 | 1/2010 | Bimberg et al. | |
| 2010/0130597 A1* | 5/2010 | Chung | A61K 45/06 514/44 R |
| 2010/0158956 A1 | 6/2010 | Komorowski | |
| 2010/0173024 A1 | 7/2010 | McDaniel | |
| 2010/0204204 A1 | 8/2010 | Zaworotko et al. | |
| 2010/0210692 A1 | 8/2010 | Farmer et al. | |
| 2010/0261793 A1 | 10/2010 | Caterson et al. | |
| 2010/0303966 A1 | 12/2010 | Sunvold et al. | |
| 2010/0303967 A1 | 12/2010 | Sunvold et al. | |
| 2010/0304003 A1 | 12/2010 | Friesen et al. | |
| 2010/0316679 A1 | 12/2010 | Sinclair et al. | |
| 2010/0324002 A1 | 12/2010 | Fox et al. | |
| 2011/0020443 A1 | 1/2011 | Liu et al. | |
| 2011/0027416 A1 | 2/2011 | Sunvold et al. | |
| 2011/0033559 A1 | 2/2011 | Zemel et al. | |
| 2011/0038948 A1 | 2/2011 | Zemel et al. | |
| 2011/0064712 A1 | 3/2011 | Amato | |
| 2011/0064720 A1 | 3/2011 | Amato | |
| 2011/0070258 A1 | 3/2011 | Jimenez Del et al. | |
| 2011/0082189 A1 | 4/2011 | Sinclair et al. | |
| 2011/0111066 A1 | 5/2011 | Ferguson et al. | |
| 2011/0112047 A1 | 5/2011 | Evans et al. | |
| 2011/0130387 A1 | 6/2011 | Nunes et al. | |
| 2011/0165125 A1 | 7/2011 | Pan | |
| 2011/0208153 A1 | 8/2011 | Alvey | |
| 2012/0035105 A1 | 2/2012 | Geho et al. | |
| 2012/0058088 A1 | 3/2012 | Sardi | |
| 2012/0129785 A1 | 5/2012 | Fleuranges et al. | |
| 2012/0177730 A1 | 7/2012 | Baron et al. | |
| 2012/0225139 A1 | 9/2012 | Ferguson et al. | |

(56) References Cited

U.S. PATENT DOCUMENTS

| | | |
|---|---|---|
| 2012/0289598 A1 | 11/2012 | Yamka et al. |
| 2012/0301559 A1 | 11/2012 | Pridmore-Merten et al. |
| 2013/0017283 A1 | 1/2013 | Zemel et al. |
| 2013/0017284 A1 | 1/2013 | Zemel et al. |
| 2013/0045193 A1 | 2/2013 | Gonzalez et al. |
| 2013/0052286 A1 | 2/2013 | Wada et al. |
| 2013/0151196 A1 | 6/2013 | Yuen et al. |
| 2013/0158369 A1 | 6/2013 | Yuen et al. |
| 2013/0237605 A1 | 9/2013 | Zemel et al. |
| 2013/0323287 A1 | 12/2013 | Komorowski |
| 2014/0057017 A1 | 2/2014 | Yamka et al. |
| 2014/0148488 A1 | 5/2014 | Zemel et al. |
| 2015/0056274 A1 | 2/2015 | Zemel et al. |
| 2016/0000737 A1 | 1/2016 | Zemel et al. |
| 2016/0008329 A1 | 1/2016 | Zemel et al. |
| 2016/0067201 A1 | 3/2016 | Zemel et al. |
| 2016/0279130 A1 | 9/2016 | Zemel et al. |
| 2017/0000780 A1 | 1/2017 | Zemel et al. |
| 2017/0065545 A1 | 3/2017 | Zemel et al. |
| 2017/0239253 A1 | 8/2017 | Zemel et al. |
| 2017/0312240 A1 | 11/2017 | Zemel et al. |

FOREIGN PATENT DOCUMENTS

| | | |
|---|---|---|
| EP | 1685833 A1 | 8/2006 |
| EP | 1818055 A1 | 8/2007 |
| EP | 2308493 A1 | 7/2009 |
| FR | 2710243 A1 | 3/1995 |
| GB | 1584539 A | 2/1981 |
| JP | 3219838 B2 | 10/1995 |
| JP | 2002047699 A | 2/2002 |
| JP | 2005097273 A | 4/2005 |
| JP | 2007306851 A | 11/2007 |
| JP | 2008-063321 A | 3/2008 |
| JP | 2008-063328 A | 3/2008 |
| JP | 2008535520 A | 9/2008 |
| JP | 2011097951 A | 5/2011 |
| JP | 2011130774 A | 7/2011 |
| JP | 2011528557 A | 11/2011 |
| JP | 2012509669 A | 4/2012 |
| JP | 2012527894 A | 11/2012 |
| JP | 2013500011 A | 1/2013 |
| WO | WO-2004056208 A1 | 7/2004 |
| WO | WO 2004/082401 A1 | 9/2004 |
| WO | WO-2005049006 A1 | 6/2005 |
| WO | WO-2005065667 A2 | 7/2005 |
| WO | WO-2006013750 A1 | 2/2006 |
| WO | WO-2006110406 A2 | 10/2006 |
| WO | WO-2007146124 A2 | 12/2007 |
| WO | WO-2007146313 A1 | 12/2007 |
| WO | WO 2011/051974 A1 | 5/2011 |
| WO | WO 2012/097064 A1 | 7/2012 |
| WO | WO-2013012760 A1 | 1/2013 |
| WO | WO-2013028547 A1 | 2/2013 |
| WO | WO-2013134736 A1 | 9/2013 |
| WO | WO-2013169007 A1 | 11/2013 |
| WO | WO-2014078459 A1 | 5/2014 |
| WO | WO-2014113404 A1 | 7/2014 |
| WO | WO-2014152016 A1 | 9/2014 |
| WO | WO-2015053379 A1 | 4/2015 |
| WO | WO-2017040407 A1 | 3/2017 |

OTHER PUBLICATIONS

European search report and opinion dated May 6, 2016 for EP Application No. 13854549.

Varma, et al. Chronic Tadalafil Therapy Improves Fasting Glucose Levels and Downregulates Micronna-103 and -107 in Obese Diabetic Mice. Circulation 2012; 126: A14802. Abstract 14802.

Bannowsky, A. et al., Recovery of erectile function after nerve-sparing radical prostatectomy: improvement with nightly low-dose sildenafil. BJU Int., Feb. 18, 2008, vol. 101, No. 10, pp. 1279-1283.

International Search report and Written opinion dated Sep. 19, 2016 for Singapore Application No. 11201503774P.

Shalwala, M. B., A novel role of sirt1 in sildenafil induced cardio protection in mice. Virginia Commonwealth University—Master Thesis, May 2010, pp. 1-56.

U.S. Appl. No. 15/206,183, filed Jul. 8, 2016, Zemel et al.

Bender, et al. Cyclic nucleotide phosphodiesterases: molecular regulation to clinical use. Pharmacol Rev. Sep. 2006;58(3):488-520.

Bruckbauer, et al. Synergistic effects of polyphenols and methylxanthines with leucine on AMPK/sirtuin-mediated metabolism in muscle cells and adipocytes. PLoS One. 9(2):e89166. Feb. 14, 2014.

Chalasani, et al. The diagnosis and management of non-alcoholic fatty liver disease: Practice guideline by the American Association for the Study of Liver Diseases, American College of Gastroenterology, and the American Gastroenterological Association Hepatology 2012; 55:2005-2021.

Festi, et al. Hepatic steastosis in obese patients: clinical aspects and prognostic significance. Obesity Rev 2004; 5:27-42.

Hou, et al. Sirt1 regulates hepatocyte lipid metabolism through activating AMPK-activated protein kinase. J Biol Chem 2008; 383:20015-20026.

International search report and written opinion dated May 22, 2015 for PCT/US2015/018182.

Purushotham, et al. Hepatocyte-specific deletion of Sirt1 alters fatty acid metabolism and results in hepatic steatosis and inflammation Cell Metabolism 2009; 9:327-338.

Vernon et al. Systematic review: The epidemiology and natural history of non-alcoholic fatty liver disease and non-alcoholic steatohepatitis in adults. Aliment Pharmacol 2011; 34:274-285.

Zoraghi, et al. Phosphodiesterase-5 Gln817 is critical for cGMP, vardenafil, or sildenafil affinity: its orientation impacts cGMP but not cAMP affinity. J Biol Chem. Mar. 3, 2006;281(9):5553-8. Epub Jan. 5, 2006.

U.S. Appl. No. 14/927,228, filed Oct. 29, 2015, Zemel et al.

U.S. Appl. No. 14/927,255, filed Oct. 29, 2015, Zemel et al.

U.S. Appl. No. 14/746,516, filed Jun. 22, 2015, Zemel et al.

Agarwal. Cortisol metabolism and visceral obesity: role of 11beta-hydroxysteroid dehydrogenase type I enzyme and reduced co-factor NADPH. Endocr Res. Nov. 2003;29(4):411-8.

Alwine, et al. Method for detection of specific RNAs in agarose gels by transfer to diazobenzyloxymethyl-paper and hybridization with DNA probes. Proc Natl Acad Sci U S A. Dec. 1977;74(12):5350-4.

Amstad, et al. Mechanism of c-fos induction by active oxygen. Cancer Res. Jul. 15, 1992;52(14):3952-60.

Anthony, et al. Orally Administered Leucine Stimulates Protein Synthesis of Skeletal Muscle of Postabsorptive Rats in Association with Increased eIF4F Formation1'2. The Journal of Nutrition. 2000; 130:139-145.

Argiles, et al. Cross-talk between skeletal muscle and adipose tissue: a link with obesity? Med Res Rev. Jan. 2005;25(1):49-65.

Atabek, et al. al. Oxidative stress in childhood obesity. J Pediatr Endocrinol Metab. Aug. 2004;17(8):1063-8.

Ayala, et al. Chronic treatment with sildenafil improves energy balance and insulin action in high fat-fed conscious mice. Diabetes. Apr. 2007;56(4):1025-33. Epub Jan. 17, 2007.

Banakar, et al. 1alpha, 25-dihydroxyvitamin D3 prevents DNA damage and restores antioxidant enzymes in rat hepatocarcinogenesis induced by diethylnitrosamine and promoted by phenobarbital. World J Gastroenterol. May 1, 2004;10(9):1268-75.

Berchtold. A simple method for direct cloning and sequencing cDNA by the use of a single specific oligonucleotide and oligo(dT) in a polymerase chain reaction (PCR). Nucleic Acids Res. Jan. 11, 1989;17(1):453.

Beta-hydroxy Beta-methylbutyrate (Hmb). 2009; 1-2. http://exrx.net/Nutrition/Supplements/HMB.html.

Black grape ingredients. Power of resveratrol. Accessed: Sep. 29, 2010. www.blackgrapehealth.com/Tnt37/ingredients.php.

Blum, et al. SIRT1 modulation as a novel approach to the treatment of diseases of aging J Med Chem. Jan. 27, 2011;54(2):417-32. Epub Nov. 16, 2010.

BodyBuilding, VitaMinder Power shaker, 2006, BodyBuilding.com, p. 1.

(56) References Cited

OTHER PUBLICATIONS

Bostrum, et al. A PGC1-α-dependent myokine that drives brown-fat-like development of white fat and thermogenesis. Nature. Jan. 11, 2012;481(7382):463-8. doi: 10.1038/nature10777.
Botanical Online 2010, 1-3. httpll:www.botanical-online.com/english/plantschemicalagents.htm.
Boustany. Diabetes and grapefruit. 2010. ThinkScienceNow. 1-4. http://www.thinksciencenow.com/blog-post/diabetes-and-grapefruit/.
Brand, et al. Mitochondrial superoxide and aging: uncoupling-protein activity and superoxide production. Biochem Soc Symp. 2004;(71):203-13.
Breastfeeding.com. Q&A How many ounces of breast milk should I pump? 2010; 1-2. http://www.breastfeeding.com/breastfeeding-questions/breastfeeding-pumping-basics/qa/how-many-ounces-of-breast-milk-should-i-pumpp.aspx.
Brookes. Mitochondrial H(+) leak and ROS generation: an odd couple. Free Radic Biol Med. Jan. 1, 2005;38(1):12-23.
Bruckbauer, et al. Synergistic effects of leucine and resveratrol on insulin sensitivity and fat metabolism in adipocytes and mice. Nutr Metab (Land). Aug. 22, 2012;9(1):77. doi: 10.1186/1743-7075-9-77.
Bruckbauer, et al. Synergistic effects of metformin, resveratrol, and hydroxymethylbutyrate on insulin sensitivity. Diabetes Metab Syndr Obes. 2013;6:93-102. doi: 10.2147/DMSO.S40840. Epub Feb. 13, 2013.
Bruckbauer, et al. The effects of dairy components on energy partitioning and metabolic risk in mice: a microarray study. J Nutrigenet Nutrigenomics. 2009;2(2):64-77. Epub Mar. 4, 2009.
Busquets, et al. Interleukin-15 decreases proteolysis in skeletal muscle: a direct effect. Int J Mol Med. Sep. 2005;16(3):471-6.
Carbo, et al. Interleukin-15 antagonizes muscle protein waste in tumour-bearing rats. Br J Cancer. Aug. 2000;83(4):526-31.
Carbo, et al. Interleukin-15 mediates reciprocal regulation of adipose and muscle mass: a potential role in body weight control. Biochim Biophys Acta. Apr. 3, 2001;1526(1):17-24.
Cerutti, et al. The role of the cellular antioxidant defense in oxidant carcinogenesis. Environ Health Perspect. Dec. 1994;102 Suppl 10:123-9.
Chang, et al. Mammalian MAP kinase signalling cascades. Nature. Mar. 1, 2001;410(6824):37-40.
Cheng, et al. Leucine deprivation decreases fat mass by stimulation of lipolysis in white adipose tissue and upregulation of uncoupling protein 1 (UCP1) in brown adipose tissue. Diabetes. Jan. 2010;59(1):17-25. Epub Oct. 15, 2009.
Chung, et al. Contribution of polyol pathway to diabetes-induced oxidative stress. J Am Soc Nephrol. Aug. 2003;14(8 Suppl 3):S233-6.
Clement, et al. Weight loss regulates inflammation-related genes in white adipose tissue of obese subjects. FASEB J. Nov. 2004;18(14):1657-69.
Cottam, et al. The chronic inflammatory hypothesis for the morbidity associated with morbid obesity: implications and effects of weight loss. Obes Surg. May 2004;14(5):589-600.
De Souza, et al. Insulin secretory defect in zucker FA/FA rats is improved by ameliorating insulin resistance. Diabetes. Aug. 1995;44(8):984-91.
Ding, et al. Amino acid composition of lactating mothers' milk and confinement diet in rural North China. Asia Pac J. Clin Nutr. 2010; 19(3):344-349.
Doi, et al. Isoleucine, a Blood Glucose-Lowering Amino Acid, Increases Glucose Uptake in Rat Skeletal Muscle in the Absence of Increases in AMP-Activated Protein Kinase Activity. J Nutr. Sep. 2005;135(9):2103-8.
Donato, et al. Effects of leucine supplementation on the body composition and protein status of rats submitted to food restriction. Nutrition. May 2006;22(5):520-7.
Duval, et al. Increased reactive oxygen species production with antisense oligonucleotides directed against uncoupling protein 2 in murine endothelial cells. Biochem Cell Biol. 2002;80(6):757-64.

Emerging risk factors collaboration. Diabetes mellitus, fasting glucose, and risk of cause-specific death. N Engl J Med. Mar. 3, 2012;364(9):829-41.
Erlanson-Albertsson. The role of uncoupling proteins in the regulation of metabolism. Acta Physiol Scand. Aug. 2003;178(4):405-12.
Ermak, et al. Calcium and oxidative stress: from cell signaling to cell death. Mol. Immunol. Feb. 2002;38(10):713-21.
European search report and opinion dated Mar. 9, 2015 for EP Application No. 12814141.3.
Fain, et al. Comparison of the release of adipokines by adipose tissue, adipose tissue matrix, and adipocytes from visceral and subcutaneous abdominal adipose tissues of obese humans. Endocrinology. May 2004;145(5):2273-82. Epub Jan. 15, 2004.
Feige, et al. Specific SIRT1 activation mimics low energy levels and protects against diet-induced metabolic disorders by enhancing fat oxidation. Supplemental information. Cell Metab. Nov. 2008;8(5):347-58.
Feige, et al. Specific SIRT1 activation mimics low energy levels and protects against diet-induced metabolic disorders by enhancing fat oxidation. Cell Metab. Nov. 2008;8(5):347-58. Erratum Cell Metab. Feb. 2009;9(2):210.
Flatt, et al. Direct and indirect actions of nutrients in the regulation of insulin secretion from the pancreatic beta cells. Proc Nutr Soc. Dec. 1991;50(3):559-66.
Fortamet (Metaformin Hydrochloride) Extended-Release Tablets Label. http://www.accessdata.fda.gov/drugsatfda_docs/label/2008/021574s010lb1.pdf Accessed Jul. 6, 2015.
Fried, et al. Omental and subcutaneous adipose tissues of obese subjects release interleukin-6: depot difference and regulation by glucocorticoid. J Clin Endocrinol Metab. Mar. 1998;83(3):847-50.
Furukawa, et al. Increased oxidative stress in obesity and its impact on metabolic syndrome. J Clin Invest. Dec. 2004;114(12):1752-61.
Gerlinger-Romero, et al. Chronic supplementation of beta-hydroxy-beta methylbutyrate (HMβ) increases the activity of the GH/IGF-I axis and induces hyperinsulinemia in rats. Growth Horm IGF Res. Apr. 2011;21(2):57-62. doi: 10.1016/j.ghir.2010.12.006. Epub Jan. 14, 2011.
Girl et al. Constitutive activation of NF-kappaB causes resistance to apoptosis in human cutaneous T cell lymphoma HuT-78 cells. Autocrine role of tumor necrosis factor and reactive oxygen intermediates. J Biol Chem. May 29, 1998;273(22):14008-14.
Goldman, et al. Generation of reactive oxygen species in a human keratinocyte cell line: role of calcium. Arch Biochem Biophys. Feb. 1, 1998;350(1):10-8.
Goldstein, et al. Adiponectin: A novel adipokine linking adipocytes and vascular function. J Clin Endocrinol Metab. Jun. 2004;89(6):2563-8.
Gordeeva, et al. Cross-talk between reactive oxygen species and calcium in living cells. Biochemistry (Most). Oct. 2003;68(10):1077-80.
Hale, et al. Transfer of metforimin into human milk. Diabetologia. 2002; 45:1509-1514.
Harwood, et al. Isozyme-nonselective N-Substituted Bipiperidylcarboxamide Acetyl-CoA Carboxylase Inhibitors Reduce Tissue Malonyl-CoA Concentrations, Inhibit Fatty Acid Synthesis, and Increase Fatty Acid Oxidation in Cultured Cells and in Experimental Animals. The Journal of Biological Chemistry. Sep. 26, 2003; 278(39):37099-37111.
Hollander, et al. Induction of fos RNA by DNA-damaging agents. Cancer Res. Apr. 1, 1989;49(7):1687-92.
Hotamisligil, et al. Tumor necrosis factor alpha inhibits signaling from the insulin receptor. Proc Natl Acad Sci U S A. May 24, 1994;91(11):4854-8.
Howells, et al. Phase I randomized, double-blind pilot study of micronized resveratrol (SRT501) in patients with hepatic metastases—safety, pharmacokinetics, and pharmacodynamics. Cancer Prev Res (Phila). Sep. 2011;4(9):1419-25. Epub Jun. 16, 2011.
Hydroxymethyl Butyrate (HMB). Beth Israel Deaconess Medical Center. Accessed Dec. 13, 2012. http://www.bidmc.org/YourHealth/HolisticHealth/HerbsandSupplements.aspx?ChunkID=21551.
Inoguchi, et al. High glucose level and free fatty acid stimulate reactive oxygen species production through protein kinase C-de-

(56) References Cited

OTHER PUBLICATIONS pendent activation of NAD(P)H oxidase in cultured vascular cells. Diabetes. Nov. 2000;49(11):1939-45.
International search report and written opinion dated May 28, 2013 for PCT Application No. US2013/030044.
International search report and written opinion dated Feb. 8, 2007 for PCT Application No. US2006/038854.
International search report and written opinion dated Mar. 10, 2014 for PCT Application No. US2013/069957.
International search report and written opinion dated Nov. 29, 2012 for PCT Application No. US2012/046814.
JillWillRun. Hydration Review Nuun, 2009, pp. 1-8.
Khan, et al. Induction of renal oxidative stress and cell proliferation response by ferric nitrilotriacetate (Fe-NTA): diminution by soy isoflavones. Chem Biol Interact. Aug. 10, 2004;149(1):23-35.
Kiens. Skeletal Muscle Lipid Metabolism in Exercise and Insulin Resistance. Physiological Reviews. 2006;86: 205-243.
Koren, et al. Vitamin D is a prooxidant in breast cancer cells. Cancer Res. Feb. 15, 2001;61(4): 1439-44.
Korshunov, et al. High protonic potential actuates a mechanism of production of reactive oxygen species in mitochondria. FEBS Lett. Oct. 13, 1997;416(1):15-8.
Kouzarides, et al. Leucine zippers of fos, jun and GCN4 dictate dimerization specificity and thereby control DNA binding. Nature. Aug. 17, 1989;340(6234):568-71.
Krishnaswamy, et al. Effect of vitamin B6 on leucine-induced changes in human subjects. Am J Clin Nutr. Feb. 1976;29(2):177-81.
Layman. The role of leucine in weight loss diets and glucose homeostasis. Journal of Nutrition, 2003, 133, 261S-267S.
Lee, et al. The evolving role of inflammation in obesity and the metabolic syndrome Curr Diab Rep. Feb. 2005;5(1):70-5.
Leenders, et al. Leucine as a pharmaconutrient to prevent and treat sarcopenia and type 2 diabetes. Nutr Rev. Nov. 2011;69(11):675-89. doi: 10.1111/j.1753-4887.2011.00443.x. Abstract only.
Li, et al. Evaluation of antioxidant capacity and aroma quality of breast milk. Nutrition. 2008; 25(1):1-3.
Li, et al. Leucine nutrition in animals and humans: mTOR signaling and beyond. Amino Acids. Nov. 2011;41(5):1185-93. Epub Jul. 20, 2011.
Li, et al. Visceral fat: higher responsiveness of fat mass and gene expression to calorie restriction than subcutaneous fat. Exp Biol Med (Maywood). Nov. 2003;228(10):1118-23.
Lin, et al. Increased oxidative damage with altered antioxidative status in type 2 diabetic patients harboring the 16189 T to C variant of mitochondrial DNA. Ann N Y Acad Sci. May 2005;1042:64-9.
Lin. Suppression of protein kinase C and nuclear oncogene expression as possible action mechanisms of cancer chemoprevention by Curcumin. Arch Pharm Res. Jul. 2004;27(7):683-92.
Lind, et al. Evaluation of four different methods to measure endothelium-dependent vasodilation in the human peripheral circulation. Clin Sci (Lond). May 2002;102(5):561-7.
Lira, et al. Nitric oxide and AMPK cooperatively regulate PGC-1 in skeletal muscle cells. J Physiol. Sep. 15, 2010;588(Pt 18):3551-66. Epub Jul. 19, 2010.
Lumeng, et al. Plasma content of B6 vitamers and its relationship to hepatic vitamin B6 metabolism. J Clin Invest. Oct. 1980; 66(4): 688-695.
Lynch, et al. Leucine is a direct-acting nutrient signal that regulates protein synthesis in adipose tissue. Am J Physiol Endocrinol Metab. Sep. 2002;283(3):E503-13.
Macotela, et al. Dietary Leucine—an environmental modifier of insulin resistance acting on multiple levels of metabolism. PLoS One. 2011;6(6):e21187. Epub Jun. 22, 2011.
Mahadev, et al. The NAD(P)H oxidase homolog Nox4 modulates insulin-stimulated generation of H2O2 and plays an integral role in insulin signal transduction. Mol Cell Biol. Mar. 2004;24(5):1844-54.
Manders, et al. Nutrition and disease co-ingestion of a protein hydrolysate with or without additional leucine effectively reduces postprandial blood glucose excursions in type 2 diabetic men 1. Jan. 1, 2006. 1294-1299. http://jn.nutrition.org/content/136/5/1294.full.pdf.
Manea, et al. Changes in oxidative balance in rat pericytes exposed to diabetic conditions. J Cell Mol Med. Jan.-Mar. 2004;8(1):117-26.
Melnik. Leucine signaling in the pathogenesis of type 2 diabetes and obesity. World I Diabetes. Mar. 15, 2012;3(3):38-53. doi: 10.4239/wjd.v3.i3.38.
Melton, et al. Efficient in vitro synthesis of biologically active RNA and RNA hybridization probes from plasmids containing a bacteriophage SP6 promoter. Nucleic Acids Res. Sep. 25, 1984;12(18):7035-56.
Merck Manual Home Edition online article entitled, "Multiple Sclerosis"—accessed Jun. 20, 2010 at http://www.merck.com/mmhe/print/sec06/ch092/6092b.html.
Merck Manual Home Edition online article entitled, "Introduction: Coronary Artery Disease"—accessed Jun. 20, 2010 at www.merck.com/mmhe/print/sec03/ch033/ch033a.html.
Miwa, et al. Mitochondrial matrix reactive oxygen species production is very sensitive to mild uncoupling. Biochem Sac Trans. Dec. 2003;31(Pt 6):1300-1.
Morris, et al. 1,25-dihydroxyvitamin D3 modulation of adipocyte glucocorticoid function. Obes Res. Apr. 2005;13(4):670-7.
Nairizi, et al. Leucine supplementation of drinking water does not alter susceptibility to diet-induced obesity in mice. Nutr. Apr. 2009;139(4):715-9. Epub Feb. 25, 2009.
Nisoli, et al. Mitochondrial biogenesis by NO yields functionally active mitochondria in mammals. Proc Natl Acad Sci U S A. Nov. 23, 2004;101(47):16507-12. Epub Nov. 15, 2004.
Nisoli, et al. Mitochondrial biogenesis in mammals: the role of endogenous nitric oxide. Science. Feb. 7, 2003;299(5608):896-9.
Nomura, et al. Inhibition of 12-O-tetradecanoylphorbol-13-acetate-induced NF-kappaB activation by tea polyphenols, (−)-epigallocatechin gallate and theaflavins. Carcinogenesis. Oct. 2000;21(10):1885-90.
Notice of allowance dated Mar. 6, 2015 for U.S. Appl. No. 13/866,936.
Notice of allowance dated Mar. 15, 2013 for U.S. Appl. No. 13/549,381.
Notice of allowance dated Apr. 25, 2013 for U.S. Appl. No. 11/542,703.
Notice of allowance dated Apr. 29, 2015 for U.S. Appl. No. 13/866,936.
Notice of allowance dated May 29, 2013 for U.S. Appl. No. 13/549,399.
Notice of allowance dated Aug. 13, 2013 for U.S. Appl. No. 13/549,381.
Notice of allowance dated Aug. 15, 2013 for U.S. Appl. No. 13/549,399.
Notice of allowance dated Dec. 28, 2012 for U.S. Appl. No. 13/549,399.
Ofei, et al. Effects of an engineered human anti-TNF-alpha antibody (CDP571) on insulin sensitivity and glycemic control in patients with NIDDM. Diabetes. Jul. 1996;45(7):881-5.
Office action dated Feb. 5, 2015 for U.S. Appl. No. 13/662,345.
Office action dated Apr. 22, 2013 for U.S. Appl. No. 13/662,345.
Office action dated Jun. 25, 2010 for U.S. Appl. No. 11/543,171.
Office action dated Jul. 15, 2010 for U.S. Appl. No. 11/542,703.
Office action dated Sep. 16, 2013 for U.S. Appl. No. 13/662,345.
Office action dated Nov. 07, 2012 for U.S. Appl. No. 13/549,381.
Office action dated Dec. 23, 2010 for U.S. Appl. No. 11/542,703.
Office action dated Dec. 23, 2010 for U.S. Appl. No. 11/543,171.
Panichi, et al. Calcitriol modulates in vivo and in vitro cytokine production: a role for intracellular calcium. Kidney Int. Nov. 1998;54(5):1463-9.
Park, et al. Resveratrol ameliorates aging-related metabolic phenotypes by inhibiting cAMP phosphodiesterases. Cell. Feb. 3, 2012;148(3):421-33.
Patterson, et al. Excretion of tryptophan-niacin metabolites by young men: effects of tryptophan, leucine, and vitamin B6 intakes. Am J Clin Nutr. Oct. 1980;33(10):2157-67.
Pearce, et al. Sports supplements: A modem case of caveat emptor. Current Sports Medicine Reports. 2005; 4:171-178.

(56) References Cited

OTHER PUBLICATIONS

Peterson, et al. The mechanism of transamination. Function of the histidyl residue at the active site of supernatant aspartate transaminase. J Biol Chem. Feb. 25, 1970;245(4):806-13.
Povolny, et al. The role of recombinant human M-CSF, IL-3, GM-CSF and calcitriol in clonal development of osteoclast precursors in primate bone marrow. Exp Hematol. Apr. 1993;21(4):532-7.
Price, et al. SIRT1 is required for AMPK activation and the beneficial effects of resveratrol on mitochondrial function. Cell Metab. May 2, 2012;15(5):675-90. doi: 10.1016/j.cmet.2012.04.003.
Quinn, et al. Interleukin-15 stimulates adiponectin secretion by 3T3-L1 adipocytes: evidence for a skeletal muscle-to-fat signaling pathway. Cell Biol Int. Jun. 2005;29(6):449-57.
Rasmussen, et al. Regulation of fatty acid oxidation in skeletal muscle. Annu Rev Nutr. 1999;19:463-84.
Reeves. Components of the AIN-93 diets as improvements in the AIN-76A diet. J Nutr. May 1997;127(5 Suppl):838S-841S.
Remington's Pharmaceutical Sciences, 18th Edition, 1990, Mack Publishing Co.
Roberts, et al. Nutrition and aging: changes in the regulation of energy metabolism with aging. Physiol Rev. Apr. 2006;86(2):651-67.
S Bear. Nother way to get leucine for the 6 week cure, 2009, pp. 1-5.
Sabatini, et al. Tadalafil alters energy metabolism in C2C12 skeletal muscle cells. Acta Biochim Pol. 2011;58(2):237-41. Epub Jun. 16, 2011.
Schulze-Osthoff, et al. Oxidative stress and signal transduction. Int J Vitam Nutr Res. 1997;67(5):336-42.
Sellden, et al. Augmented thermic effect of amino acids under general anaesthesia: a mechanism useful for prevention of anaesthesia-induced hypothermia. Clin Sci (Lond). May 1994;86(5):611-8.
Shangari, et al. The cytotoxic mechanism of glyoxal involves oxidative stress. Biochem Pharmacol. Oct. 1, 2004;68(7):1433-42.
Shi, et al. 1alpha,25-dihydroxyvitamin D3 inhibits uncoupling protein 2 expression in human adipocytes. FASEB J. Nov. 2002;16(13):1808-10. Epub Sep. 5, 2002.
Shi, et al. 1alpha,25-Dihydroxyvitamin D3 modulates human adipocyte metabolism via nongenomic action. FASEB J. Dec. 2001;15(14):2751-3. Epub Oct. 15, 2001.
Simeone, et al. How retinoids regulate breast cancer cell proliferation and apoptosis. Cell Mol Life Sci. Jun. 2004;61(12):1475-84.
Soares, et al. Effects of oxidative stress on adiponectin secretion and lactate production in 3T3-L1 adipocytes. Free Radic Biol Med. Apr. 1, 2005;38(7):882-9.
Solerte, et al. Metabolic effects of orally administered amino acid mixture in elderly subjects with poorly controlled type 2 diabetes mellitus. Am J Cardiol. Apr. 22, 2004;93(8A):23A-29A.
Song, et al. Methionine-induced hyperhomocysteinemia promotes superoxide anion generation and NFkappaB activation in peritoneal macrophages of C57BL/6 mice. J Med Food. 2004 Summer;7(2):229-34.
Sonta, et al. Evidence for contribution of vascular NAD(P)H oxidase to increased oxidative stress in animal models of diabetes and obesity. Free Radic Biol Med. Jul. 1, 2004;37(1):115-23.
Sorescu, et al. Superoxide production and expression of nox family proteins in human atherosclerosis. Circulation. Mar. 26, 2002;105(12):1429-35.
Stipanuk. Leucine and protein synthesis: mTOR and beyond. Nutr Rev. Mar. 2007;65(3):122-9.
Sun, et al. 1, 25(OH)2D3 and reactive oxygen species interatively stimulate angiotensinogen expression in differentiated 3T3-L1 adipocytes. FASEB J. 2005; 19:A70, No. 67.8 (abstract only).
Sun, et al. Calcium and dairy products inhibit weight and fat regain during ad libitum consumption following energy restriction in Ap2-agouti transgenic mice. J Nutr. Nov. 2004;134(11):3054-60.
Sun, et al. Dietary calcium regulates ROS production in aP2-agouti transgenic mice on high-fat/high-sucrose diets. Int J Obes (Lond). Sep. 2006;30(9):1341-6. Epub Mar. 7, 2006.
Sun, et al. Dual effects of 1-alpha,25-(OH)2-D3 on adipocyte apoptosis. FASEB J. 2004; 18:A49 (abstract only).
Sun, et al. Effects of mitochondrial uncoupling on adipocyte intracellular Ca(2+) and lipid metabolism. J Nutr Biochem. Apr. 2003;14(4):219-26.
Sun, et al. Leucine and calcium regulate fat metabolism and energy partitioning in murine adipocytes and muscle cells. Lipids. Apr. 2007;42(4):297-305. Epub Feb. 20, 2007.
Sun, et al. Leucine modulation of mitochondrial mass and oxygen consumption in skeletal muscle cells and adipocytes. Nutr Metab (Lond). Jun. 5, 2009;6:26. doi:10.1186/1743-7075-6-26.
Sun, et al. Reactive oxygen species stimulate cell proliferation and down-regulate UCP2 expression in 3T3-L1 adipocytes. Obesity Research. 2004; 11: A21, No. 80-OR (abstract only).
Sun, et al. Role of uncoupling protein 2 (UCP2) expression and 1alpha, 25-dihydroxyvitamin D3 in modulating adipocyte apoptosis. FASEB J. Sep. 2004;18(12):1430-2. Epub Jul. 1, 2004.
Suzuki, et al. Oxidants as stimulators of signal transduction. Free Radic Biol Med. 1997;22(1-2):269-85.
Suzuki, et al. Relationship between obesity and serum markers of oxidative stress and inflammation in Japanese. Asian Pac J Cancer Prev. Jul.-Sep. 2003;4(3):259-66.
Tappy, et al. Thermic effect of infused amino acids in healthy humans and in subjects with insulin resistance. Am J Clin Nutr. Jun. 1993;57(6):912-6.
Tennen, et al. Finding a target for resveratrol. Cell. Feb. 3, 2012;148(3):387-9.
Thannickal, et al. Reactive oxygen species in cell signaling. Am J Physiol Lung Cell Mol Physiol. Dec. 2000;279(6):L1005-28.
Thompson, et al. Effect of energy-reduced diets high in dairy products and fiber on weight loss in obese adults. Obes Res. Aug. 2005;13(8):1344-53.
Thomson, et al. Effects of nine weeks of beta-hydroxy-beta-methylbutyrate supplementation on strength and body composition in resistance trained men. Journal of strength and conditioning research / National Strength & Conditioning Association 23: 827-835, 2009.
Upham, et al. Hydrogen peroxide inhibits gap junctional intercellular communication in glutathione sufficient but not glutathione deficient cells. Carcinogenesis. Jan. 1997;18(1):37-42.
Valle, et al. Low-grade systemic inflammation, hypoadiponectinemia and a high concentration of leptin are present in very young obese children, and correlate with metabolic syndrome. Diabetes Metab. Feb. 2005;31(1):55-62.
Van Loon. Leucine as a pharmaconutrient in health and disease. Curr Opin Clin Nutr Metab Care. Jan. 2012;15(1):71-7. Abstract only.
Verdin, et al. Sirtuin regulation of mitochondria: energy production, apoptosis, and signaling. Trends Biochem Sci. Dec. 2010;35(12):669-75. Epub Sep. 20, 2010.
Volk, et al. Transient Ca2+ changes in endothelial cells induced by low doses of reactive oxygen species: role of hydrogen peroxide. Mol Cell Biochem. Jun. 1997;171(1-2):11-21.
Wajchenberg. Subcutaneous and visceral adipose tissue: their relation to the metabolic syndrome. Endocr Rev. Dec. 2000;21(6):697-738.
Warner. Metformin Linked to B12 Deficiency, 2009, WebMD, pp. 1-2.
Weisberg, et al. Obesity is associated with macrophage accumulation in adipose tissue. J Clin Invest. Dec. 2003;112(12):1796-808.
Weitzman, et al. Free radical adducts induce alterations in DNA cytosine methylation. Proc Natl Acad Sci U S A. Feb. 15, 1994;91(4):1261-4.
Wilson, et al. Effects of beta-hydroxy-beta-methylbutyrate (HMB) on exercise performance and body composition across varying levels of age, sex, and training experience: A review. Nutr Metab (Loud). Jan. 3, 2008;5:1.
Wiseman, et al. Damage to DNA by reactive oxygen and nitrogen species: role in inflammatory disease and progression to cancer. Biochem J. Jan. 1, 1996;313 ( Pt 1):17-29.
Xiao, et al. Leucine deprivation increases hepatic insulin sensitivity via GCN2/mTOR/S6K1 and AMPK pathways. Diabetes. Mar. 2011;60(3):746-56. Epub Jan. 31, 2011.

(56) References Cited

OTHER PUBLICATIONS

Xu, et al. Chronic inflammation in fat plays a crucial role in the development of obesity-related insulin resistance. J Clin Invest. Dec. 2003;112(12):1821-30.
Xue, et al. Relationship between human adipose tissue agouti and fatty acid synthase (FAS). J Nutr. Oct. 2000;130(10):2478-81.
Xue, et al. The agouti gene product inhibits lipolysis in human adipocytes via a Ca2+-dependent mechanism. FASEB J. Oct. 1998;12(13):1391-6.
Yang, et al. Leucine metabolism in regulation of insulin secretion from pancreatic beta cells. Nutr Rev. May 2010;68(5):270-9.
Zanchi, et al. Potential antiproteolytic effects of L-leucine: observations of in vitro and in vivo studies. Nutr Metab (Lond). Jul. 17, 2008;5:20.
Zemel, et al. Calcium and dairy acceleration of weight and fat loss during energy restriction in obese adults. Obes Res. Apr. 2004;12(4):582-90.
Zemel, et al. Dairy augmentation of total and central fat loss in obese subjects. Int J Obes (Lond). Apr. 2005;29(4):391-7.
Zemel, et al. Effects of dairy compared with soy on oxidative and inflammatory stress in overweight and obese subjects. Am J Clin Nutr. Jan. 2010;91(1):16-22. Epub Nov. 4, 2009.
Zemel, et al. Regulation of adiposity by dietary calcium. FASEB J. Jun. 2000;14(9):1132-8.
Zemel,et al. Effects of calcium and dairy on body composition and weight loss in African-American adults. Obes Res. Jul. 2005;13(7):1218-25.
Zemel. Calcium and dairy modulation of obesity risk. Obes Res. Jan. 2005;13(1):192-3.
Zemel. Role of calcium and dairy products in energy partitioning and weight management. Am J Clin Nutr. May 2004;79(5):907S-912S.
Zemel. The role of dairy foods in weight management. J Am Coll Nutr. Dec. 2005;24(6 Suppl):537S-46S.
Zhang, et al. Increasing dietary leucine intake reduces diet-induced obesity and improves glucose and cholesterol metabolism in mice via multimechanisms. Diabetes. Jun. 2007;56(6):1647-54. Epub Mar. 14, 2007.
Zhang, et al. Occurrence of beta-hydroxyl-beta-methyl butyrates in foods and feed. Protein and amini acid nutrition. 1994; A464: 2685-2690.
Notice of allowance dated Feb. 1, 2016 for U.S. Appl. No. 14/927,255.
Anonymous: "European commission health and consumer protection directorate-general directorate C-scientific opinions c2-management of scientific committees II; scientific co-operation and networks opinion of the scientific committee on food on the tolerable upper intake levels of nicotinic acid and nicotinamide," May 6, 2002.Available at: http://ec.europa.eu/foods/fs/sc/scf/out80j_en.pdf. Retrieved on Sep. 21, 2016.
Anonymous: "GRAS notification for L-Leucine produced by innonio limited," May 27, 2014, Available at: http://www.fda.gov/ucm/groups/fdagov-public/@fdaov-foods-gen/documents/document/ucm407679.pdf. Retrieved on Sep. 21, 2016.
Arend, et al. Inhibition of the production and effects of interleukin-1 and tumor necrosis factor alpha in rheumatoid arthritis. Arthritis Rheum. Feb. 1995;38(2):151-60.
Balabolkin, et al., The role of thiazolidinediones in compensation of carbohydrate metabolism in type 2 diabetes and in the prevention of vascular complications of diabetes. 1998-2017. Retrieved from: https://www.lvrach.ru/2007/02/4534786/.
Bartges, et al. Calculating a patient's nutritional requirements. Veterinary Medicine. 2004; 99:632.
Brennan, et al. Inhibitory effect of TNF alpha antibodies on synovial cell interleukin-1 production in rheumatoid arthritis. Lancet. Jul. 29, 1989;2(8657):244-7.
Carlson, LA. Nicotinic acid: the broad-spectrum lipid drug. A 50th anniversary review. J. Intern Med. Aug. 2005;258(2):94-114.

Carroll, et al. Antagonism of the IL-6 cytokine subfamily—a potential strategy for more effective therapy in rheumatoid arthritis. Inflamm Res. Jan. 1998;47(1):1-7.
Caton, et al., Metformin opposes impaired AMPK and SIRT1 function and deleterious changes in core clock protein expression in white adipose tissue of genetically-obese db/db mice. Diabetes Obes Metab 13, 1097-1104 Dec. 13, 2011.
Co-pending U.S. Appl. No. 15/447,049, filed Mar. 1, 2017.
Co-pending U.S. Appl. No. 15/513,115, filed Mar. 21, 2017.
Creider, et al., Niacin: another look at an underutilized lipid-lowering medication. Nature Reviews Endocrinology, 2012. 8:517-528.
European search report and opinion dated Aug. 22, 2016 for EP Application No. 14770824.
European Search Report dated Sep. 30, 2016 for European Application No. 14768984.8.
Fraquelli, M. et al., Reproducibility of transient elastography in the evaluation of liver fibrosis in patients with chronic liver disease. Gut. Jan. 25, 2007, vol. 56; pp. 968-973; Abstract; pp. 969 1st column, 2nd paragraph; DOI 10.1136/gut.2006.111302.
Fu, L., et al., Interaction between leucine and phosphodiesterase 5 inhibition in modulating insulin sensitivity and lipid metabolism. Diabetes, Metabolic syndrome and obesity: Targets and therapy. May 6, 2015; vol. 8: pp. 227-239.; abstract; p. 228, 1st column, 3rd paragraph to 2nd column, 1st paragraph.
Gilhuly, K. Niacin Dosage for lowering Triglycerides. Livestrong. Jul. 27, 2015. Available at: http://www.livestrong.com/article/460725-the-dosage-of-niacin-for-lowering-triglycerides/#ixzz2N03KhDZu. Accessed on Jun. 8, 2017.
Haworth, et al. Expression of granulocyte-macrophage colony-stimulating factor in rheumatoid arthritis: regulation by tumor necrosis factor-alpha. EurJ Immunol. Oct. 1991;21(10):2575-9.
Hornstra, et al. Essential fatty acids in pregnancy and early human development. Eur J Obstet Gynecol Reprod Biol. Jul. 1995;61(1):57-62.
Howitz, K.T. et al., Small molecule activators of sirtuins extend saccharomyces cerevisiae lifespan. Letters to Nature. 2003; 425:191-196.
International search report and written opinion dated Jul. 21, 2014 for PCT/US2014/016592.
International search report dated Jul. 14, 2014 for PCT Application No. US 2014/026816.
International Search Report dated Nov. 28, 2016 for International Application No. PCT/US2016/049272.
Ionut, et al. Novel canine models of obese prediabetes and mild type 2 diabetes. Am J Physiol Endocrinol Metab. Jan. 2010; 298(1):E38-48. doi: 10.1152/ajpendo.00466.2009. Epub Oct. 20, 2009.
Kies, E. et al., Interrelationship of leucine with lysine, tryptophan, and niacin as they influence protein value of cereal gains for humans. Cereal Chemistry. Apr. 1972; 223-231.
Laflamme. Development and validation of a body condition score system for dogs. Canine Practice. 1997; 22:10-15.
Lehman, et al. Assessment of coronary plaque progression in coronary computed tomography angiography using a semiquantitative score. JACC Cardiovasc Imaging. Nov. 2009;2(11):1262-70. doi: 10.1016/j.jcmg.2009.07.007.
Lim, et al. Intakes of dietary docosahexaenoic acid ethyl ester and egg phosphatidylcholine improve maze-learning ability in young and old mice. J Nutr. Jun. 2000;130(6):1629-32.
Mawby, et al. Comparison of various methods for estimating body fat in dogs. J Am Anim Hosp Assoc. Mar.-Apr. 2004;40(2):109-14.
Mooney, et al., Mechanisms underlying the metabolic actions of galegine that contribute to weight loss in mice. Br J Pharmacal. Apr. 2008; 153(8): 1669-1677. Published online Feb. 25, 2008. doi: 10.1038/bjp.2008.37.
Moser, et al. Interleukin 1 and tumor necrosis factor stimulate human vascular endothelial cells to promote transendothelial neutrophil passage. J Clin Invest. Feb. 1989;83(2):444-55.
Muscle Synergy: Advanced Nitric Oxide and muscle building supplement. Beverly International. Accessed on Oct. 18, 2012. Available at: https://web.archive.org/web/20121018004354/http://www.beverlyinternational.com/products/muscle-synergy.html.

(56) References Cited

OTHER PUBLICATIONS

Musso, G. et al., Impact of current treatments on liver disease, glucose metabolism and cardiovascular risk in non-alcoholic fatty liver disease (NAFLD): a systematic review and meta-analysis of randonmised trials. Diabetologia (2012) 55:885-904.
Nagao, et al. Dietary diacylglycerol suppresses accumulation of body fat compared to triacylglycerol in men in a double-blind controlled trial. J Nutr. Apr. 2000;130(4):792-7.
Nakagawa, I. Effect of an excess intake of leucine, with and without additions of vitamin B6 and/or niacin, on tryptophan and niacin metabolism in rats. Journal of nutritional science and vitaminology. 23(6). Jan. 1, 1977. p. 535-548.
Nin, et al., Role of deleted in breast cancer 1 (DBC1) protein in SIRT1 deacetylase activation induced by protein kinase A and AMP-activated protein kinase. J Biol Chem. Jul. 6, 2012;287(28):23489-501. doi: 10.1074/jbc.M112.365874. Epub May 2, 2012.
Notice of allowance dated Feb. 27, 2017 for U.S. Appl. No. 15/164,647.
Notice of Allowance dated Mar. 23, 2017 for U.S. Appl. No. 15/206,125.
Notice of allowance dated Apr. 11, 2016 for U.S. Appl. No. 14/472,081.
Notice of Allowance dated Apr. 27, 2017 for U.S. Appl. No. 15/119,695.
Notice of Allowance dated Oct. 26, 2016 for U.S. Appl. No. 14/772,366.
Office Action dated Apr. 5, 2017 for U.S. Appl. No. 14/843,873.
Office Action dated Dec. 15, 2016 for U.S. Appl. No. 14/770,418.
OpenSource Diets. Product Data D12451. Report Repeat Revise Where NutriPhenomics Begins Research Diets, Inc. 20. Last modified: Feb. 28, 2013.
Ouyang, et al., Metformin Activates AMP Kinase through Inhibition of AMP Deaminase. J Biol Chem 286, 1-11 Jan. 7, 2011.
Park, et al. Resveratrol ameliorates aging-related metabolic phenotypes by inhibiting cAMP phosphodiesterases. Cell. Feb. 3, 2012;148(3):421-33. doi: 10.1016/j.cell.2012.01.017.
Phan, et al. Effects of niacin on glucose levels, coronary stenosis progression, and clinical events in subjects with normal baseline glucose levels (<100 mg/dl): a combined analysis of the Familial Atherosclerosis Treatment Study (FATS), HDL-Atherosclerosis Treatment Study (HATS), Armed Forces Regression Study (AFREGS), and Carotid Plaque Composition by MRI during lipid-lowering (CPC) study. Am J Cardiol. Feb. 1, 2013;111(3):352-5. doi: 10.1016/j.amjcard.2012.09.034. Epub Nov. 17, 2012.
Rogers. A healthy body, a healthy mind: long-term impact of diet on mood and cognitive function. Proc Nutr Soc. Feb. 2001;60(1):135-43.
Saumet, et al. Non-invasive measurement of skin blood flow: comparison between plethysmography, laser-Doppler flowmeter and heat thermal clearance method. Int J Microcirc Clin Exp. 1986;5(1):73-83.
Shalwala, M., et al., SIRT1 Activation Mediates Sildenafil-Induced Cardioprotection Against Ischemia/Reperfusion Injury in Mice. Circulation, 122(Suppl 21 ), 2010: A 14584-A 14584.
Truswell, A.S. Effect of surplus leucine intake on serum cholesterol in man. Proceedings of the nutrition society. 23(2). Sep. 1, 1964. pp. XLVI-XLVII.
Sunvold, et al. Dietary fiber for dogs: IV. In vitro fermentation of selected fiber sources by dog fecal inoculum and in vivo digestion and metabolism of fiber-supplemented diets. J Anim Sci. Apr. 1995;73(4):1099-109.
Witters, L.A., The blooming of the French lilac. J Clin Invest. Oct. 15, 2001; 108(8): 1105-1107. doi: 10.1172/JCI14178.
Wojtczak, A., "Prevention" in glossary of medical education terms: Parts 1-7. Ed. Medical Teacher. vol. 24, Nos. 2-6 and vol. 25, No. 1 &2. 2002.
Yalkowsky, et al. Potentiometric titration of monomeric and micellar acylcarnitines. J Pharm Sci. Jun. 1970;59(6):798-802.
Yalkowsky, et al. Some micellar properties of long-chain acylcarnitines. J Colloid Interface Sci. Dec. 1970;34(4):525-33.
Yamka, et al. In vivo measurement of flatulence and nutrient digestibility in dogs fed poultry by-product meal, conventional soybean meal, and low-oligosaccharide low-phytate soybean meal. Am J Vet Res. Jan. 2006;67(1):88-94.
Yudkin, et al. Inflammation, obesity, stress and coronary heart disease: is interleukin-6 the link? Atherosclerosis. Feb. 2000;148(2):209-14.
Zhang, Y. Increasing dietary leucine intake reduces diet-induced obesity and improves glucose and cholesterol metabolism in mice via multimechanisms. Diabetes, 56(6); Mar. 27, 2007. pp. 1647-1654.
Williams, et al., Diabetes and Nonalcoholic Fatty Liver Disease: A Pathogenic Duo. Endocrine Reviews. Feb. 2013; 34:84-129.
Bruckbauer, et al., A combination of leucine, metformin, and sildenafil treats nonalcoholic fatty liver disease and steatohepatits in mice. International Journal of Hepatology, vol. 2016, No. Article IDS 9185987, 2016, pp. 1-16, XP055407691.
Colak, et al., Sirt1 as a potential therapeutic target for treatment of nonalcoholic fatty liver disease. Medical Science Monitor, vol. 17, No. 5, May 1, 2011, pp. HY5-HY9, XP055407742.
Co-pending U.S. Appl. No. 15/595,911, filed May 15, 2017.
Co-pending U.S. Appl. No. 15/619,406, filed Jun. 9, 2017.
Co-pending U.S. Appl. No. 15/638,241, filed Jun. 29, 2017.
Dell'Agli et al., Potent inhibition of human phosphodiesterase-5 by icariin derivatives, Journal of Natural Products, Sep. 9, 2008, vol. 71, No. 9, p. 1513-1517.
European Search Report and Search Opinion dated Oct. 4, 2017 for European Patent Application No. EP 15755565.7.
Hang et al., Synergy between metformin and leucine in sirtuin signaling and fat oxidation in vitro, and in reducing lipid accumulation in diet-induced obese mice. Diabetes, vol. 63, No. Suppl 1, Jun. 2014, p. A463, XP055408614.
Kuda, et al., n-3 fatty acids and rosiglitazone improve insulin sensitivity through additive stimulatory effects on muscle glycogen synthesis in mice fed a high-fat diet, Diabetologia, Mar. 11, 2009, vol. 52, No. 5, p. 941-951.
Li, et al., Leucine supplementation increases SIRT1 expression and prevents mitochondrial dysfunction and metabolic disorders in high-fat diet-induced obese mice. Am J Physiology. Endocrinology and metabolism, Sep. 11, 2012; 303(10): p. E1234-E1244.
Manna, et al., Resveratrol Suppresses TNF-Induced Activation of Nuclear Transcription Factors NF-kB, Activator Protein-1, and Apoptosis: Potential Role of Reactive Oxygen Intermediates and Lipid Peroxidation1. J Immunol 2000; 164:6509-6519.
Matsui, et al., Metformin reduces body weight gain and improves glucose intolerance in high-fat diet-fed C57BL/6J mice, Biological and Pharmaceutical Bulletin, Jun. 2010, vol. 33, No. 6, p. 963-970.
Notice of Allowance dated Aug. 18, 2017 for U.S. Appl. No. 15/595,911.
Notice of Allowance dated Sep. 28, 2017 for U.S. Appl. No. 14/843,873.
Uckert, S & Oelke, M, Phosphodiesterase (PDE) inhibitors in the treatment of lower urinary tract dysfunction, British Journal of Clinical Pharmacology, 2011, vol. 72, No. 2, p. 197-204.
Zemel, et al., Synergistic effects of leucine and beta-hydroxy-beta-methyl-butyrate (HMB) with phosphodiesterase (PDE) inhibitors on sirtuin activation. FASEB Journal, vol. 27, Apr. 2013, p. 637.9, XP055408009.
Co-pending U.S. Appl. No. 15/817,057, filed Nov. 17, 2017.
Co-pending U.S. Appl. No. 15/844,101, filed Dec. 15, 2017.
Co-pending U.S. Appl. No. 15/851,544, filed Dec. 21, 2017.
Notice of Allowance dated Nov. 16, 2017 for US. Appl. No. 15/619,406.

* cited by examiner

AREA UNDER THE CURVE FOR WEEK 5 GTT

COMPOSITIONS AND METHODS FOR INCREASING ENERGY METABOLISM

CROSS-REFERENCE

This application claims benefit of priority to U.S. Provisional Application No. 61/726,006, filed Nov. 13, 2012, which is incorporated herein by reference in its entirety for all purposes.

BACKGROUND OF THE INVENTION

All organisms have developed exquisite metabolic pathways that maintain energy homeostasis by balancing their intake and metabolism of energy with their expenditure needs of the organism. In mammals, these pathways regulate food intake, glucose homeostasis, storage of energy in fat and/or muscle, and mobilization of energy by, for instance, physical activity. Malfunctioning of these pathways, often resulting from excess energy intake relative to energy expenditure, leads to imbalanced energy homeostasis, which in turn can lead to a wide range of metabolic disorders. Amongst them are obesity, diabetes, hypertension, arteriosclerosis, high cholesterol, and hyperlipidemia.

The high incidence of metabolic disorders in humans and the related impact on health and mortality presents a significant burden to public health. For instance, obesity, clinically defined as a body mass index of over 30 kg/m2, is estimated to affect 35.7% of the U.S. adult population. Obesity increases the likelihood of many diseases, such as heart disease and type II diabetes, and obesity is one of the leading preventable causes of death worldwide. In the U.S., obesity is estimated to cause roughly 110,000-365,000 deaths per year. Diabetes is a metabolic disorder characterized by high blood glucose levels or low glucose tolerance, and is estimated to affect 8% of the U.S. population. Diabetes is also significantly associated with higher risk of death from vascular disease, cancer, renal disease, infectious diseases, external causes, intentional self-harm, nervous system disorders, and chronic pulmonary disease (N Engl J Med 2011; 364:829-841). Metabolic syndrome, in which subjects present with central obesity and at least two other metabolic disorders (such as high cholesterol, high blood pressure, or diabetes), is estimated to affect 25% of the U.S. population.

Sirtuins are highly conserved protein deacetylases and/or ADP-ribosyltransferases that have been shown to extend lifespan in lower model organisms, such as yeast, *C. elegans*, and *drosophila*. In mammals, sirtuins have been shown to act as metabolic sensors, responding to environmental signals to coordinate the activity of genes that regulate multiple energy homeostasis pathways. For example, studies have shown that sirtuin activation mimics the effects of caloric restriction, an intervention demonstrated to significantly extend lifespan, and activates genes that improve glucose homeostasis and the conversion of fat to energy by fatty acid oxidation.

The sirtuin pathway also includes phosphodiesterases (PDEs). PDEs are enzymes that interact with cyclic adenosine monophosphates (cAMPs) and cyclic guanosine monophosphates (cGMPs). The PDE family of enzymes comprises multiple subclasses, including PDE 1-11 in humans. Inhibitors of these phosphodiesterases can prevent the inactivation of cAMPs and cGMPs, and can have a variety of different physiological effects. The PDE inhibitors can be selective, by preferentially inhibiting one PDE subclass as compared to another subclass, or non-selective, which have a substantially lower degree of selectivity for individual PDE subclasses. Sildenafil is an example of a selective PDE inhibitor that has shown selective inhibition of PDE 5. Sildenafil is a pharmaceutically active agent that has been used to treat pulmonary hypertension, erectile dysfunction, and altitude sickness.

Many efforts have been attempted to develop treatments for metabolic disorders by targeting specific energy metabolism pathways. These efforts have resulted in the development of, for example, isoflavones (U.S. Patent Application No. 20110165125), tetrahydrolipstatin (U.S. Pat. No. 6,004,996), and compositions that modulate the SIRT1 and AMPK pathways (U.S. Patent Application Nos. 20100210692, 20100009992, 20070244202 and 20080176822). However, these efforts are of limited success. For instance, use of the SIRT1 activator resveratrol in humans is hampered by its limited bioavailability, necessitating high dosages which have raised safety concerns. Thus, there remains a great need for treatments that can address a wide range of metabolic disorders by safely regulating metabolic pathways.

SUMMARY OF THE INVENTION

The present invention generally relates to the field of regulation of energy metabolism. In some embodiments, the present invention provides for compositions, methods, and kits for regulating energy metabolism using PDE inhibitors, such as PDE 5, and branched chain amino acids.

Compositions including PDE inhibitors can be effective for regulating energy metabolism because PDEs are components of the sirtuin pathway. Because these PDE inhibitors can have an effect on the sirtuin pathway, compositions including PDE inhibitors, both selective and non-selective, can have beneficial effects on regulating energy metabolism.

The present invention addresses the need for improved compositions and supplements for regulating energy metabolism. The regulation of energy metabolism can allow for decreases in weight or adipose tissue, increases in fat oxidation or insulin sensitivity, and/or the decrease of inflammation or oxidative stress. These effects can be by way of an increase in or regulation of energy metabolism, including cellular metabolism and mitochondrial biogenesis.

The subject application provides compositions useful for inducing an increase in fatty acid oxidation and mitochondrial biogenesis in a subject. The compositions also cause activation of Sirt1 and Sirt3, thereby mediating beneficial downstream effects, including prevention and treatment of diabetes, cardiovascular disease and inflammatory disease. Such compositions contain a PDE inhibitor, including but not limited to PDE5 inhibitor such as avanafil, iodenafil, mirodenafil, sildenafil, tadalafil, icariin, vardenafil, udenafil, or zaprinst in combination with a branched chain amino acid and/or metabolites thereof (e.g. beta-hydroxymethylbutyrate (HMB), leucine, keto-isocaproic acid (KIC) or combinations of HMB, KIC and/or leucine). The branched chain and amino acid can be leucine and the metabolites can be HMB and KIC. The subject application also provides methods of increasing fatty acid oxidation in a subject comprising the administration of the disclosed compositions.

One aspect of the invention provides for a composition effective for enhancing energy metabolism comprising: (a) a PDE inhibitor, e.g., a PDE5 inhibitor; and (b) leucine and/or a leucine metabolite. In some embodiments, the composition enhances energy metabolism in the subject to a greater degree as compared to administering to the subject component (a) or (b) alone. In some embodiments, the leucine and/or leucine metabolite are present in free amino acid and/or free amino acid metabolite form. For example, the leucine may be present in a form that does not comprise a peptide bond.

In some embodiments, the enhanced energy metabolism is measured by an increase in fatty acid oxidation of an adipocyte by at least about 300%, an increase in glucose utilization of an adipocyte by at least 150%, an increase in glucose utilization of an adipocyte by a change of at least 60%, or an increase in mitochondrial biomass by at least about 15%.

In some embodiments, the enhanced energy metabolism is measured by a reduction in postprandial blood glucose of at least 20%, a reduction in postprandial insulin by at least 30%, a reduction in fasting blood glucose by at least 40%, a reduction in fasting insulin by at least 40%, a reduction in blood glucose response to glucose load by at least 15%, a two-fold improvement in insulin tolerance results, or a reduction in inflammatory stress by at least 20%. In some embodiments, the blood glucose response to glucose load is measured by area under a glucose tolerance curve.

In some embodiments, the PDE 5 inhibitor is avanafil, iodenafil, mirodenafil, sildenafil, tadalafil, icariin, vardenafil, udenafil, or zaprinst. In other embodiments, the PDE 5 inhibitor is sildenafil or icariin. In some embodiments, the PDE 5 inhibitor is icariin. In some embodiments, component (b) is HMB. In some embodiments, component (b) is free leucine. In other embodiments, the composition further comprises a non-selective PDE inhibitor. In other embodiments, the composition further comprises vitamin B6.

In some embodiments, the composition further comprises a pharmaceutically active agent. The composition can further comprise two pharmaceutically active agents. One of the two pharmaceutically active agents can be sildenafil. In some embodiments, the composition is formulated for oral consumption.

The composition can be a unit dosage comprising a sub-therapeutic amount of component (a). The sub-therapeutic amount of component (a) can be between about 0.1 and 20 mg of sildenafil. The sub-therapeutic amount of component (a) can be between about 0.1 and 10 mg of sildenafil. The sub-therapeutic amount of component (a) can be between about 0.5-50 mg of avanafil, 0.05-10 mg of iodenafil, 0.25-25 mg of mirodenafil, 0.01-1.25 mg of tadalafil, 0.01-1.25 mg of vardenafil, 0.5-50 mg of udenafil, 0.5-50 mg of zaprinst, or 0.05-100 mg of icariin. Component (b) can comprise at least about 500 mg of leucine. Component (b) can comprise at least about 200 mg of HMB. In some embodiments, component (b) comprises 50-1000 mg of free leucine. Component (b) can comprise 500-700 mg of free leucine.

Another aspect of the invention provides for a composition effective for enhancing energy metabolism comprising: (a) a PDE 5 inhibitor; and (b) a polyphenol, wherein the composition enhances energy metabolism in the subject to a greater degree as compared to administering to the subject component (a) or (b) alone. The polyphenol can be resveratrol.

The polyphenol can be a stilbene or hydroxycinnamic acid. The polyphenol can be chlorogenic acid, resveratrol, caffeic acid, piceatannol, ellagic acid, epigallocatechin gallate (EGCG), grape seed extract, or any analog thereof. The composition can further comprise leucine and/or a leucine metabolite.

One aspect of the invention provides for a method of regulating energy metabolism in a subject in need thereof comprising administering to the subject a composition described herein. The composition can be administered orally.

Another aspect of the invention provides for a method of regulating energy metabolism comprising identifying a subjecting having or prone to obesity or diabetes, administering to the subject a composition described herein.

The invention also provides for a method of regulating energy metabolism in a subject in need thereof comprising administering to the subject a unit dosage comprising a subtherapeutic amount of a PDE inhibitor, e.g., a PDE 5 inhibitor and at least about 500 mg of leucine or 200 mg of HMB. The subtherapeutic amount of the PDE inhibitor, e.g., a PDE 5 inhibitor can be less than about 10 mg/day. The PDE 5 inhibitor can be sildenafil. The leucine may be in free amino acid form, e.g., intact form. For example, the leucine may be present in a form that does not comprise a peptide bond.

One aspect of the invention provides for a method for increasing energy metabolism in a subject comprising: administering a composition described herein at a selected dosing level, wherein the selected dosing level induces a circulating level of about 1 nM sildenafil and about 0.5 mM leucine in the subject. The leucine may be in free amino acid form, e.g., intact form. For example, the leucine may be present in a form that does not comprise a peptide bond. In some cases, any of the methods herein comprise administering the composition for over 1 week, for over 2 weeks, or for over 6 weeks.

The invention also provides a method of treating diabetes in a subject in need thereof, comprising administering to the subject a therapeutically effective composition comprising a PDE 5 inhibitor; and a branched-chain amino acid in free amino acid form or a metabolite thereof. The diabetes may be, e.g., Type I diabetes or Type II diabetes. For example, administration of the composition can improve insulin sensitivity in a subject. Type I diabetes may be characterized by reduced ability to produce insulin as compared to a subject without Type I diabetes. Administration of a composition described herein can improve the sensitivity of a subject with Type I diabetes to the insulin that is produced by or administered to the subject. The improved sensitivity can be greater than the sensitivity of the subject as measured before administration of the composition. Type II diabetes may be characterized by reduced sensitivity to insulin. Accordingly, administration of a composition described herein can improve insulin sensitivity in a subject with Type II diabetes. The diabetes may be a diet-induced diabetes. In some embodiments, the branched chain amino acid is free leucine. In some embodiments, the branched chain amino acid metabolite is HMB. It is understood that the therapeutically effective composition can be any of the compositions described herein.

In some embodiments, the PDE5 inhibitor is icariin. In some embodiments, the PDE5 inhibitor is sildenafil. In some embodiments, the PDE5 inhibitor is tadalafil. In some embodiments, the PDE5 inhibitor is vardenafil. In some embodiments, the PDE5 inhibitor is udenafil. In some embodiments, the PDE5 inhibitor is zaprinst.

In some embodiments, the method comprises administering the therapeutically effective composition orally. In some embodiments, the method comprises administering the therapeutically effective composition for at least one week. In some embodiments, the method comprises administering the therapeutically effective composition for at least two weeks. In some embodiments, the method comprises administering the therapeutically effective composition for at least six weeks.

In some embodiments, administering the therapeutically effective composition improves a symptom of diabetes in the subject. The symptom of diabetes can be a symptom of Type I and/or Type II Diabetes. The improvement of the diabetes symptom can be measured by a reduction in postprandial blood glucose of at least 20%, a reduction in postprandial insulin by at least 30%, a reduction in fasting blood glucose by at least 40%, a reduction in fasting insulin by at least 40%, a reduction in blood glucose response to a glucose load by at least 15%, a two-fold improvement in insulin tolerance results, or a reduction in inflammatory stress by at least 20%. In some embodiments, the blood glucose response to glucose load is measured by area under a glucose tolerance curve.

Another aspect of the invention provides for a kit comprising a multi-day supply of unit dosages of a composition described herein and instructions directing the administration of said multi-day supply over a period of multiple days. In some embodiments, the kit further comprises a wearable activity monitor.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawing(s) of which:

DETAILED DESCRIPTION OF THE INVENTION

Figure 1:
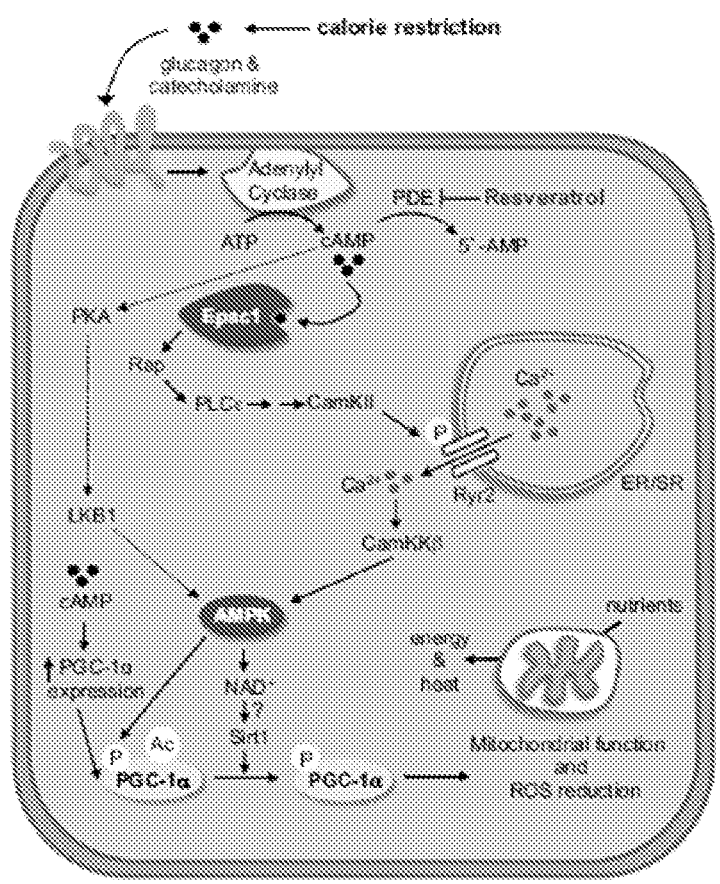
FIG. 1 depicts a diagram showing a sirtuin pathway.

Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. Unless stated otherwise, the present invention is not limited by the illustrated ordering of acts or events, as some acts may occur in different orders and/or concurrently with other acts or events. Furthermore, not all illustrated acts or events are required to implement a methodology in accordance with the present invention. The concentration of various components in the disclosed compositions are exemplary and not meant to be limited to the recited concentration per se.

As used herein, the term "subject" or "individual" includes mammals. Non-limiting examples of mammals include humans and mice, including transgenic and non-transgenic mice. The methods described herein can be useful in both human therapeutics, pre-clinical, and veterinary applications. In some embodiments, the subject is a mammal, and in some embodiments, the subject is human. Other mammals include, and are not limited to, apes, chimpanzees, orangutans, monkeys; domesticated animals (pets) such as dogs, cats, guinea pigs, hamsters, mice, rats, rabbits, and ferrets; domesticated farm animals such as cows, buffalo, bison, horses, donkey, swine, sheep, and goats; or exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, pandas, giant pandas, hyena, seals, sea lions, and elephant seals.

The terms "administer", "administered", "administers" and "administering" are defined as the providing a composition to a subject via a route known in the art, including but not limited to intravenous, intraarterial, oral, parenteral, buccal, topical, transdermal, rectal, intramuscular, subcutaneous, intraosseous, transmucosal, or intraperitoneal routes of administration. In certain embodiments of the subject application, oral routes of administering a composition may be preferred.

As used herein, "agent" or "biologically active agent" refers to a biological, pharmaceutical, or chemical compound or other moiety. Non-limiting examples include simple or complex organic or inorganic molecule, a peptide, a protein, a peptide nucleic acid (PNA), an oligonucleotide (including e.g., aptomer and polynucleotides), an antibody, an antibody derivative, antibody fragment, a vitamin derivative, a carbohydrate, a toxin, or a chemotherapeutic compound. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like. A skilled artisan can readily recognize that there is no limit as to the structural nature of the agents of the present invention.

The term "effective amount" or "therapeutically effective amount" refers to that amount of a compound described herein that is sufficient to effect the intended application including but not limited to disease treatment, as defined below. The therapeutically effective amount may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of proliferation or down regulation of activity of a target protein. The specific dose will vary depending on the particular compounds chosen, the dosing regimen to be followed, whether it is administered in combination with other compounds, timing of administration, the tissue to which it is administered, and the physical delivery system in which it is carried.

The term "energy metabolism," as used herein, refers to the transformation of energy that accompanies biochemical reactions in the body, including cellular metabolism and mitochondrial biogenesis. Energy metabolism can be quantified using the various measurements described herein, for example and without limitations, weight-loss, fat-loss, insulin sensitivity, fatty acid oxidation, glucose utilization, triglyceride content, Sirt 1 expression level, AMPK expression level, oxidative stress, and mitochondrial biomass.

The term "isolated", as applied to the subject components, for example a PDE 5 inhibitor, including but not limited to sildenafil and icariin, leucine and leucine metabolites (such as HMB), and resveratrol, refers to a preparation of the substance devoid of at least some of the other components that may also be present where the substance or a similar substance naturally occurs or is initially obtained from. Thus, for example, an isolated substance may be prepared by using a purification technique to enrich it from a source mixture. Enrichment can be measured on an absolute basis, such as weight per volume of solution, or it can be measured in relation to a second, potentially interfering substance present in the source mixture. Increasing enrichment of the embodiments of this invention are increasingly more preferred. Thus, for example, a 2-fold enrichment is preferred, 10-fold enrichment is more preferred, 100-fold enrichment is more preferred, 1000-fold enrichment is even more preferred. A substance can also be provided in an isolated state by a process of artificial assembly, such as by chemical synthesis.

A "modulator" of a pathway refers to a substance or agent which modulates the activity of one or more cellular proteins mapped to the same specific signal transduction pathway. A modulator may augment or suppress the activity and/or expression level or pattern of a signaling molecule. A modulator can activate a component in a pathway by directly binding to the component. A modulator can also indirectly activate a component in a pathway by interacting with one or more associated components. The output of the pathway can be measured in terms of the expression or activity level of proteins. The expression level of a protein in a pathway can be reflected by levels of corresponding mRNA or related transcription factors as well as the level of the protein in a subcellular location. For instance, certain proteins are activated by translocating in or out of a specific subcellular component, including but not limited to nucleus, mitochondria, endosome, lysosome or other membraneous structure of a cell. The output of the pathway can also be measured in terms of physiological effects, such as mitochondrial biogenesis, fatty acid oxidation, or glucose uptake.

An "activator" refers to a modulator that influences a pathway in a manner that increases the pathway output. Activation of a particular target may be direct (e.g. by interaction with the target) or indirect (e.g. by interaction with a protein upstream of the target in a signaling pathway including the target).

The term "selective inhibition" or "selectively inhibit" as referred to a biologically active agent refers to the agent's ability to preferentially reduce the target signaling activity as compared to off-target signaling activity, via direct or interact interaction with the target.

A "suppressor" can be a modulator that influences a pathway in a manner that decreases pathway output.

The term "substantially free", as used herein, refers to compositions that have less than about 10%, less than about 5%, less than about 1%, less than about 0.5%, less than 0.1% or even less of a specified component. For example a composition that is substantially free of non-branched chain amino acids may have less than about 1% of the non-branched chain amino acid lysine. For example, substantially free of a non-branched chain amino acid can be evidenced by less than 1% of the non-branched chain amino acid when compared to the rest of the amino acids is a given composition.

A "sub-therapeutic amount" of an agent, an activator or a therapy is an amount less than the effective amount for that agent, activator or therapy, but when combined with an effective or sub-therapeutic amount of another agent or therapy can produce a desired result, due to, for example, synergy in the resulting efficacious effects, and/or reduced side effects.

A "synergistic" or "synergizing" effect can be such that the one or more effects of the combination compositions are greater than the one or more effects of each component alone at a comparable dosing level, or they can be greater than the predicted sum of the effects of all of the components at a comparable dosing level, assuming that each component acts independently. The synergistic effect can be about, or greater than about 10, 20, 30, 50, 75, 100, 110, 120, 150, 200, 250, 350, or 500% or even more than the effect on a subject with one of the components alone, or the additive effects as measured when each of the components when administered individually. The effect can be any of the measurable effects described herein.

The terms "free amino acid form" or "individual amino acid form", as used herein, can refer to amino acids that are not bound to other amino acids, for example, by peptide bonds. For example, "free" or "individual" leucine refers to leucine not bound to other amino acids by peptide bonds.

Compositions

The subject compositions can include selective phosphodiesterase (PDE) inhibitors. The PDE inhibitors can have a selectivity against one or more PDE enzymes or targets. For example, the PDE inhibitors can be a PDE 1, 2, 3, 4, 5, 6, 9, or 11 selective inhibitor. The sirtuin pathway includes, without limitation, signaling molecules such as, Sirt1, Sirt3, and AMPK. The PDE inhibitor can be combined with another component that provides for a synergistic effect, for example, the PDE inhibitor can be combined with leucine and/or metabolites thereof. In some embodiments, the compositions can include a PDE 5 inhibitor, such as sildenafil or icariin, and leucine and/or a metabolite thereof, such as hydroxymethylbutyrate (HMB).

The invention provides for compositions that can increase or modulate the output of a sirtuin pathway. The output of the pathway can be determined by the expression level and/or the activity of the pathway and/or a physiological effect. In some embodiments, activation of the Sirt1 pathway includes stimulation of PGC1-α and/or subsequent stimulation of mitochondrial biogenesis and fatty acid oxidation. In general, a sirtuin pathway activator is compound that activates or increases one or more components of a sirtuin pathway. An increase or activation of a sirtuin pathway can be observed by an increase in the activity of a pathway component protein. For example, the protein can be Sirt1, PGC1-α, AMPK, Epac1, Adenylyl cyclase, Sirt3, or any other proteins and their respective associated proteins along the signaling pathway depicted in FIG. 1 (Park et. al., "Resveratrol Ameliorates Aging-Related Metabolic Phenotypes by Inhibiting cAMP Phosphodiesterases," Cell 148, 421-433 Feb. 3, 2012). Non-limiting examples of physiological effects that can serve as measures of sirtuin pathway output include mitochondrial biogenesis, mitochondrial biomass, fatty acid oxidation, glucose uptake, nitric oxide production, palmitate uptake, oxygen consumption, carbon dioxide production, weight loss, heat production, visceral adipose tissue loss, respiratory exchange ratio, insulin sensitivity, inflammation marker level, vasodilation, browning of fat cells, and irisin production. Examples of indicia of browning of fat cells include, without limitation, increased fatty acid oxidation, and expression of one or more brown-fat-selective genes (e.g. Ucp1, Cidea, Prdm16, and Ndufs1). In some embodiments, changes in one or more physiological effects that can serve as measures of sirtuin pathway output are induced by increasing irisin production, such as by administering a composition of the invention.

An increase in mitochondrial biogenesis can be evidenced by an increase in the formation of new mitochondria, an increase in mitochondrial biomass and/or by an increase in mitochondrial functions, such as increased fatty acid oxidation, increased heat generation, increased insulin sensitivity, increased in glucose uptake, increased in vasodilation, decreased in weight, decreased in adipose volume, and decreased inflammatory response or markers in a subject.

The compositions can be combination compositions which may include one or more synergistic components. The composition comprising a plurality of components can be such that the synergistic effect is an enhancement in cellular metabolism, and that cellular metabolism is increased to a greater degree as compared to the sum of the effects of administering each component, determined as if each component exerted its effect independently, also referred to as the predicted additive effect herein. For example, if a composition comprising component (a) yields an effect of a 20% improvement in cellular metabolism and a composition comprising component (b) yields an effect of 50% improvement in cellular composition, then a composition comprising both component (a) and component (b) would have a synergistic effect if the combination composition's effect on cellular metabolism is greater than 70%.

A synergistic combination composition can have an effect that is greater than the predicted additive effect of administering each component of the combination composition alone as if each component exerted its effect independently. For example, if the predicted additive effect is 70%, an actual effect of 140% is 70% greater than the predicted additive effect or is 1 fold greater than the predicted additive effect. The synergistic effect can be at least about 20, 50, 75, 90, 100, 150, 200 or 300% greater than the predicted additive effect. Alternatively, the synergistic effect can be at least about 0.2, 0.5, 0.9, 1.1, 1.5, 1.7, 2, or 3 fold greater than the predicted additive effect.

In some embodiments, the synergistic effect of the combination compositions can allow for reduced dosing amounts, leading to reduced side effects to the subject and reduced cost of treatment. In other embodiments, the synergistic effect can allow for results that are not achievable through any other conventional treatments. The subject combination compositions provide a significant improvement in the regulation of energy metabolism.

In some embodiments, the compositions can be combination compositions of one or more branched chain amino acids and/or metabolites thereof and a sirtuin-pathway activator can have one or more characteristics. The one or more branched amino acids may be in free amino acid form. The combination compositions (a) can have a synergistic effect in increasing the sirtuin-pathway output, (b) increase sirtuin-pathway output by at least about 1, 2, 5, 7, 10, or 20 fold, (c) have a molar ratio of branched chain amino acids and/or metabolites thereof to sirtuin-pathway output that is greater than about 20, (d) be formulated as a unit dosage for oral ingestion, where the sirtuin-pathway activator is a substantially homogeneous population of polyphenol molecules, and (e) can have a synergistic effect and further comprise a food carrier. Any of the compositions described herein can have one or more of these characteristics. Examples of sirtuin-pathway activators used in combination with one or more branched chain amino acids are described in U.S. patent application Ser. Nos. 13/549,381 and 13/549,399, which are each incorporated by referenced in their entirety.

In some embodiments, the present invention provides a composition comprising (a) one or more types of branched amino acids and/or metabolites thereof and (b) a selective PDE inhibitor present in a sub-therapeutic amount, wherein the composition is synergistically effective in increasing the sirtuin-pathway output by at least about 5, 10, 50, 100, 200, 500 or more fold as compared to that of component (a) or (b) when used alone. Branched chain amino acids in the composition may be in free amino acid form.

Phosphodiesterase Inhibitors

In some embodiments, the sirtuin pathway activator modulates the activity of phosphodiesterase (PDE). The sirtuin pathway activator can modulate the activity of PDE as a PDE inhibitor. The PDE inhibitor can be selective or non-selective. The PDE inhibitor can exhibit selective inhibition to a PDE subclass, for example PDE 5. Examples of selective PDE inhibitors include inhibitors to PDE 1, 2, 3, 4, 5, 6, 7, 8, 9, 10, or 11. A non-selective PDE inhibitor can be one that does not distinguish among sub-classes of phosphodiesterases. In addition, some non-selective PDE inhibitors may interact with more than one metabolic pathway. For examine, some non-selective PDE inhibitors may be xanthine derivatives and serve as adenosine antagonists and have unknown interactions with other metabolic pathways.

Selective PDE inhibitors can be PDE inhibitors that exhibit preferential interaction with a selected PDE. For example, a PDE inhibitor can have a strong interaction with PDE 5, and very little interaction with other PDE sub-classes.

Any agents that selectively and negatively regulate a PDE subclass, such as PDE 5, expression or activity can be used as selective PDE inhibitors in the compositions and methods of the invention.

For example, a selective PDE inhibitor alternatively can be an agent that exhibits a 50% inhibitory concentration (IC50) with respect to a PDE subclass, such as PDE 5, that is at least at least 10-fold, at least 20-fold, at least 50-fold, at least 100-fold, at least 1000-fold, at least 10,000-fold lower than the inhibitor's IC50 with respect to one, two, three, or more other PDE subclasses. In some embodiment, a selective PDE inhibitor can be an agent that exhibits a 50% inhibitory concentration (IC50) with respect to a PDE subclass, such as PDE 5, that is at least at least 10-fold, at least 20-fold, at least 50-fold, at least 100-fold, at least 1000-fold, at least 10,000-fold, or more, lower than the inhibitor's IC50 with respect to all other PDE subclasses.

In one aspect, IC50 is a determination of the concentration at which 50% of a given PDE is inhibited in a cell-based assay. IC50 determinations can be accomplished using any conventional techniques known in the art. In general, an IC50 can be determined by measuring the activity of a given enzyme in the presence of a range of concentrations of the inhibitor under study. The experimentally obtained values of enzyme activity then are plotted against the inhibitor concentrations used. The concentration of the inhibitor that shows 50% enzyme activity (as compared to the activity in the absence of any inhibitor) is taken as the "IC50" value. Analogously, other inhibitory concentrations can be defined through appropriate determinations of activity. For example, in some settings it can be desirable to establish a 90% inhibitory concentration, i.e., IC90, etc.

Methods for measuring selectivity of PDE inhibitors are described in "Phosphodiesterase-5 Gln-817 is critical for cGMP, vardenafil, or sildenafil affinity: its orientation impacts cGMP but not cAMP affinity" by Zoraghi (2006) and "Cyclic Nucleotide Phosphodiesterases: Molecular Regulation to Clinical Use" by Bender (2006) which are incorporated herein in its entirety by reference.

The subject biologically active agent may inhibit PDE activity with an IC50 value of about 100 nM or less, preferably about 50 nM, about 25 nM, about 10 nM, about 5 nM, about 1 nM, 100 pM, 50 pM, 25 pM, 10 pM, 1 pM, or less, as ascertained in a cell-based assay or an in vitro kinase assay.

In some embodiments, the sirtuin pathway activator is a PDE 1 inhibitor such as nimodipine, vinopocetine, and IC224. The PDE 1 inhibitor can interact with PDE 1, which is a Ca2+/calmodulin-regulated phosphodiesterase that serves to degrade both cAMP and cGMP. The vinopocetine can be derived from periwinkle extract, and it can serve as a cerebrovascularvasodilator. Vinopocetine can be in the form of a dietary supplement.

In other embodiments, the sirtuin pathway activator is a PDE 3 inhibitor such as meribendan, arinone and cilostamide. The sirtuin pathway activator can be a PDE 4 inhibitor, such as apremilast, mesembrine, ibudilast, piclamilast, luteolin, roflumilast, cilomilast, diazepam, rolipram and YM796. The sirtuin pathway activator can be a PDE 4 inhibitor, such as rolipram and YM796. The PDE 4 inhibitor can interact with PDE 4, which is a cAMP-specific phosphodiesterase that predominates in immune cells.

In some embodiments, the sirtuin pathway activator is a PDE 5 inhibitor such as avanafil, iodenafil, mirodenafil, sildenafil, tadalafil, icariin, vardenafil, udenafil, or zaprinst. In other embodiments the sirtuin pathway activator is sildenafil or icariin. The PDE 5 inhibitor can interact with PDE 5, which is a cGMP-specific PDE. Increases in cGMP signaling can increase mitochondrial biogenesis both in vitro and in vivo. A PDE 5 inhibitor can increase nitric oxide signaling and be an effective vasodilator. Examples of PDE 5 inhibitors are described in U.S. Pat. Nos. 5,250,534 and 6,469,012, which are each incorporated by reference in their entirety.

In some embodiments, the sirtuin pathway activator can be a selective PDE inhibitor. In other embodiments, the sirtuin pathway activator is a non-selective PDE inhibitor. PDE inhibitors can be naturally occurring or non-naturally occurring (e.g. manufactured), and may be provided in the form of a natural source comprising the PDE inhibitor, or an extract thereof (e.g. purified). Examples of non-selective PDE inhibitors include, but are not limited to, caffeine, theophylline, theobromine, 3-isobutyl-1-methylxanthine (IBMX), pentoxifylline (3,7-dihydro-3,7-dimethyl-1-(5oxohexyl)-1H-purine-2,6-dione), aminophylline, paraxanthine, and salts, derivatives, metabolites, catabolites, anabolites, precursors, and analogs thereof. Non-limiting examples of natural sources of PDE inhibitors include coffee, tea, guarana, yerba mate, cocoa, and chocolate (e.g. dark chocolate).

Additional Sirtuin Pathway Activators

In some embodiments, a polyphenol, such as resveratrol, or another sirtuin pathway activator is administered in place of or in addition to a PDE-5 inhibitor. In some embodiments, compositions comprising one or more components described herein comprise a PDE inhibitor in place of or in addition to resveratrol or other sirtuin pathway activator. Typically, a PDE inhibitor is provided in an amount that is synergistic with one or more other components of a composition or method of treatment.

The polyphenol can be a stilbene or a hydroxycinnamic acid. In some embodiments, the sirtuin-pathway activator or AMPK pathway activator can be a polyphenol. For example, the polyphenol can be chlorogenic acid, resveratrol, caffeic acid, piceatannol, ellagic acid, epigallocatechin gallate (EGCG), grape seed extract, or any analog thereof. In some embodiments, the activator can be resveratrol, an analog thereof, or a metabolite thereof. For example, the activator can be pterostilbene or a small molecule analog of resveratrol. Examples of small molecule analogs of resveratrol are described in U.S. Patent Application Nos. 20070014833, 20090163476, and 20090105246, which are incorporated herein by reference in its entirety.

The polyphenol can be a substantially homogeneous population of polyphenols. The polyphenol can be one type of polyphenol, wherein the composition can exclude all other types of polyphenols. In other embodiments, the composition can comprise two, three, or four types of polyphenols, and exclude all other types of polyphenols. In some embodiments, the composition can comprise 1, 2, 3, or 4 types of polyphenols and less than 0.1, 0.5, 1, or 2% of any other types of polyphenols.

In various other embodiments, compositions are formulated such that they do not contain (or exclude) one or more of the following ingredients: caffeine, green tea extract or extracts from guarana seed or guarana plants.

In other embodiments, the sirtuin-pathway activator or AMPK pathway activator can be irisin, quinic acid, cinnamic acid, ferulic acid, fucoxanthin, a biguanide (such as metformin), rosiglitazone, or any analog thereof. Alternatively the sirtuin-pathway activator or AMPK pathway activator can be isoflavones, pyroloquinoline (PQQ), quercetin, L-carnitine, lipoic acid, coenzyme Q10, pyruvate, 5-aminoimidazole-4-carboxamide ribotide (ALCAR), bezfibrate, oltipraz, and/or genistein. In some embodiments, the sirtuin pathway activator is a PDE inhibitor.

In some embodiments, the composition can comprise a selective PDE-5 inhibitor in combination of one or more the following: metformin, resveratrol, and a branched chain amino acid or metabolite thereof (e.g. level of HMB).

In some embodiments, the composition can comprise synergistic combinations of sirtuin pathway activators. For example, a composition can comprise synergistic amounts of metformin and a PDE inhibitor. In some embodiments, the composition comprises metformin and caffeine.

In some embodiments, the sirtuin-pathway activator that can be combined with a PDE-5 inhibitor include an agent that stimulates the expression of the Fndc5, PGC1-α, or UCP1. The expression can be measured in terms of the gene or protein expression level. Alternatively, the sirtuin pathway activator can be irisin. Methods for increasing the level of irisin are described in Bostrom et al., "A PGC1-α-dependent myokine that drives brown-fat-like development of white fat and thermogenesis," Nature, Jan. 11, 2012.

In some embodiments, the sirtuin-pathway activator that can be so combined is a flavones or chalcone. In one embodiment, exemplary sirtuin activators are those described in Howitz et al. (2003) Nature 425: 191 and include, for example, resveratrol (3,5,4'-Trihydroxy-trans-stilbene), butein (3,4,2',4'-Tetrahydroxychalcone), piceatannol (3,5,3',4'-Tetrahydroxy-trans-stilbene), isoliquiritigenin (4,2',4'-Trihydroxychalcone), fisetin (3,7,3',4'-Tetrahydroxyflavone), quercetin (3,5,7,3',4'-Pentahydroxyflavone), Deoxyrhapontin (3,5-Dihydroxy-4'-methoxystilbene 3-O-β-D-glucoside); trans-Stilbene; Rhapontin (3,3',5-Trihydroxy-4'-methoxystilbene 3-O-β-D-glucoside); cis-Stilbene; Butein (3,4,2',4'-Tetrahydroxychalcone); 3,4,2'4'6'-Pentahydroxychalcone; Chalcone; 7,8,3',4'-Tetrahydroxyflavone; 3,6,2',3'-Tetrahydroxyflavone; 4'-Hydroxyflavone; 5,4'-Dihydroxyflavone 5,7-Dihydroxyflavone; Morin (3,5,7,2',4'-Pentahydroxyflavone); Flavone; 5-Hydroxyflavone; (−)-Epicatechin (Hydroxy Sites: 3,5,7,3',4'); (−)-Catechin (Hydroxy Sites: 3,5,7,3',4'); (−)-Gallocatechin (Hydroxy Sites: 3,5,7,3',4',5') (+)-Catechin (Hydroxy Sites: 3,5,7,3',4'); 5,7,3',4',5'-pentahydroxyflavone; Luteolin (5,7,3',4'-Tetrahydroxyflavone); 3,6,3',4'-Tetrahydroxyflavone; 7,3',4',5'-Tetrahydroxyflavone; Kaempferol (3,5,7,4'-Tetrahydroxyflavone); 6-Hydroxyapigenin (5,6,7,4'-Tetrahydoxyflavone); Scutellarein); Apigenin (5,7,4'-Trihydroxyflavone); 3,6,2',4'-Tetrahydroxyflavone; 7,4'-Dihydroxyflavone; Daidzein (7,4'-Dihydroxyisoflavone); Genistein (5,7,4'-Trihydroxyflavanone); Naringenin (5,7,4'-Trihydroxyflavanone); 3,5,7,3',4'-Pentahydroxyflavanone; Flavanone; Pelargonidin chloride (3,5,7,4'-Tetrahydroxyflavylium chloride); Hinokitiol (b-Thujaplicin; 2-hydroxy-4-isopropyl-2,4,6-cycloheptatrien-1-one); L-(+)-Ergothioneine ((S)-a-Carboxy-2,3-dihydro-N,N,N-trimethyl-2-thioxo-1H-imidazole-4-ethanaminium inner salt); Caffeic Acid Phenyl Ester; MCI-186 (3-Methyl-1-phenyl-2-pyrazolin-5-one); HBED (N,N'-Di-(2-hydroxybenzyl) ethylenediamine-N,N'-diacetic acid-$H_2O$); Ambroxol (trans-4-(2-Amino-3,5-dibromobenzylamino) cyclohexane-HCl; and U-83836E ((−)-2-((4-(2,6-di-1-Pyrrolidinyl-4-pyrimidinyl)-1-piperazinyl)methyl)-3,4-dihydro-2,5,7,8-tetramethyl-2H-1-benzopyran-6-ol.2HCl). Analogs and derivatives thereof can also be used.

The subject application provides compositions useful for inducing an increase in fatty acid oxidation and mitochondrial biogenesis in a subject. Such compositions contain: HMB in combination with resveratrol; leucine in combination with resveratrol; both leucine and HMB in combination with resveratrol; KIC in combination with resveratrol; both KIC and HMB in combination with resveratrol; both KIC and leucine in combination with resveratrol; or KIC, HMB and leucine in combination with resveratrol.

Branched Chain Amino Acids

Branched chain amino acids that can be combined with a PDE-5 inhibitor have aliphatic side chains with a branch carbon atom that is bound to two or more other atoms. The other atoms may be carbon atoms. Examples of branched chain amino acids include leucine, isoleucine, and valine. Branched chain amino acids may also include other compounds, such as 4-hydroxyisoleucine. In some embodiments, the compositions are substantially free of one or more, or all of non-branched chain amino acids. In some embodiments, the compositions are substantially free of one or more, or all of non-branched chain amino acids in free amino acid form. For example, the compositions can be substantially free of alanine, arginine, asparagine, aspartic acid, cysteine, glutamic acid, glutamine, glycine, histidine, lysine, methionine, phenylalanine, proline, serine, threonine, tryptophan, and/or tyrosine. The compositions can be substantially free of alanine, arginine, asparagine, aspartic acid, cysteine, glutamic acid, glutamine, glycine, histidine, lysine, methionine, phenylalanine, proline, serine, threonine, tryptophan, and/or tyrosine in free amino acid form. In some embodiments, the branched chain amino acid is leucine. In some embodiments, the compositions may be substantially free of isoleucine and/or valine, which may be in free form. The synergistic effects between leucine and a PDE5 inhibitor, as described herein, are not observed when leucine is substituted with isoleucine and valine. Not wishing to be bound by any particular theory, isoleucine, valine, and leucine compete with each other for transport and/or absorption, and inclusion of isoleucine and valine in a composition would reduce the efficacy of any leucine in the composition. Furthermore, isoleucine and valine each lack substantial ability to activate the sirt signaling pathway, including Sirt1 and/or AMPK.

Branched chain amino acids may be present in the composition in free amino acid form. The composition can be substantially free of alanine, arginine, asparagine, aspartic acid, cysteine, glutamic acid, glutamine, glycine, histidine, isoleucine, lysine, methionine, phenylalanine, proline, serine, threonine, tryptophan, tyrosine, or valine in free amino acid form. In some embodiments, the composition is substantially free of non-branched chain amino acids that are not in free form (e.g., non-branched chain amino acids that have formed peptide bonds with other amino acids)."

Without being limited to theory, ingestion of branched chain amino acids, such as leucine, can stimulate tissue protein synthesis via both mTOR-dependent and -independent pathways, as well as to exert an antiproteolytic effect. These effects predominate in muscle, but also can manifest in other tissues, including adipose tissue. Given the energetic cost of protein synthesis and turnover, leucine may increase fatty acid oxidation and net energy utilization and attenuate adiposity. Indeed, leucine has been reported to exert a thermogenic effect and to augment weight and adipose tissue loss during energy restriction. Also, leucine and leucine-rich diets can favorably modulate inflammatory cytokine patterns in adipocytes and mice.

In some embodiments, any of the compositions described herein can include salts, derivatives, metabolites, catabolites, anabolites, precursors, and analogs of any of the branched chain amino acids. The metabolites can be metabolites of leucine, such as HMB. The metabolites of branched chain amino acids can include hydroxymethylbutyrate (HMB), α-hydroxyisocaproic acid, and keto-isocaproic acid (KIC), keto isovalerate, and keto isocaproate. Non-limiting exemplary anabolites of branched chain amino acids can include glutamate, glutamine, threonine, α-ketobytyrate, α-aceto-α-hydroxy butyrate, α,β-dihydroxy-β-methylvalerate, α-keto-β-methylvalerate, α,β-dihydroxy isovalerate, and α-keto isovalerate.

In certain embodiments of the invention, any of the compositions disclosed herein can be formulated such that they do not contain (or exclude) one or more amino acids selected from the group consisting of lysine, glutamate, proline, arginine, valine, isoleucine, aspartic acid, asparagine, glycine, threonine, serine, phenylalanine, tyrosine, histidine, alanine, tryptophan, methionine, glutamine, taurine, carnitine, cystine and cysteine. In certain embodiments of the invention, any of the compositions disclosed herein can be formulated such that they do not contain (or exclude) one or more free amino acids selected from the group consisting of lysine, glutamate, proline, arginine, valine, isoleucine, aspartic acid, asparagine, glycine, threonine, serine, phenylalanine, tyrosine, histidine, alanine, tryptophan, methionine, glutamine, taurine, carnitine, cystine and cysteine. In some cases, the compositions do not contain any non-branched chain amino acids. In some cases, the compositions do not contain any non-branched chain amino acids in free amino acid form. The mass or molar amount of a non-branched chain amino acid can be less than 0.01, 0.1, 0.5, 1, 2, or 5% of the total composition. The mass or molar amount of a non-branched chain amino acid in free amino acid form can be less than 0.01, 0.1, 0.5, 1, 2, or 5% of the total composition. The mass or molar amount of any branched-chain amino acid or metabolite thereof, aside from leucine or its metabolites can be less than 0.01, 0.1, 0.5, 1, 2, or 5% of the total composition. The mass or molar amount of any branched-chain amino acid in free amino acid form or metabolite thereof, aside from leucine or its metabolites can be less than 0.01, 0.1, 0.5, 1, 2, or 5% of the total composition.

Vitamin B6

In some embodiments, a composition described herein can comprise a PDE 5 inhibitor, leucine and/or a leucine metabolite, and vitamin B6. In other embodiments, a composition can comprise sildenafil, resveratrol, and vitamin B6. The leucine may be in free amino acid form.

Without being limited to any particular theory or mode of action, elevations in the active B6 metabolite (pyridoxal phosphate) can reduce the tone and activity of the adipocyte calcium channel. Intracellular free Ca2+ is a primary regulator of adipocyte fatty acid synthase expression and activity, which can result in a suppression of both the expression and activity of fatty acid synthase, which in turn is one of the rate limiting steps in neutral lipid synthesis in adipocytes.

As used herein, vitamin B6 includes its different forms, including pyridoxine, pyridoxine 5'-phosphate, pyridoxal, pyridoxal phosphate, pyridoxal 5'-phosphate, pyridoxamine, pyridoxamine 5'-phosphate. In other embodiments, vitamin B6 can also include 4-pyridoxic acid, which is a catabolite of the above forms of vitamin B6 that is excreted. The compositions described herein can include any one or more of these forms of vitamin B6.

The active form of vitamin B6 in the body is pyridoxal 5-phosphate, which is a coenzyme for all transamination and some decarboxylation and deamination reactions. Furthermore, pyridoxal 5-phosphate is required as a coenzyme for all transamination reactions which occur in the body (Peterson D L, Martinez-Carrion M. The mechanism of transamination. Function of the histidyl residue at the active site of supernatant aspartate transaminase. J Biol Chem. 1970 Feb. 25; 245(4):806-13).

In some embodiments, any of the compositions described herein can include salts, derivatives, metabolites, catabolites, anabolites, precursors, and analogs of any of the forms of vitamin B6. Exemplary catabolites of vitamin B6 include 2-methyl-3-hydroxy-5-formylpyridine-4-carboxylate and 3-hydroxy-2-methylpyridine-4,5-dicarboxylate. Exemplary analogs of vitamin B6 are described in U.S. Pat. Nos. 7,230,009, and 6,369,042. Exemplary precursors of vitamin B6 are described in U.S. Pat. No. 7,495,101.

Pharmaceutically Active Agents

The subject compositions can further include one or more pharmaceutically active agents other than a PDE-5 inhibitor. Examples of therapeutically active agents include ibuprofen, aldoril, and gemfebrozil, verapamil, maxzide, diclofenac and metrolol, maproltiline, triazolam and minoxidil. For example, the combination compositions can comprise a pharmaceutically active anti-diabetic agent, weight loss agent, or calcium regulation agent. U.S. Pat. No. 7,109,198 and U.S. Patent Application No. 20090142336, which are both incorporated by reference herein, describe a variety of pharmaceutically active agents or therapeutically active agents suitable for inclusion in a combination composition described herein. Examples of anti-diabetic agents include biguanides (such as metformin), thiazoladinediones and meglitinides (such as repaglinide, pioglitazone, and rosiglitazone), alpha glucosidease inhibitors (such as acarbose), sulfonylureas (such as tolbutamide, acetohexamide, tolazamide, chlorpropamide, glipizide, glyburide, glimepiride, gliclazide), incretins, ergot alkaloids (such as bromocriptine), and DPP inhibitors (such as sitagliptin, vildagliptin, saxagliptin, lingliptin, dutogliptin, gemigliptin, alogliptin, and berberine). The anti-diabetic agent can be an oral anti-diabetic agent. The anti-diabetic agent can also be injectable anti-diabetic drugs, including insulin, amylin analogues (such as pramlintide), and inretin mimetics (such as exenatide and liraglutide). Examples of anti-obesity therapeutic agents include lipase inhibitors (such as Orlistat), dopaminergic, noradrenergic, and serotoninergic compounds, cannabinoid receptor antagonists (such as rimonabant), exenatide, pramlintide, and CNS agents (such as topimerate). These examples are provided for discussion purposes only, and are intended to demonstrate the broad scope of applicability of the invention to a wide variety of drugs. It is not meant to limit the scope of the invention in any way.

In some embodiments, a PDE-5 inhibitor can be combined with a pair of pharmaceutically active agents as follow: glipizide and metformin; glyburide and metformin; pioglitazone and glimepiride; pioglitazone and metformin; repaglinide and metformin; rosiglitazone and glimepiride; rosiglitazone and metformin; and sitagliptin and metformin.

The amount of pharmaceutical agent, or any other component used in a combination composition described herein, can be a used in an amount that is therapeutically effective. The amount of pharmaceutical agent, or any other component used in a combination composition described herein, can be a used in an amount that is sub-therapeutic. In some embodiments, using sub-therapeutic amounts of an agent or component can reduce the side-effects of the agent. Use of sub-therapeutic amounts can still be effective, particularly when used in synergy with other agents or components.

A sub-therapeutic amount of the agent or component can be such that it is an amount below which would be considered therapeutic. For example, FDA guidelines can suggest a specified level of dosing to treat a particular condition, and a sub-therapeutic amount would be any level that is below the FDA suggested dosing level. The sub-therapeutic amount can be about 1, 5, 10, 15, 20, 25, 30, 35, 50, 75, 90, or 95% less than the amount that is considered to be a therapeutic amount. The therapeutic amount can be assessed for individual subjects, or for groups of subjects. The group of subjects can be all potential subjects, or subjects having a particular characteristic such as age, weight, race, gender, or physical activity level.

In the case of metformin hydrochloride, the physician suggested starting dose is 1000 mg daily, with subject specific dosing having a range of 500 mg to a maximum of 2500 mg daily (metformin hydrochloride extended-release tablets label www.accessdata.fda.gov/drugsatfda_docs/label/2008/021574s0101bl.pdf). The particular dosing for a subject can be determined by a clinician by titrating the dose and measuring the therapeutic response. The therapeutic dosing level can be determined by measuring fasting plasma glucose levels and measuring glycosylated hemoglobin. A sub-therapeutic amount can be any level that would be below the recommended dosing of metformin. For example, if a subject's therapeutic dosing level is determined to be 700 mg daily, a dose of 600 mg would be a sub-therapeutic amount. Alternatively, a sub-therapeutic amount can be determined relative to a group of subjects rather than an individual subject. For example, if the average therapeutic amount of metformin for subjects with weights over 300 lbs is 2000 mg, then a sub-therapeutic amount can be any amount below 2000 mg. In some embodiments, the dosing can be recommended by a healthcare provider including, but not limited to a patient's physician, nurse, nutritionist, pharmacist, or other health care professional. A health care professional may include a person or entity that is associated with the health care system. Examples of health care professionals may include surgeons, dentists, audiologists, speech pathologists, physicians (including general practitioners and specialists), physician assistants, nurses, midwives, pharmaconomists/pharmacists, dietitians, therapists, psychologists, physical therapists, phlebotomists, occupational therapists, optometrists, chiropractors, clinical officers, emergency medical technicians, paramedics, medical laboratory technicians, radiographers, medical prosthetic technicians social workers, and a wide variety of other human resources trained to provide some type of health care service.

Dosing Amounts

The invention provides for compositions that are combinations of isolated components, such as leucine, metabolites of leucine, such as HMB, sildenafil, icariin, and resveratrol, that have been isolated from one or more sources. The invention provides for compositions that are enriched in leucine, metabolites of leucine, such as HMB, sildenafil, icariin, and/or resveratrol. The components can be isolated from natural sources or created from synthetic sources and then enriched to increase the purity of the components. For example, sildenafil can be created from a synthetic source and then enriched by one or more purification methods. Additionally, leucine (e.g., free leucine), can be isolated from a natural source and then enriched by one or more separations. The isolated and enriched components, such as sildenafil and leucine, can then be combined and formulated for administration to a subject.

In some embodiments, a composition comprises an amount of a selective PDE inhibitor (e.g., PDE-5 inhibitor including but not limited to sildenafil or icariin). The amount of a PDE inhibitor may be a subtherapeutic amount, and/or an amount that is synergistic with one or more other compounds in the composition or one or more of the compounds administered simultaneously or in close temporal proximity with the composition. In some embodiments, the PDE inhibitor is administered in a low dose, a medium dose, or a high dose, which describes the relationship between two doses, and generally do not define any particular dose range.

A daily dose of sildenafil can be about or less than about 0.05, 0.1, 0.5, 1, 2, 5, 10, 20, 40, 60, 80, or 100 mg of sildenafil. In other embodiments, a daily dose of icariin can be about or less than about 1, 10, 20, 50, 100, 150, 300, 400, 500, 750, 1000, 1500, or 2000 mg of icariin. A daily low dose of resveratrol may comprise about, less than about, or more than about 0.5 mg/kg, 1 mg/kg, 2.5 mg/kg, 5 mg/kg, 7.5 mg/kg, 10 mg/kg, 12.5 mg/kg, 15 mg/kg, 20 mg/kg, 25 mg/kg, 50 mg/kg, 75 mg/kg, 100 mg/kg, or more; a daily medium dose of resveratrol may comprise about, less than about, or more than about 20 mg/kg, 25 mg/kg, 50 mg/kg, 75 mg/kg, 100 mg/kg, 125 mg/kg, 150 mg/kg, 175 mg/kg, 200 mg/kg, 250 mg/kg, or more; and a daily high dose of resveratrol may comprise about, less than about, or more than about 150 mg/kg, 175 mg/kg, 200 mg/kg, 225 mg/kg, 250 mg/kg, 300 mg/kg, 350 mg/kg, 400 mg/kg, or more.

Another aspect of the invention provides compositions comprising synergizing amounts of PDE-5 inhibitor, such as sildenafil and icariin, in combination with leucine, HMB, KIC, vitamin D, vitamin K2, and/or resveratrol. These synergizing amounts can be as follows: leucine about, less than about, or more than about 0.5-3.0 g/day (e.g. 0.5, 0.75, 1, 1.25, 1.5, 1.75, 2, 2.5, 3, or more g/day); HMB about, less than about, or more than about 0.20-3.0 g/day (e.g. 0.2, 0.4, 0.5, 0.75, 1, 1.5, 2, 2.5, 3, or more g/day); KIC about, less than about, or more than about 0.2-3.0 g/day (e.g. 0.2, 0.4, 0.5, 0.75, 1, 1.25, 1.5, 1.75, 2, 2.5, 3, or more g/day); vitamin D about, less than about, or more than about 2.5-25 μg/day (e.g. 2.5, 5, 7.5, 10, 12.5, 15, 17.5, 20, 25, or more μg/day); vitamin K2 about, less than about, or more than about 5-200 μg/day (e.g. 5, 10, 25, 50, 75, 100, 150, 200, or more μg/day); sildenafil about, less than about, or more than about 0.05-100 mg/day (e.g., 0.05, 0.1, 0.5, 1, 2, 5, 10, 20, 40, 60, 80, or 100 mg/day); icariin about, less than about, or more than about 1-2000 mg (e.g., 1, 10, 20, 50, 100, 150, 300, 400, 500, 750, 1000, 1500, or 2000 mg/day) and/or resveratrol about, less than about, or more than about 10-500 mg/day (e.g. 10, 25, 50, 51, 75, 100, 150, 200, 250, 300, 350, 400, 450, 500, or more mg/day). Thus, one embodiment provides a composition comprising leucine in an amount of about 0.75 to about 3.0 g (0.75 to 3.0 g) and sildenafil in an amount between about 0.05 and about 100 mg (or 0.05 to 100 mg). Another embodiment provides a composition comprising HMB in an amount of 0.40-3.0 g (or 0.40 to 3.0 g) and sildenafil in an amount between 0.05-100 mg (or 0.050 to 100 mg). Another embodiment provides for a composition comprising leucine in an amount of about 0.75-about 3.0 g (or 0.75 to 3.0 g), HMB in an amount of about 0.40 and about 3.0 g (or 0.40 to 3.0 g) and sildenafil in an amount between about 0.05 and about 100 mg (or 0.05 to 100 mg). In compositions comprising a PDE inhibitor or methods comprising administration of a PDE inhibitor (separately from or concurrently with one or more other components), the PDE inhibitor may be provided in an amount that produces a peak plasma concentration of about, less than about, or more than about 0.1, 1, 5, 10, 25, 50, 100, 500, 1000, 2500, 5000, 10000, or more nM.

Another embodiment provides for a composition containing synergizing amounts of sildenafil and resveratrol, in combination with HMB or leucine. In such compositions, the total amount of leucine and HMB within the composition can be less than 3.0 g (or less than about 3.0 g; e.g. less than about 0.7, 0.75, 1, 1.5, 2, 2.5, 3 grams) and at least 0.70 g (or at least about 0.70 g; e.g. at least about 0.7, 0.75, 1, 1.5, 2, 2.5, 3 grams). Compositions containing both leucine and HMB can contain amounts of leucine and HMB that total about, less than about, or more than about 0.70 g to 3.0 g (about 0.70 g to about 3.0 g; e.g. 0.7, 1, 1.25, 1.5, 1.75, 2, 2.5, 3, or more grams), 0.75 g to 3.0 g (about 0.75 g to about 3.0 g), or 1.0 g to 3.0 g (about 1.0 g to about 3.0 g) within the composition and resveratrol in synergizing amounts (at least 35 mg of resveratrol and no more than 500 (or about 500) mg resveratrol (e.g. about, less than about, or more than about 35, 50, 75, 100, 150, 200, 250, 300, 350, 400, 450, or 500 mg resveratrol) or an amount of resveratrol between 50 and 500 mg (or about 50 to about 500 mg).

In some embodiments a unit dosage can comprise a PDE 5 inhibitor, such as sildenafil, in combination with one or more other components. In some embodiments, a unit dosage comprises one or more of: about, less than about, or more than about can be about or less than about 0.05, 0.1, 0.5, 1, 2, 5, 10, 20, 40, 60, 80, or 100 mg of a selective PDE-5 inhibitor (e.g., sildenafil); about, less than about, or more than about 50, 100, 200, 300, 400, 500 or more mg of HMB; about, less than about, or more than about 10, 20, 30, 40, 50, 75, 100, or more mg resveratrol; about, less than about, or more than about 2.5, 5, 7.5, 10, 12.5, 15, 17.5, 20, or more mg of vitamin B6; about, less than about, or more than about 2.5, 5, 7.5, 10, 12.5, 15, 17.5, 20, 25, or more μg of vitamin D; about, less than about, or more than about 5, 10, 25, 50, 75, 100, 150, 200, or more μg of vitamin K2; and about, less than about, or more than about 400, 500, 600, 700, 800, 900, 1000, 1100, 1250, 1500, or more mg of leucine. A unit dosage can comprise about, less than about, or more than about 500 mg beta hydroxyl, beta methyl butyrate and about, less than about, or more than about 50 mg resveratrol. A unit dosage can comprise about, less than about, or more than about 500 mg beta hydroxy, beta methyl butyrate; and about, less than about, or more than about 50 mg resveratrol; and about, less than about, or more than about 15 mg vitamin B6.

In some embodiments, a unit dosage can comprise between about 0.1-10 mg of sildenafil. In some embodiments, a unit dosage can comprise between about 0.5-100 mg of avanafil, 0.05-20 mg of iodenafil, 0.25-50 mg of mirodenafil, 0.01-2.5 mg of tadalafil, 0.01-2.5 mg of vardenafil, 0.5-100 mg of udenafil, or 0.5-100 mg of zaprinst. In some embodiments, a unit dosage can comprise between about 0.5-50 mg of avanafil, 0.05-10 mg of iodenafil, 0.25-25 mg of mirodenafil, 0.01-1.25 mg of tadalafil, 0.01-1.25 mg of vardenafil, 0.5-50 mg of udenafil, or 0.5-50 mg of zaprinst.

In some embodiments, a unit dosage can comprise chlorogenic acid (e.g. about, less than about, or more than about 25, 50, 75, 100, 150, 200, or mg) in combination with one or more other components in about, less than about, or more than about the indicated amounts. A unit dosage can comprise 500 mg beta hydroxy, beta methyl butyrate (e.g. 50, 100, 200, 300, 400, 500 or more mg) and 100 mg chlorogenic acid. A unit dosage can comprise 500 mg beta hydroxy, beta methyl butyrate (e.g. 50, 100, 200, 300, 400, 500 or more mg); and 100 mg chlorogenic acid; and 15 mg vitamin B6. A unit dosage can comprise 1.125 g leucine (e.g. 400, 500, 600, 700, 800, 900, 1000, 1100, 1250, or more mg) and 100 mg chlorogenic acid. A unit dosage can comprise 1.125 g leucine (e.g. 400, 500, 600, 700, 800, 900, 1000, 1100, 1250, or more mg); 100 mg chlorogenic acid; and 15 mg vitamin B6 (e.g. 2.5, 5, 7.5, 10, 12.5, 15, 17.5, 20, or more mg). A unit dosage can comprise 750 mg leucine, 75 mg chlorogenic acid and 10 mg vitamin B6.

In some embodiments a unit dosage can comprise quinic acid in about, less than about, or more than about the indicated amounts (e.g. 10, 15, 20, 25, 30, 40, 50, or more mg), in combination with one or more other components in about, less than about, or more than about the indicated amounts. A unit dosage can comprise 500 mg beta hydroxy, beta methyl butyrate (e.g. 50, 100, 200, 300, 400, 500 or more mg) and 25 mg quinic acid. A unit dosage can comprise 500 mg beta hydroxy, beta methyl butyrate (e.g. 50, 100, 200, 300, 400, 500 or more mg), 25 mg quinic acid and 15 mg vitamin B6 (e.g. 2.5, 5, 7.5, 10, 12.5, 15, 17.5, 20, or more mg). A unit dosage can comprise 1.125 g leucine (e.g. 400, 500, 600, 700, 800, 900, 1000, 1100, 1250, or more mg) and 25 mg quinic acid. A unit dosage can comprise 1.125 g leucine (e.g. 400, 500, 600, 700, 800, 900, 1000, 1100, 1250, or more mg), 25 mg quinic acid and 15 mg vitamin B6 (e.g. 2.5, 5, 7.5, 10, 12.5, 15, 17.5, 20, or more mg). A unit dosage can comprise 750 mg leucine, 15 mg quinic acid and 10 mg vitamin B6.

In some embodiments a unit dosage can comprise fucoxanthin in about, less than about, or more than about the indicated amounts (e.g. 0.5, 0.75, 1, 1.25, 1.5, 1.75, 2, 2.25, 2.5, 3, 5, or more mg) in combination with one or more other components in about, less than about, or more than about the indicated amounts. A unit dosage can comprise 500 mg beta hydroxy, beta methyl butyrate (e.g. 50, 100, 200, 300, 400, 500 or more mg) and 2.5 mg fucoxanthin. A unit dosage can comprise 500 mg beta hydroxy, beta methyl butyrate (e.g. 50, 100, 200, 300, 400, 500 or more mg), 2.5 mg fucoxanthin and 15 mg vitamin B6 (e.g. 2.5, 5, 7.5, 10, 12.5, 15, 17.5, 20, or more mg). A unit dosage can comprise 1.125 g leucine (e.g. 400, 500, 600, 700, 800, 900, 1000, 1100, 1250, or more mg) and 2.5 mg fucoxanthin. A unit dosage can comprise 1.125 g leucine (e.g. 400, 500, 600, 700, 800, 900, 1000, 1100, 1250, or more mg), 2.5 mg fucoxanthin and 15 mg vitamin B6 (e.g. 2.5, 5, 7.5, 10, 12.5, 15, 17.5, 20, or more mg). A unit dosage can comprise 750 mg leucine, 1.5 mg fucoxanthin and 10 mg vitamin B6.

In some embodiments, a composition comprises an amount of an antidiabetic agent, such as a biguanide (e.g. metformin). The amount of antidiabetic agent may be a subtherapeutic amount, and/or an amount that is synergistic with one or more other compounds in the composition or one or more of the compounds administered simultaneously or in close temporal proximity with the composition. In some embodiments, the antidiabetic agent is administered in a very low dose, a low dose, a medium dose, or a high dose, which describes the relationship between two doses, and generally do not define any particular dose range. For example, a daily very low dose of metformin may comprise about, less than about, or more than about 5 mg/kg, 10 mg/kg, 25 mg/kg, 50 mg/kg, 75 mg/kg, 100 mg/kg, or more; a daily low dose of metformin may comprise about, less than about, or more than about 75 mg/kg, 100 mg/kg, 150 mg/kg, 175 mg/kg, 200 mg/kg, or more; a daily medium dose of metformin may comprise about, less than about, or more than about 150 mg/kg, 175 mg/kg, 200 mg/kg, 250 mg/kg, 300; and a daily high dose of metformin may comprise about, less than about, or more than about 200 mg/kg, 250 mg/kg, 300 mg/kg, 350 mg/kg, 400 mg/kg, 500 mg/kg, 700 mg/kg, or more.

In some embodiments a unit dosage can comprise metformin in about, less than about, or more than about the indicated amounts (e.g. 25, 50, 100, 150, 200, 250, 300, 400, 500, or more mg) in combination with one or more other components in about, less than about, or more than about the indicated amounts (such as 10, 20, 30, 40, 50, 75, 100, or more mg of resveratrol; 50, 100, 200, 300, 400, 500 or more mg HMB; and/or 400, 500, 600, 700, 800, 900, 1000, 1100, 1250, or more mg of leucine). A unit dosage can comprise about, less than about or more than about 50 mg metformin, 500 mg beta hydroxy, beta methyl butyrate and 50 mg resveratrol. A unit dosage can comprise about, less than about or more than about 50 mg metformin, 1.125 g leucine and 50 mg resveratrol. A unit dosage can comprise about, less than about or more than about 100 mg metformin, 500 mg beta hydroxy, beta methyl butyrate and 50 mg resveratrol. A unit dosage can comprise about, less than about or more than about 100 mg metformin, 1.125 g leucine and 50 mg resveratrol. A unit dosage can comprise about, less than about or more than about 250 mg metformin, 500 mg beta hydroxy, beta methyl butyrate and 50 mg resveratrol. A unit dosage can comprise about, less than about or more than about 250 mg metformin, 1.125 g leucine and 50 mg resveratrol. In some embodiments, a composition further comprises a PDE inhibitor in a synergizing amount. In some embodiments, a metformin composition further comprises a selective PDE inhibitor in a synergizing amount.

In some embodiments, a unit dosage comprises leucine and icariin. The unit dosage can comprise about 500 to about 2000 mg of leucine. The unit dosage can comprise about 700 to about 1500 mg of leucine. The unit dosage can comprise about 900 to about 1300 mg of leucine. The weight ratio of icariin relative to leucine can be 0.01-0.1. The weight ratio of icariin relative to leucine can be 0.02-0.06. The weight ratio of icariin relative to leucine can be 0.03-0.05. An exemplary formulation of a unit dosage comprising leucine and icariin is shown in Table 1.

TABLE 1

| Formulation 1 | | |
|---|---|---|
| Component | Mass (mg) | Wt ratio (relative to Leucine) |
| Leucine | 1110 | 1 |
| Icariin | 50 | 0.045 |

In some embodiments, a unit dosage comprises leucine, icariin, and resveratrol. The unit dosage can comprise about 500 to about 2000 mg of leucine. The unit dosage can comprise about 700 to about 1500 mg of leucine. The unit dosage can comprise about 900 to about 1300 mg of leucine. The weight ratio of icariin relative to leucine can be 0.01-0.1. The weight ratio of icariin relative to leucine can be 0.02-0.06. The weight ratio of icariin relative to leucine can be 0.03-0.05. The weight ratio of resveratrol relative to leucine can be 0.01-0.1. The weight ratio of resveratrol relative to leucine can be 0.02-0.06. The weight ratio of resveratrol relative to leucine can be 0.03-0.05. An exemplary formulation of a unit dosage comprising leucine, icariin, and resveratrol is shown in Table 2.

TABLE 2

Formulation 2

| Component | Mass (mg) | Wt ratio (relative to Leucine) |
|---|---|---|
| Leucine | 1110 | 1 |
| Icariin | 50 | 0.045 |
| Resveratrol | 50 | 0.045 |

In some embodiments, a unit dosage comprises leucine, icariin, and metformin. The unit dosage can comprise about 500 to about 2000 mg of leucine. The unit dosage can comprise about 700 to about 1500 mg of leucine. The unit dosage can comprise about 900 to about 1300 mg of leucine. The weight ratio of icariin relative to leucine can be 0.01-0.1. The weight ratio of icariin relative to leucine can be 0.02-0.06. The weight ratio of icariin relative to leucine can be 0.03-0.05. The weight ratio of metformin relative to leucine can be 0.01-0.6. The weight ratio of metformin relative to leucine can be 0.1-0.5. The weight ratio of metformin relative to leucine can be 0.15-0.3. The weight ratio of metformin relative to leucine can be 0.22-0.23. An exemplary formulation of a unit dosage comprising leucine, icariin, and metformin is shown in Table 3.

TABLE 3

Formulation 3

| Component | Mass (mg) | Wt ratio (relative to Leucine) |
|---|---|---|
| Leucine | 1110 | 1 |
| Icariin | 50 | .045 |
| metformin | 250 | .225 |

In some embodiments, a unit dosage comprises leucine and sildenafil. The unit dosage can comprise about 500 to about 2000 mg of leucine. The unit dosage can comprise about 700 to about 1500 mg of leucine. The unit dosage can comprise about 900 to about 1300 mg of leucine. The weight ratio of sildenafil relative to leucine can be 0.00001-0.05. The weight ratio of sildenafil relative to leucine can be 0.0001-0.03. The weight ratio of sildenafil relative to leucine can be 0.001-0.02. The weight ratio of sildenafil relative to leucine can be 0.005-0.015. An exemplary formulation of a unit dosage comprising leucine and sildenafil is shown in Table 4.

TABLE 4

Formulation 4

| Component | Mass (mg) | Wt ratio (relative to Leucine) |
|---|---|---|
| Leucine | 1110 | 1 |
| Sildenafil | 10 | 0.009 |

In some embodiments, a unit dosage comprises leucine, resveratrol, and sildenafil. The unit dosage can comprise about 500 to about 2000 mg of leucine. The unit dosage can comprise about 700 to about 1500 mg of leucine. The unit dosage can comprise about 900-1300 mg of leucine. The weight ratio of resveratrol relative to leucine can be 0.00001-0.05. The weight ratio of resveratrol relative to leucine can be 0.0001-0.03. The weight ratio of resveratrol relative to leucine can be 0.001-0.02. The weight ratio of sildenafil relative to leucine can be 0.00001-0.05. The weight ratio of sildenafil relative to leucine can be 0.0001-0.03. The weight ratio of sildenafil relative to leucine can be 0.001-0.02. The weight ratio of sildenafil relative to leucine can be 0.005-0.015. An exemplary formulation of a unit dosage comprising leucine, resveratrol, and sildenafil is shown in Table 5.

TABLE 5

Formulation 5

| Component | Mass (mg) | Wt ratio (relative to Leucine) |
|---|---|---|
| Leucine | 1110 | 1 |
| Resveratrol | 10 | 0.009 |
| Sildenafil | 10 | 0.009 |

In some embodiments, a unit dosage comprises HMB and icariin. The unit dosage can comprise about 50-1000 mg of HMB. The unit dosage can comprise about 100-500 mg of HMB. The unit dosage can comprise 150-400 mg of HMB. The unit dosage can comprise 200-300 mg of HMB. The weight ratio of icariin relative to HMB can be 0.05-0.5. The weight ratio of icariin relative to HMB can be 0.07-0.4. The weight ratio of icariin relative to HMB can be 0.1-0.3. An exemplary formulation of a unit dosage comprising HMB and icariin is shown in Table 6.

TABLE 6

Formulation 6

| Component | Mass (mg) | Wt ratio (relative to HMB) |
|---|---|---|
| HMB | 250 | 1 |
| Icariin | 50 | 0.2 |

In some embodiments, a unit dosage comprises HMB, icariin, and resveratrol. The unit dosage can comprise about 50-1000 mg of HMB. The unit dosage can comprise about 100-500 mg of HMB. The unit dosage can comprise about 150-400 mg of HMB. The unit dosage can comprise 200-300 mg of HMB. The weight ratio of icariin relative to HMB can be 0.05-0.5. The weight ratio of icariin relative to HMB can be 0.07-0.4. The weight ratio of icariin relative to HMB can be 0.1-0.3. The weight ratio of resveratrol relative to HMB can be 0.05-0.5. The weight ratio of resveratrol relative to HMB can be 0.07-0.4. The weight ratio of resveratrol relative to HMB can be 0.1-0.3. An exemplary formulation of a unit dosage comprising HMB, icariin, and resveratrol is shown in Table 7.

TABLE 7

Formulation 7

| Component | Mass (mg) | Wt ratio (relative to HMB) |
|---|---|---|
| HMB | 250 | 1 |
| Icariin | 50 | 0.2 |
| Resveratrol | 50 | 0.2 |

In some embodiments, a unit dosage comprises HMB, icariin, and metformin. The unit dosage can comprise about 50 to about 1000 mg of HMB. The unit dosage can comprise about 100 to about 500 mg of HMB. The unit dosage can comprise about 150 to about 400 mg of HMB. The unit dosage can comprise about 200 to about 300 mg of HMB. The weight ratio of icariin relative to HMB can be 0.05-0.5. The weight ratio of icariin relative to HMB can be 0.07-0.4. The weight ratio of icariin relative to HMB can be 0.1-0.3. The weight ratio of metformin relative to HMB can be 0.2-4. The weight ratio of metformin relative to HMB can be 0.5-2. The weight ratio of metformin relative to HMB can be 0.75-1.25. An exemplary formulation of a unit dosage comprising HMB, icariin, and metformin is shown in Table 8.

TABLE 8

Formulation 8

| Component | Mass (mg) | Wt ratio (relative to HMB) |
|---|---|---|
| HMB | 250 | 1 |
| Icariin | 50 | 0.2 |
| Metformin | 250 | 1 |

In some embodiments, a unit dosage comprises HMB and sildenafil. The unit dosage can comprise about 50-1000 mg of HMB. The unit dosage can comprise about 100-500 mg of HMB. The unit dosage can comprise about 150-400 mg of HMB. The unit dosage can comprise 200-300 mg of HMB. The weight ratio of sildenafil relative to HMB can be 0.01-0.1. The weight ratio of sildenafil relative to HMB can be 0.02-0.08. The weight ratio of sildenafil relative to HMB can be 0.03-0.05. An exemplary formulation of a unit dosage comprising HMB and sildenafil is shown in Table 9.

TABLE 9

Formulation 9

| Component | Mass (mg) | Wt ratio (relative to HMB) |
|---|---|---|
| HMB | 250 | 1 |
| Sildenafil | 10 | 0.04 |

In some embodiments, a unit dosage comprises HMB, sildenafil, and resveratrol. The unit dosage can comprise about 50-1000 mg of HMB. The unit dosage can comprise about 100-500 mg of HMB. The unit dosage can comprise about 150-400 mg of HMB. The unit dosage can comprise 200-300 mg of HMB. The weight ratio of sildenafil relative to HMB can be 0.01-0.1. The weight ratio of sildenafil relative to HMB can be 0.02-0.08. The weight ratio of sildenafil relative to HMB can be 0.03-0.05. The weight ratio of resveratrol relative to HMB can be 0.01-0.1. The weight ratio of resveratrol relative to HMB can be 0.02-0.08. The weight ratio of resveratrol relative to HMB can be 0.03-0.05. An exemplary formulation of a unit dosage comprising HMB and sildenafil is shown in Table 10.

TABLE 10

Formulation 10

| Component | Mass (mg) | Wt ratio (relative to HMB) |
|---|---|---|
| HMB | 250 | 1 |
| Sildenafil | 10 | 0.04 |
| Resveratrol | 10 | 0.04 |

In some embodiments, any of the unit dosages herein, e.g., described in Tables 1-10 further comprise Vitamin B6. In some embodiments, any of the unit dosages herein, e.g., described in Tables 1-10 further comprise 15 mg of Vitamin B6. The unit dosages can further comprise about 5-50 mg of Vitamin B6. The weight ratio of Vitamin B6 to HMB, if present, can be about 0.06, 0.002-0.18, 0.03-0.12, or 0.05-0.07. The weight ratio of Vitamin B6 to Leucine, if present, can be about 0.0135, 0.005-0.03, 0.007-0.025, or 0.01-0.017.

In some embodiments, the compositions described herein can be substantially free of one or more specified components or have specified levels of such components. The compositions, for example the compositions described in Tables 1-10, can be substantially free, or comprise less than 40, 20, 10, 15, 5, or 1% by total weight, of glycemic carbohydrates. The compositions can be substantially free, or comprise less than 40, 20, 10, 15, 5, or 1% by total weight, of sugars, including, without limitation, glucose, dextrose, fructose and sucrose. The compositions can be substantially free, or comprise less than 40, 20, 10, 15, 5, or 1% by total weight, of high glycemic index carbohydrates. The compositions can be substantially free, or comprise less than 40, 20, 10, 15, 5, or 1% by total weight, of complex carbohydrates. The compositions can be substantially free, or comprise less than 40, 20, 10, 15, 5, or 1% by total weight, of simple carbohydrates. The compositions can be substantially free, or comprise less than 40, 20, 10, 15, 5, or 1% by total weight, of starch, corn syrup, short grain white rice, white flour.

In some embodiments of the invention, the combination compositions can have a specified ratio of branched chain amino acids and/or metabolites thereof to a selective PDE inhibitor. The specified ratio can provide for effective and/or synergistic regulation of energy metabolism. For example, the specified ratio can cause a decrease in weight gain of a subject, a decrease in visceral adipose volume of a subject, an increase in fat oxidation of a subject, an increase in insulin sensitivity of a subject, an increase of glucose uptake in muscle of a subject, a decrease in inflammation markers, an increase in vasodilatation, and/or an increase in body temperature. Such beneficial effects can result from, in part, an increase in mitochondrial biogenesis, or a variety of other changes in the energy metabolism pathway. The ratio of branched chain amino acids and/or metabolites thereof to a selective PDE inhibitor activator can be a mass ratio, a molar ratio, or a volume ratio.

In some embodiments, the molar ratio of (a) branched chain amino acids and/or metabolites thereof to (b) a selective PDE inhibitor about or greater than about 20, 25, 30, 35, 40, 45, 50, 55, 60, 65, 70, 75, 80, 85, 90, 100, 120, or 150. In other embodiments, the molar ratio of one or more branched chain amino acids and/or metabolites thereof to a selective PDE inhibitor contained in the subject compositions is about or greater than about 20, 30, 40, 50, 60, 70, 80, 90, 95, 90, 95, 100, 105, 110, 120, 130, 140, 150, 160, 170, 180, 190, 200, 220, 250, 300, 350, 400, or 500. In some embodiments, the molar ratio of component (a) to (b) in said composition is greater than about 20, 40, 60, 80, 100, 120, or 150. In some embodiments, the molar ratio of component (a) to (b) in said composition is greater than about 80, 100, 120, or 150. In some embodiments, the molar ratio of component (a) to (b) in said composition is greater than about 80, 100, 120, or 150. In some embodiments, the molar ratio of component (a) to (b) in said composition is greater than about 200, 250, or 300. In some embodiments, the molar ratio of component (a) to (b) in said composition is greater than about 40, 150, 250, or 500.

In some embodiments, the dosing of leucine, any metabolites of leucine, the PDE inhibitor (such as a PDE 5 inhibitor like sildenafil) can be designed to achieve a specified physiological concentration or circulating level of leucine, metabolites of leucine and/or a PDE 5 inhibitor. The physiological concentration can be a circulating level as measured in the blood stream of a subject. The subject can be a human or an animal. A selected dosing can be altered based on the characteristics of the subject, such as weight, rate of energy metabolism, genetics, ethnicity, height, or any other characteristic. The amount of leucine in a unit dose can be such that the circulating level of leucine in a subject is about or greater than about 0.25 mM, 0.5 mM, 0.75 mM, or 1 mM. A dosing of about 1,125 mg leucine (e.g., free leucine), can achieve a circulating level of leucine in a subject that is about 0.5 mM. A dosing of about 300 mg leucine (e.g., free leucine), can achieve a circulating level of leucine in a subject that is about 0.25 mM. The dosing of about sildenafil can achieve a circulating concentration of about or less than about 0.1, 0.5, 1, 2, 5, or 10 nM. In some embodiments, the target or achieved circulating concentration of sildenafil is less than about 1 nM. A unit dose of about 20 mg of sildenafil can achieve a circulating concentration of about 100 nM of sildenafil. A unit dose of about 0.2 mg of sildenafil can achieve a circulating concentration of about 1 nM of sildenafil. The dosing of about icariin can achieve a circulating concentration of about or less than about 0.1, 0.5, 1, 2, 5, or 10 nM. In some embodiments, the target or achieved circulating concentration of icariin is less than about 1 nM. A unit dose of about 20 mg of icariin can achieve a circulating concentration of about 100 nM of icariin. A unit dose of about 0.1 mg of icariin can achieve a circulating concentration of about 1 nM of icariin.

In some embodiments, the molar or mass ratios are circulating molar or mass ratios achieved after administration one or more compositions to a subject. The compositions can be a combination composition described herein. The molar ratio of a combination composition in a dosing form can be adjusted to achieve a desired circulating molar ratio. The molar ratio can be adjusted to account for the bioavailability, the uptake, and the metabolic processing of the one or more components of a combination composition. For example, if the bioavailability of a component is low, then the molar amount of a that component can be increased relative to other components in the combination composition. In some embodiments, the circulating molar or mass ratio is achieved within about 0.1, 0.5, 0.75, 1, 3, 5, or 10, 12, 24, or 48 hours after administration. The circulating molar or mass ratio can be maintained for a time period of about or greater than about 0.1, 1, 2, 5, 10, 12, 18, 24, 36, 48, 72, or 96 hours.

In some embodiments, the circulating molar ratio of leucine to sildenafil is about or greater than about 100,000, 250,000, 500,000, 750,000 or more. In some embodiments, the circulating molar ratio of HMB to sildenafil is about or greater than about 1,000, 2,500, 5,000, 7,500 or more. In some embodiments, the circulating molar ratio of resveratrol to sildenafil is about or greater than about 50, 100, 200, 400, 800 or more.

The compositions can be administered to a subject such that the subject is administered a selected total daily dose of the composition. The total daily dose can be determined by the sum of doses administered over a 24 hour period. The total daily dose of the composition can include about 0.05, 0.1, 0.5, 1, 2, 5, 10, 20, 40, 60, 80, or 100 mg of sildenafil. The total daily dose of the composition can include about 1, 10, 20, 50, 100, 150, 300, 400, 500, 750, 1000, 1500, or 2000 mg of icariin. The total daily dose of the composition can include at least about 250, 500, 750, 1000, 1125, 2000, 2250 mg or more of a branched chain amino acid or metabolite thereof. The branched chain amino acid can be leucine, HMB, or any other branched chain amino acid described herein. The total daily dose of the composition can include at least about 3, 7.5, 15, 30, 45, 90 mg or more of B6. The total daily dose of the composition can have a mass ratio of branched chain amino acids or metabolite thereof to vitamin B6 that is about, greater than about, or less than about 45, 50, 55, 60, 65, 70, 75, 80, 85, 90, 100, 110, 120, 130, 140, 150, 175, 200, 250, 500, 750, 1000, or more.

In some embodiments, a selected dose of a composition can be administered to a subject such that the subject achieves a desired circulating level of the composition. The desired circulating level of the composition can be at least about 0.25, 0.5, 0.75, 1 mM or more of leucine. The desired circulating level of the composition can be at least about 10, 25, 50, 100, 150, or 200 nM or more of B6. The desired circulating level of the composition can be about 0.1, 0.5, 1, 2, 5, 10 nM or more of sildenafil. The desired circulating level of the composition can be about 0.1, 0.5, 1, 2, 5, 10 nM or more of icariin. The selected dose can be chosen based on the characteristics of the subject, such as weight, height, ethnicity, or genetics.

Dosing Forms

The compositions described herein can be compounded into a variety of different dosage forms. It can be used orally as a tablet, chewable tablet, caplets, capsule, soft gelatin capsules, lozenges or solution. It can also be used as a nasal spray or for injection when in its solution form. In some embodiments, the composition may be a liquid composition suitable for oral consumption. Compositions of the invention suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion, including liquid dosage forms (e.g., a suspension or slurry), and oral solid dosage forms (e.g., a tablet or bulk powder). Oral dosage forms may be formulated as tablets, pills, dragees, capsules, emulsions, lipophilic and hydrophilic suspensions, liquids, gels, syrups, slurries, suspensions and the like, for oral ingestion by an individual or a patient to be treated. Such dosage forms can be prepared by any of the methods of formulation. For example, the active ingredients can be brought into association with a carrier, which constitutes one or more necessary ingredients. Capsules suitable for oral administration include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. Optionally, the inventive composition for oral use can be obtained by mixing a composition a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). In general, the compositions are prepared by uniformly and intimately admixing the active ingredient with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

The liquid forms, in which the formulations disclosed herein may be incorporated for administration orally or by injection, include aqueous solution, suitably flavored syrups, aqueous or oil suspensions, and flavored emulsions with edible oils such as cottonseed oil, sesame oil, coconut oil, or peanut oil as well as elixirs and similar pharmaceutical vehicles. Suitable dispersing or suspending agents for aqueous suspensions include synthetic natural gums, such as tragacanth, acacia, alginate, dextran, sodium carboxymethyl cellulose, methylcellulose, polyvinylpyrrolidone or gelatin.

A subject can be treated by combination of an injectable composition and an orally ingested composition.

Liquid preparations for oral administration may take the form of, for example, solutions, syrups or suspensions, or they may be presented as a dry product for reconstitution with water or other suitable vehicles before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); preservatives (e.g., methyl or propyl p-hydroxybenzoates or sorbic acid); and artificial or natural colors and/or sweeteners.

The preparation of pharmaceutical compositions of this invention is conducted in accordance with generally accepted procedures for the preparation of pharmaceutical preparations. See, for example, Remington's Pharmaceutical Sciences 18th Edition (1990), E. W. Martin ed., Mack Publishing Co., PA. Depending on the intended use and mode of administration, it may be desirable to process the magnesium-counter ion compound further in the preparation of pharmaceutical compositions. Appropriate processing may include mixing with appropriate non-toxic and non-interfering components, sterilizing, dividing into dose units, and enclosing in a delivery device.

This invention further encompasses anhydrous compositions and dosage forms comprising an active ingredient, since water can facilitate the degradation of some compounds. For example, water may be added (e.g., 5%) in the arts as a means of simulating long-term storage in order to determine characteristics such as shelf-life or the stability of formulations over time. Anhydrous compositions and dosage forms of the invention can be prepared using anhydrous or low moisture containing ingredients and low moisture or low humidity conditions. Compositions and dosage forms of the invention which contain lactose can be made anhydrous if substantial contact with moisture and/or humidity during manufacturing, packaging, and/or storage is expected. An anhydrous composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

An ingredient described herein can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Binders suitable for use in dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Lubricants which can be used to form compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethylaureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the composition.

Lubricants can be also be used in conjunction with tissue barriers which include, but are not limited to, polysaccharides, polyglycans, seprafilm, interceed and hyaluronic acid.

Disintegrants may be used in the compositions of the invention to provide tablets that disintegrate when exposed to an aqueous environment. Too much of a disintegrant may produce tablets which may disintegrate in the bottle. Too little may be insufficient for disintegration to occur and may thus alter the rate and extent of release of the active ingredient(s) from the dosage form. Thus, a sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Examples of suitable fillers for use in the compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

When aqueous suspensions and/or elixirs are desired for oral administration, the active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

In one embodiment, the composition may include a solubilizer to ensure good solubilization and/or dissolution of the compound of the present invention and to minimize precipitation of the compound of the present invention. This can be especially important for compositions for non-oral use, e.g., compositions for injection. A solubilizer may also be added to increase the solubility of the hydrophilic drug and/or other components, such as surfactants, or to maintain the composition as a stable or homogeneous solution or dispersion.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof. A non-exhaustive list of examples of excipients includes monoglycerides, magnesium stearate, modified food starch, gelatin, microcrystalline cellulose, glycerin, stearic acid, silica, yellow beeswax, lecithin, hydroxypropylcellulose, croscarmellose sodium, and crospovidone.

The compositions described herein can also be formulated as extended-release, sustained-release or time-release such that one or more components are released over time. Delayed release can be achieved by formulating the one or more components in a matrix of a variety of materials or by microencapsulation. The compositions can be formulated to release one or more components over a time period of 4, 6, 8, 12, 16, 20, or 24 hours. The release of the one or more components can be at a constant or changing rate.

Using the controlled release dosage forms provided herein, the one or more cofactors can be released in its dosage form at a slower rate than observed for an immediate release formulation of the same quantity of components. In some embodiments, the rate of change in the biological sample measured as the change in concentration over a defined time period from administration to maximum concentration for an controlled release formulation is less than about 80%, 70%, 60%, 50%, 40%, 30%, 20%, or 10% of the rate of the immediate release formulation. Furthermore, in some embodiments, the rate of change in concentration over time is less than about 80%, 70%, 60%, 50%, 40%, 30%, 20%, or 10% of the rate for the immediate release formulation.

In some embodiments, the rate of change of concentration over time is reduced by increasing the time to maximum concentration in a relatively proportional manner. For example, a two-fold increase in the time to maximum concentration may reduce the rate of change in concentration by approximately a factor of 2. As a result, the one or more cofactors may be provided so that it reaches its maximum concentration at a rate that is significantly reduced over an immediate release dosage form. The compositions of the present invention may be formulated to provide a shift in maximum concentration by 24 hours, 16 hours, 8 hours, 4 hours, 2 hours, or at least 1 hour. The associated reduction in rate of change in concentration may be by a factor of about 0.05, 0.10, 0.25, 0.5 or at least 0.8. In certain embodiments, this is accomplished by releasing less than about 30%, 50%, 75%, 90%, or 95% of the one or more cofactors into the circulation within one hour of such administration.

Optionally, the controlled release formulations exhibit plasma concentration curves having initial (e.g., from 2 hours after administration to 4 hours after administration)

slopes less than 75%, 50%, 40%, 30%, 20% or 10% of those for an immediate release formulation of the same dosage of the same cofactor.

In some embodiments, the rate of release of the cofactor as measured in dissolution studies is less than about 80%, 70%, 60% 50%, 40%, 30%, 20%, or 10% of the rate for an immediate release formulation of the same cofactor over the first 1, 2, 4, 6, 8, 10, or 12 hours.

The controlled release formulations provided herein can adopt a variety of formats. In some embodiments, the formulation is in an oral dosage form, including liquid dosage forms (e.g., a suspension or slurry), and oral solid dosage forms (e.g., a tablet or bulk powder), such as, but not limited to those, those described herein.

The controlled release tablet of a formulation disclosed herein can be of a matrix, reservoir or osmotic system. Although any of the three systems is suitable, the latter two systems can have more optimal capacity for encapsulating a relatively large mass, such as for the inclusion of a large amount of a single cofactor, or for inclusion of a plurality of cofactors, depending on the genetic makeup of the individual. In some embodiments, the slow-release tablet is based on a reservoir system, wherein the core containing the one or more cofactors is encapsulated by a porous membrane coating which, upon hydration, permits the one or more cofactors to diffuse through. Because the combined mass of the effective ingredients is generally in gram quantity, an efficient delivery system can provide optimal results.

Thus, tablets or pills can also be coated or otherwise compounded to provide a dosage form affording the advantage of prolonged action. For example, the tablet or pill can comprise an inner dosage an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings such materials including a number of polymeric acids and mixtures of polymeric acids with such materials as shellac, cetyl alcohol and cellulose acetate. In some embodiments, a formulation comprising a plurality of cofactors may have different cofactors released at different rates or at different times. For example, there can be additional layers of cofactors interspersed with enteric layers.

Methods of making sustained release tablets are known in the art, e.g., see U.S. Patent Publications 2006/051416 and 2007/0065512, or other references disclosed herein. Methods such as described in U.S. Pat. Nos. 4,606,909, 4,769,027, 4,897,268, and 5,395,626 can be used to prepare sustained release formulations of the one or more cofactors determined by the genetic makeup of an individual. In some embodiments, the formulation is prepared using OROS® technology, such as described in U.S. Pat. Nos. 6,919,373, 6,923,800, 6,929,803, and 6,939,556. Other methods, such as described in U.S. Pat. Nos. 6,797,283, 6,764,697, and 6,635,268, can also be used to prepare the formulations disclosed herein.

In some embodiments, the compositions can be formulated in a food composition. For example, the compositions can be a beverage or other liquids, solid food, semi-solid food, with or without a food carrier. For example, the compositions can include a black tea supplemented with any of the compositions described herein. The composition can be a dairy product supplemented any of the compositions described herein. In some embodiments, the compositions can be formulated in a food composition. For example, the compositions can comprise a beverage, solid food, semi-solid food, or a food carrier.

In some embodiments, liquid food carriers, such as in the form of beverages, such as supplemented juices, coffees, teas, sodas, flavored waters, and the like can be used. For example, the beverage can comprise the formulation as well as a liquid component, such as various deodorant or natural carbohydrates present in conventional beverages. Examples of natural carbohydrates include, but are not limited to, monosaccharides such as, glucose and fructose; disaccharides such as maltose and sucrose; conventional sugars, such as dextrin and cyclodextrin; and sugar alcohols, such as xylitol and erythritol. Natural deodorant such as taumatin, stevia extract, levaudioside A, glycyrrhizin, and synthetic deodorant such as saccharin and aspartame may also be used. Agents such as flavoring agents, coloring agents, and others can also be used. For example, pectic acid and the salt thereof, alginic acid and the salt thereof, organic acid, protective colloidal adhesive, pH controlling agent, stabilizer, a preservative, glycerin, alcohol, or carbonizing agents can also be used. Fruit and vegetables can also be used in preparing foods or beverages comprising the formulations discussed herein.

Alternatively, the compositions can be a snack bar supplemented with any of the compositions described herein. For example, the snack bar can be a chocolate bar, a granola bar, or a trail mix bar. In yet another embodiment, the present dietary supplement or food compositions are formulated to have suitable and desirable taste, texture, and viscosity for consumption. Any suitable food carrier can be used in the present food compositions. Food carriers of the present invention include practically any food product. Examples of such food carriers include, but are not limited to food bars (granola bars, protein bars, candy bars, etc.), cereal products (oatmeal, breakfast cereals, granola, etc.), bakery products (bread, donuts, crackers, bagels, pastries, cakes, etc.), beverages (milk-based beverage, sports drinks, fruit juices, alcoholic beverages, bottled waters), pastas, grains (rice, corn, oats, rye, wheat, flour, etc.), egg products, snacks (candy, chips, gum, chocolate, etc.), meats, fruits, and vegetables. In an embodiment, food carriers employed herein can mask the undesirable taste (e.g., bitterness). Where desired, the food composition presented herein exhibit more desirable textures and aromas than that of any of the components described herein. For example, liquid food carriers may be used according to the invention to obtain the present food compositions in the form of beverages, such as supplemented juices, coffees, teas, and the like. In other embodiments, solid food carriers may be used according to the invention to obtain the present food compositions in the form of meal replacements, such as supplemented snack bars, pasta, breads, and the like. In yet other embodiments, semi-solid food carriers may be used according to the invention to obtain the present food compositions in the form of gums, chewy candies or snacks, and the like.

The dosing of the combination compositions can be administered about, less than about, or more than about 1, 2, 3, 4, 5, 6, 7, 8, 9, 10 or more times a daily. A subject can receive dosing for a period of about, less than about, or greater than about 1, 2, 3, 4, 5, 6, 7, 8, 9, 10, 11, 12, 13, 14 or more days, weeks or months. A unit dose can be a fraction of the daily dose, such as the daily dose divided by the number of unit doses to be administered per day. A unit dose can be a fraction of the daily dose that is the daily dose divided by the number of unit doses to be administered per day and further divided by the number of unit doses (e.g.

tablets) per administration. The number of unit doses per administration may be about, less than about, or more than about 1, 2, 3, 4, 5, 6, 7, 8, 9, 10, or more. The number of doses per day may be about, less than about, or more than about 1, 2, 3, 4, 5, 6, 7, 8, 9, 10, or more. The number of unit doses per day may be determined by dividing the daily dose by the unit dose, and may be about, less than about, or more than about 1, 2, 3, 4, 5, 6, 7, 8, 9, 10, 11, 12, 13, 14, 15, 6, 17, 18, 19, 20, or more unit doses per day. For example, a unit dose can be about ½, ⅓, ¼, ⅕, ⅙, 1/7, ⅛, 1/9, 1/10. A unit dose can be about one-third of the daily amount and administered to the subject three times daily. A unit dose can be about one-half of the daily amount and administered to the subject twice daily. A unit dose can be about one-fourth of the daily amount with two unit doses administered to the subject twice daily. In some embodiments, a unit dose comprises about, less than about, or more than about 50 mg resveratrol. In some embodiments, a unit dose comprises about, less than about, or more than about 550 mg leucine. In some embodiments, a unit dose comprises about, less than about, or more than about 200 mg of one or more leucine metabolites. In some embodiments, a unit dose (e.g. a unit dose comprising leucine) is administered as two unit doses two times per day. In some embodiments, a unit dose (e.g. a unit dose comprising one or more leucine metabolites, such as HMB) is administered as one unit dose two timer per day.

Compositions disclosed herein can further comprise a flavorant and can be a solid, liquid, gel or emulsion.

Methods

The subject application provides methods of increasing sirtuin pathway output (including AMPK, a signaling molecule in the sirtuin pathway) in a subject using a selective PDE inhibitor. As described herein, the output of the sirtuin pathway can be characterized at the molecular level or by a resulting physiological effect. In some embodiments, the invention provides for methods of increasing fatty acid oxidation in a subject comprising the administration of a composition as disclosed herein to the subject. In various embodiments of the invention, a composition is administered to the subject in an amount that delivers synergizing amounts of one or more branched amino acids or a metabolite thereof, such as leucine or HMB, and a PDE 5 inhibitor, such as sildenafil or icariin, sufficient to increase fatty acid oxidation within the cells of the subject.

The methods described herein can be useful for a variety of applications. These applications include (a) an increase in sirtuin-pathway output, (b) an increase in mitochondrial biogenesis, (c) an increase in the formation of new mitochondria, (d) an increase in mitochondrial functions, (e) an increase in fatty acid oxidation, (f) an increase in heat generation, (g) an increase in insulin sensitivity, (h) an increase in glucose uptake, (i) an increase in vasodilation, (j) a decrease in weight, (k) a decrease in adipose volume, (l) a decrease in inflammatory response or markers in a subject, and (m) an increase in irisin production. Any of these applications can be achieved by administering one or more compositions described herein.

Accordingly, the invention provides a method for administering a composition comprising (a) one or more types of branched amino acids and/or metabolites thereof and (b) a selective PDE inhibitor present in a sub-therapeutic amount, wherein the composition is synergistically effective in increasing the sirtuin-pathway output by at least about 5 fold as compared to that of component (a) or (b) when used alone.

The output of the pathways can be measured using one or more methods, disclosed herein and/or known in the art. For example, fatty acid oxidation can be determined by measuring oxygen consumption, or 3H-labeled palmitate oxidation. Mitochondrial biogenesis can be measured using a mitochondrial probe by using fluorescence. AMPK activity can be determined by measuring AMPK phosphorylation via an ELISA assay or by Western blot. Sirt1 activity can be determined by measuring deacetylation of a substrate, which can be detected using a fluorophore.

An increase in sirt1, sirt2, or sirt3 is observed by applying a corresponding substrate in a deacylation assay conducted in vitro. The substrate for measuring SIRT1 activity can be any substrate known in the art (for example a peptide containing amino acids 379-382 of human p53 (Arg-His-Lys-Lys[Ac]). The substrate for measuring SIRT3 activity can be any substrate known in the art (for example a peptide containing amino acids 317-320 of human p53 (Gln-Pro-Lys-Lys[Ac])). In some instances, the increase in sirt activity in one or more assays conducted in the presence of one or more combination compositions described herein results in an activity increase of at least about 1, 2, 3, 5, or 10 fold, as compared to the activity measured in the presence of only one component of the combination compositions. For example, the use of a combination composition comprising (a) a sirtuin pathway activator (such as sildenafil) and (b) a branched chain amino acid or metabolite thereof (such as HMB) results in an increase in sirt3 activity by at least about 5 fold as compared to the activity measured in the presence of (a) or (b) alone. Also, the use of a subject composition results in an increase in sirt1 activity that is 1.5, 2, 5 or 10 fold greater than the activity measured in the presence of only one component of the composition.

The invention provides a method for administering a composition comprising: (a) one or more types of branched amino acids and/or metabolites thereof, and (b) a selective PDE inhibitor, wherein the target or achieved circulating molar ratio of component (a) to (b) in a subject administered said composition is greater than about 100,000, 200,000, or 500,000, and wherein the composition when administered to a subject in need thereof synergistically enhances energy metabolism as measured by a decrease in weight gain of a subject, a decrease in visceral adipose volume of a subject, an increase in fat oxidation of a subject, an increase in insulin sensitivity of a subject, an increase of glucose uptake in muscle of a subject, a decrease in inflammation markers, an increase in vasodilatation, and/or an increase in body temperature.

The invention provides a method for administering a food composition comprising: (a) one or more types of branched amino acids and/or metabolites thereof; (b) a selective PDE inhibitor (e.g., sildenafil or icariin), wherein (a) and (b) are present in an amount that synergistically effect a decrease in weight gain of a subject, a decrease in visceral adipose volume of a subject, an increase in fat oxidation of a subject, an increase in insulin sensitivity of a subject, an increase of glucose uptake in muscle of a subject, an increase in vasodilatation, a decrease in oxidative stress, a decrease in inflammatory stress, and/or an increase in body temperature; and (c) a food carrier.

The invention provides a method for administering a composition comprising: a combination of (a) one or more types of branched amino acids and/or metabolites thereof; and (b) a PDE-5 inhibitor, wherein the composition is substantially free of non-branched amino acids, wherein the combination when administered to a subject in need thereof enhances mitochondrial biogenesis to a greater degree as compared to administering to a subject component (a) or component (b) alone, and wherein the enhanced mitochondrial biogenesis is measured by a decrease in weight of a subject, a decrease in visceral adipose volume of a subject, an increase in fat oxidation of a subject, an increase in insulin sensitivity of a subject, an increase of glucose uptake in muscle of a subject, an increase in vasodilatation, a decrease in oxidative stress, a decrease in inflammatory stress, and/or an increase in body temperature. For some embodiment, the amount of (a) and the amount of (b) are synergistic.

The invention provides a method for administering a composition comprising: a combination of (a) one or more types of branched amino acids and/or metabolites thereof; and (b) a PDE-5 inhibitor, wherein the composition is substantially free of non-branched amino acids, wherein the combination when administered to a subject in need thereof enhances mitochondrial biogenesis to a greater degree as compared to administering to a subject component (a) or component (b) alone, and wherein the enhanced mitochondrial biogenesis is measured by a decrease in weight of a subject, a decrease in visceral adipose volume of a subject, an increase in fat oxidation of a subject, an increase in insulin sensitivity of a subject, an increase of glucose uptake in muscle of a subject, an increase in vasodilatation, a decrease in oxidative stress, a decrease in inflammatory stress, and/or an increase in body temperature. In some embodiment, the amount of (a) and the amount of (b) are synergistic.

The invention provides for a method of enhancing fat oxidation in a subject in need thereof comprising administering to the subject any of the compositions described herein over a time period, wherein the fat oxidation in the subject is increased over the time period. The fat oxidation can be increased by about or greater than about 5, 10, 15, 20, 50, 100, 200, or 500%.

The invention provides for a method of reducing an inflammatory response in a subject in need thereof comprising administering to the subject a composition any of the compositions described herein over a time period, wherein the inflammatory response in the subject is reduced over the time period. The inflammatory response can be decreased by about or greater than about 5, 10, 15, 20, 50, or 100%.

Inflammatory marker and cytokine levels, including but not limited to IL-6, adiponectin, TNF-α and CRP levels in plasma can determined by immune assays, such as ELISA (Assay Designs, Ann Arbor, Mich.; Linco Research, St. Charles, Mo.; and Bioscience, San Diego, Calif.).

The invention provides for a method of increasing or maintaining body temperature in a subject comprising administering to the subject a composition any of the compositions described herein over a time period, wherein the body temperature in the subject is increased over the time period. The body temperature can be increased by about or greater than about 1, 2, 3, 4, 5, 10, 15, or 20%.

The invention provides for a method of inducing vasodilatation comprising administering to the subject a composition of any of the compositions described herein over a time period, wherein the vasodilation in the subject is induced over the time period. The vasodilation of blood vessels can be increased by about or greater than about 1, 2, 3, 5, 10, 20, 50, or 100%. The vasodilation can be measured by optically, by measuring vasorestriction, or by a variety of other techniques. These techniques include the invasive forearm technique, the brachial artery ultrasound technique, and pulse wave analysis. Methods for measuring vasodilation are described in Lind et al., "Evaluation of four different methods to measure endothelium-dependent vasodilation in the human peripheral circulation," Clinical Science 2002, 102, 561-567.

The invention provides for a method of increasing irisin production, comprising administering to the subject any of the compositions described herein, wherein irisin production in the subject increases over a time period. In some embodiments, the increase in irisin production (or in an indicator providing evidence thereof) is an increase of about, or more than about 5%, 10%, 20%, 30%, 40%, 50%, 60%, 70%, 80%, 90%, 100%, 125%, 150%, 175%, 200%, or more. In some embodiments, the increase in irisin production (or in an indicator providing evidence thereof) is an increase of about, or more than about 1-fold, 3-fold, 5-fold, 6-fold, 8-fold, 10-fold, 15-fold, 20-fold, 50-fold, or more. In some embodiments, the increase in irisin production is evidenced by an increase in FNDC5 expression (e.g. as measured from mRNA and/or protein level). In some embodiments, the increase in irisin production is evidenced by an increase in one or more indicia of fat cell browning (e.g. fatty acid oxidation, and/or an increase in expression of one or more brown fat selective genes in adipose tissue). Non-limiting examples of brown fat selective genes include Ucp1, Cidea, Prdm16, and Ndufs. In some embodiments, the increase in irisin production is evidenced by increased secretion of irisin from the cell (e.g. as measured from media in which the cell is cultured, or from circulating plasma in a subject). Increases in gene levels can be measured directly (e.g. changes in mRNA or protein levels) or indirectly (changes in effects associated with expression increase, such as an increased expression of a downstream gene). Methods for detecting changes in gene expression level are known in the art, and include, without limitation, methods for the detection of mRNA (e.g. RT-PCR, Northern blot, and microarray hybridization), detection of protein products (e.g. Western blot, and ELISA), a detection of one or more activities of the translated protein (e.g. enzyme activity assays).

The invention provides for a method of treating a diabetic subject, e.g., a subject with Type I diabetes, Type II diabetes, and/or diet-induced diabetes, comprising administering to the subject any of the compositions described herein over a time period. The diabetes may be characterized by reduced insulin levels, insulin resistance, or a combination of both. In some embodiments, the administering is effective to improve a symptom of diabetes in the subject. For example, administration of the composition can improve insulin sensitivity in a subject. Type I diabetes may be characterized by reduced insulin production as compared to a subject without Type I diabetes. Administration of a composition described herein can improve the sensitivity of a subject with Type I diabetes (e.g., having reduced insulin) to the insulin that is produced by or administered to the subject. Type II diabetes may be characterized by reduced sensitivity to insulin. Accordingly, administration of a composition described herein can improve insulin sensitivity in a subject with Type II diabetes.

An exemplary symptom of diabetes is reduced insulin sensitivity. Insulin sensitivity can be determined by any means known in the art. For example, insulin sensitivity can be determined by measuring blood glucose levels in a subject, in some cases over a period of time, following administration of a bolus of insulin. Subjects with reduced insulin sensitivity typically exhibit an attenuated drop in blood glucose levels following insulin administration, as compared to subject with normal insulin sensitivity. Administration of a composition described herein can increase insulin sensitivity in a subject. Administration of a composition described herein can increase insulin sensitivity in the subject, as compared to, e.g., the level of insulin sensitivity in the subject prior to the administration. Insulin sensitivity can be increased by about or greater than about 1, 2, 3, 5, 10, 20, 50, 100, or 200%, as compared to the level of insulin sensitivity in the subject prior to administration of the composition.

Another exemplary symptom of diabetes is reduced glucose tolerance. Glucose tolerance can be determined by any means known in the art. For example, glucose tolerance can be determined by measuring blood glucose levels in a subject, in some cases over a period of time, following administration of a bolus of glucose. Subjects with reduced glucose tolerance typically exhibit elevated blood glucose levels and/or slower clearance of glucose from the blood as compared to subjects with normal glucose tolerance. Administration of a composition described herein can increase glucose tolerance in a subject. Administration of a composition described herein can increase glucose tolerance in the subject, as compared to, e.g., the level of glucose tolerance in the subject prior to the administration. Glucose tolerance can be increased by about or greater than about 1, 2, 3, 5, 10, 20, 50, 100, or 200%, as compared to, e.g., the level of glucose tolerance in the subject prior to the administration.

Another symptom of diabetes is elevated post-prandial or fasting blood glucose levels. Blood glucose levels can be determined by any means known in the art. For example, blood glucose levels can be determined by, e.g., glucose monitor. Elevated blood glucose can be, e.g., an increase in blood glucose levels in a subject with diabetes as compared to blood glucose levels in a subject or control population without diabetes. Administration of a composition described herein can reduce blood glucose levels (e.g., post-prandial and/or fasting blood glucose) in a subject. Administration of a composition described herein can reduce blood glucose levels (e.g., post-prandial and/or fasting blood glucose) in the subject, as compared to, e.g., the level of blood glucose in the subject prior to the administration. Administration of a composition described herein can reduce blood glucose levels by about or greater than about 1, 2, 3, 5, 10, 20, 50, 60, 70, 80, 90, or 100% as compared to the blood glucose levels in the subject prior to the administration. Administration of a composition described herein can reduce blood glucose levels to normal levels, e.g., levels found in a control population that does not have diabetes.

Another symptom of diabetes is elevated Homeostatic Assessment of Insulin Resistance ($HOMA_{IR}$). $HOMA_{IR}$ can be determined by any means known in the art, for example, by the following equation: $HOMA_{IR}$=[Insulin (uU/mL)× glucose (mM)]/22.5. Administration of a composition described herein can reduce $HOMA_{IR}$ levels in the subject. Elevated $HOMA_{IR}$ can be, e.g., an increase in $HOMA_{IR}$ levels in a subject with diabetes as compared to $HOMA_{IR}$ levels in a subject or control population without diabetes. Administration of a composition described herein can reduce $HOMA_{IR}$ levels in a subject. Administration of a composition described herein can reduce $HOMA_{IR}$ levels in the subject, as compared to, e.g., the $HOMA_{IR}$ levels in the subject prior to administration of a composition described herein. Administration of the composition can decrease $HOMA_{IR}$ levels by about or greater than about 1, 2, 3, 5, 10, 20, 50, 60, 70, 80, 90, or 100%, as compared to the $HOMA_{IR}$ levels in the subject prior to administration of the composition. $HOMA_{IR}$ levels can be decreased to normal levels, e.g., levels found in a control population that does not have diabetes.

Another symptom of diabetes is elevated liver mass. Liver mass can be estimated by any means known in the art, for example, by imaging or by biopsy. Elevated liver mass can be, e.g., an increase liver mass in a subject with diabetes as compared to liver mass in a subject or control population without diabetes. Administration of a composition described herein can reduce liver mass in the subject. Administration of a composition described herein can decrease liver mass in the subject as compared to, e.g., the liver mass of the subject prior to administration of a composition described herein. Administration of the composition can decrease liver mass by about or greater than about 1, 2, 3, 5, 10, 20, 50, 60, 70, 80, 90, or 100%, as compared to the liver mass of the subject prior to administration of the composition. Administration of the composition can decrease liver mass of the subject to normal, e.g., to an average liver mass found in a control population that does not have diabetes.

Another symptom of diabetes is elevated inflammation. Inflammation in a subject can be estimated by any means known in the art, for example, by analysis of markers associated with inflammation in a subject or in a biological sample obtained from a subject. Markers associated with inflammation are known in the art, and include, e.g., inflammatory cells types, protein receptors, inflammatory molecules, and other indicators involved in inflammatory pathways. Exemplary markers associated with inflammation include, but are not limited to cytokines, IL-6, adiponectin, MCP-1 and C-reactive protein (CRP). The biological sample can be, e.g., whole blood, plasma, serum, saliva, sputum, urine, feces, skin, hair, or tissue biopsy. The biological sample can be obtained by any means known in the art. The markers can be detected and/or assessed by any means known in the art, for example, by imaging, by immunofluorescence, by immunohistochemistry, by gene expression analysis, by in situ hybridization, by RNase protection assay, by reporter assay, by ELISA, or by any other method. Administration of a composition described herein can reduce inflammation in a subject. Administration of a composition described herein can reduce inflammation in the subject, as compared to, e.g., inflammation levels in the subject prior to the administration. Elevated inflammation can be, e.g., an increase in inflammation levels in a subject with diabetes as compared to inflammation levels in a subject or control population without diabetes. Administration of a composition described herein can reduce by about or greater than about 1, 2, 3, 5, 10, 20, 50, 60, 70, 80, 90, or 100%, as compared to inflammation levels in the subject prior to the administration. Administration of a composition described herein can reduce inflammation in the subject to normal levels, e.g., to average inflammation levels found in a control population that does not have diabetes.

In some embodiments, insulin signaling can also be measured. Insulin signaling can be measured by measuring total and phosphorylated Akt, GSK-3β, IGF-1R, IR, IRS-1, p70S6K and PRAS40 in tissue lysates via the Luminex Kits "Akt Pathway Total 7-Plex Panel" (Cat# LH00002) and "Akt Pathway Phospho 7-Plex Panel" (Cat# LH00001) from Invitrogen Life Science.

In some embodiments, a branched chain amino acid (or a metabolite thereof) and/or a selective PDE inhibitor are administered in an amount that reduces the therapeutically effective dose of metformin for a subject. In some embodiments, the therapeutically effective dose of metformin is reduced by about or more than about 50%, 60%, 70%, 80%, 90%, 95%, 97.5%, 99.9%, 99.99%, or more. In some embodiments, administration of compositions of the invention reduces body fat (e.g. visceral fat) by about or more than about 5%, 10%, 15%, 20%, 25%, 50%, or more.

The subject application also provides methods of increasing mitochondrial biogenesis in a subject comprising the administration of a composition disclosed herein to a subject. In various embodiments of the invention, a composition is administered to the subject in an amount that delivers synergizing amount of a selective PDE inhibitor sufficient to increase mitochondrial biogenesis within the cells of the subject. Another embodiment provides for the administration of a composition comprising synergizing amounts of leucine and a PDE inhibitor (e.g., PDE-5 inhibitor) to the subject in an amount sufficient to increase mitochondrial biogenesis within the cells of the subject. Yet other embodiments provide for the administration of a composition comprising synergizing amounts of leucine, PDE inhibitor (e.g., PDE-5 inhibitor), and resveratrol to a subject in an amount sufficient to increase mitochondrial biogenesis in the subject. Mitochondrial biogenesis and fat oxidation may be induced in various cells, including muscle cells and adipocytes.

Another aspect of the invention provides methods of reducing weight gain or reducing adipose volume in a subject comprising the administration of compositions disclosed herein. Body weight can be measured with a calibrated scale and height measured with a wall-mounted stadiometer, and body mass index can be calculated via standard equation (kg/m2). Fat mass can be assessed via dual-energy X-ray absorptiometry at baseline, and 12 and 24 weeks. A LUNAR Prodigy dual-energy X-ray absorptiometry system (GE Healthcare, Madison, Wis.), or any other X-ray absorptiometry system known in the art, can be maintained and calibrated for use. A spine phantom can be assessed every day to determine whether any drift in the machine occurred, followed by a daily calibration block.

In this aspect of the invention, a composition is administered to the subject in an amount that delivers synergizing amount of a selective PDE inhibitor in combination with one or more of leucine, HMB, and resveratrol sufficient to reduce weight gain in a subject.

Administration of compositions disclosed herein that increase SIRT1 and SIRT3 activity may be useful in any subject in need of metabolic activation of adipocytes or one or more of their muscles, e.g., skeletal muscle, smooth muscle or cardiac muscle or muscle cells thereof. A subject may be a subject having cachexia or muscle wasting. Increasing SIRT3 activity may also be used to increase or maintain body temperature, e.g., in hypothermic subjects and increasing SIRT1 activity is beneficial for treating diabetes (type 2 diabetes) and impaired glucose tolerance and reducing inflammatory responses in a subject.

Increasing SIRT3 activity may also be used for treating or preventing cardiovascular diseases, reducing blood pressure by vasodilation, increasing cardiovascular health, and increasing the contractile function of vascular tissues, e.g., blood vessels and arteries (e.g., by affecting smooth muscles). Generally, activation of SIRT3 may be used to stimulate the metabolism of adipocytes or any type of muscle, e.g., muscles of the gut or digestive system, or the urinary tract, and thereby may be used to control gut motility, e.g., constipation, and incontinence. SIRT3 activation may also be useful in erectile dysfunction. It may also be used to stimulate sperm motility, e.g., and be used as a fertility drug. Other embodiments in which it would be useful to increase SIRT3 include repair of muscle, such as after a surgery or an accident, increase of muscle mass; and increase of athletic performance.

Thus the invention provides methods in which beneficial effects are produced by contacting one or more muscle cells with an agent that increases the protein or activity level of SIRT3 in the cell. These methods effectively facilitate, increase or stimulate one or more of the following: mimic the benefits of calorie restriction or exercise in the muscle cell, increase mitochondrial biogenesis or metabolism, increase mitochondrial activity and/or endurance in the muscle cell, sensitize the muscle cell to glucose uptake, increase fatty acid oxidation in the muscle cell, decrease reactive oxygen species (ROS) in the muscle cell, increase PGC-la and/or UCP3 and/or GLUT4 expression in the muscle cell, and activate AMP activated protein kinase (AMPK) in the muscle cell. Various types of muscle cells can be contacted in accordance with the invention. In some embodiments, the muscle cell is a skeletal muscle cell. In certain embodiments, the muscle cell is a cell of a slow-twitch muscle, such as a soleus muscle cell.

Resting metabolic rate (RMR)/Substrate Oxidation is measured by indirect calorimetry using the open circuit technique between the hours of 6 AM and 10 AM after a 12-hour fast and 48-hour abstention from exercise utilizing a SensorMedics Vmax 29n metabolic cart (Sensor Medics, Anaheim, Calif.). Following a urinary void, the participant rests quietly for 30 minutes in an isolated room with temperature controlled (21-24° C.) environment. The subject is then placed in a ventilated hood for a minimum of 30 minutes, until steady state is achieved. Criteria for a valid measurement can be a minimum of 15 minutes of steady state, with steady state determined as less than 10% fluctuation in minute ventilation and oxygen consumption and less than 5% fluctuation in respiratory quotient. Metabolic rate is calculated using the Weir equation, RQ is calculated as $CO_2$ production/$O_2$ consumption, and substrate oxidation is calculated from RQ after correction for urinary nitrogen losses.

Glucose uptake can be measured using in vivo or in vitro techniques. For example, glucose uptake can be measured in vivo using a PET scan in conjunction with labeled glucose or glucose analog. Measurements of glucose uptake can be quantified from the PET scan or by any other technique known in the art. In some embodiments, the glucose uptake can be measured by quantitation of exogenously administered 18-F-deoxyglucose uptake via PET.

ROS/Oxidative Stress can be measured by drawing blood into EDTA-treated tubes, centrifuging to separate plasma, and aliquoting samples for individual assays. Plasma can be maintained at −80° C. under nitrogen to prevent oxidative changes prior to measurements. Plasma malonaldehyde (MDA) can be measured using a fluorometric assay, and plasma 8-isoprostane F2α was measured by ELISA (Assay Designs, Ann Arbor, Mich.).

Another embodiment provides for the administration of a composition comprising synergizing amounts of leucine and resveratrol to the subject in an amount sufficient to increase fatty acid oxidation within the cells of the subject. Yet other embodiments provide for the administration of a composition comprising synergizing amounts of leucine, HMB and resveratrol to a subject in an amount sufficient to increase fatty acid oxidation in the subject. The leucine may be in free amino acid form.

The compositions can be administered to a subject orally or by any other methods. Methods of oral administration include administering the composition as a liquid, a solid, or a semi-solid that can be taken in the form of a dietary supplement or a food stuff.

The compositions can be administered periodically. For example, the compositions can be administered one, two, three, four times a day, or even more frequent. The subject can be administered every 1, 2, 3, 4, 5, 6 or 7 days. In some embodiments, the compositions are administered three times daily. The administration can be concurrent with meal time of a subject. The period of treatment or diet supplementation can be for about 1, 2, 3, 4, 5, 6, 7, 8, or 9 days, 1 week or longer, 2 weeks or longer, six weeks or longer, 1-11 months or longer, 1 year or longer, 2 years or longer, or 5 years or longer. In some embodiments of the invention, the dosages that are administered to a subject can change or remain constant over the period of treatment. For example, the daily dosing amounts can increase or decrease over the period of administration.

The compositions can be therapeutically effective over a prolonged time period, such that the beneficial effects are maintained. The beneficial effects can be maintained by administration of the compositions described herein for a period of at least about 4, 6, 8, 10, or 12 weeks, or at least about 4, 6, 12, 24, 48, or 72 months.

The compositions can be administered to a subject such that the subject is administered a selected total daily dose of the composition, as described herein. For example, the total daily dose of the composition can include about 0.05, 0.1, 0.5, 1, 2, 5, 10, 20, 40, 60, 80, or 100 mg of sildenafil.

In some embodiments, a selected dose of a composition can be administered to a subject such that the subject achieves a desired circulating level of the composition, as described herein. For example, the desired circulating level of the composition can be about 0.1, 0.5, 1, 2, 5, 10 nM or more of sildenafil and the desired circulating level of the composition can be at least about 0.25, 0.5, 0.75, 1 mM or more of leucine. The selected dose can be chosen based on the characteristics of the subject, such as weight, height, ethnicity, or genetics.

In another aspect, the invention provides for a method for increasing energy metabolism in a subject, comprising administering a composition described herein, such as one comprising a selective PDE inhibitor to a subject in need for a period of time in which the subject's energy metabolism is increased. The invention also provides for a method for enhancing fat oxidation in a subject in need thereof comprising administering a composition described herein at least two times per day over a time period, wherein the fat oxidation in the subject is increased over the time period as compared to the fat oxidation in the subject prior to said time period. The subject's energy metabolism can be measured before treatment and after treatment to determine if the subject's energy metabolism has increased. Alternatively, subjects can be pooled into test and control groups, where the increase in energy metabolism is measured between groups.

The length of the period of administration and/or the dosing amounts can be determined by a physician, a nutritionist, or any other type of clinician. The period of time can be one, two, three, four or more weeks. Alternatively, the period of time can be one, two, three, four, five, six or more months.

In another aspect, the invention provides for a method for increasing energy metabolism in a subject comprising administering a composition described herein at a selected dosing level, wherein the selected dosing level induces a circulating level of about 0.5 mM leucine and about 1 nM sildenafil in the subject. The dosing level can be adjusted based on the subject's characteristics, such as weight, height, ethnicity, genetics, or baseline energy metabolism level.

The physician, nutritionist, or clinician can observe the subject's response to the administered compositions and adjust the dosing based on the subject's performance or measured circulating levels of leucine, a PDE 5 inhibitor, or any other component of the composition. For example, dosing levels can be increased for subjects that show reduced effects in energy regulation or circulating levels of a PDE 5 inhibitor or leucine below desired target levels.

In some embodiments, the compositions administered to a subject can be optimized for a given subject. For example, the ratio of branched chain amino acids to a selective PDE inhibitor or the particular components in a combination composition can be adjusted. The ratio and/or particular components can be selected after evaluation of the subject after being administered one or more compositions with varying ratios of branched chain amino acids to a selective PDE inhibitor or varying combination composition components.

In some embodiments, the methods described herein comprise administering the invention composition alone. However, any of the methods described herein can comprise a combination therapy. The combination therapy can comprise administering a composition described herein (e.g., a composition comprising a branched chain amino acid or metabolite thereof and a PDE inhibitor) in combination with an additional therapeutic agent. The additional therapeutic agent can be, e.g., a therapeutic agent for the treatment of diabetes. As used herein, the terms "co-administration", "administered in combination with" and their grammatical equivalents are meant to encompass administration of the invention composition and additional therapeutic agent to a single subject, and are intended to include treatment regimens in which the composition and additional therapeutic agent are administered by the same or different route of administration or at the same or different times. In some embodiments the composition described herein are co-administered with one or more additional therapeutic agents. These terms encompass administration of the invention composition and additional therapeutic agent to a subject so that the active ingredients of the invention composition, additional therapeutic agent(s), and/or their metabolites are present in the subject at the same time. They include simultaneous administration in separate compositions, administration at different times in separate compositions, and/or administration in a single composition in which the PDE inhibitor, branched chain amino acid, and additional therapeutic agent are present. Thus, in some embodiments, the PDE inhibitor, branched chain amino acid, and additional therapeutic agent are administered in a single composition. In some embodiments, the PDE inhibitor, branched chain amino acid, and additional therapeutic agent) are admixed in the single composition. Exemplary additional therapeutic agents are described herein.

In some embodiments, the additional therapeutic agent is a biguanide. In some instances, biguanides reduce blood and/or plasma glucose levels. Examples of biguanides include and are not limited to metformin, buformin, phenformin, proguanil or the like.

In some embodiments, the additional therapeutic agent is an incretin mimetic. In some embodiments, an incretic mimic augments pancreas response to ingestion of food. In some instances, administration of an incretin mimetic in combination with any of the compounds described herein lowers blood and/or plasma glucose levels. Examples of incretin mimetics include and are not limited to exenatide (Byetta®). One currently used therapy for the treatment of diabetes is a subcutaneous injection of exenatide (Byetta®).

In some embodiments, the additional therapeutic agent is a thiazolidinedione. In some instances thiazolidinediones reverse insulin resistance and lower blood and/or plasma glucose levels. Examples of thiazolidinediones include and are not limited to Rosiglitazone (Avandia), Pioglitazone (Actos), Troglitazone (Rezulin), MCC-555, rivoglitazone, ciglitazone or the like.

In some embodiments, the additional therapeutic agent is an enteroendocrine peptide. In some embodiments, enteroendocrine peptides reverse insulin resistance and lower blood and/or plasma glucose levels. Examples of enteroendocrine peptides that are administered as additional therapeutic agents include and are not limited to GLP-1 or GLP-1 analogs such as Taspoglutide® (Ipsen), or the like.

In specific embodiments, the additional therapeutic agent inhibits degradation of L-cell enteroendocrine peptides. In certain embodiments, the additional therapeutic agent is a DPP-IV inhibitor. DPP-IV inhibitors suitable for use with the methods described herein include and are not limited to (2S)-1-{2-[(3-hydroxy-1-adamantyl)amino]acetyl}pyrrolidine-2-carbonitrile (vildagliptin), (3R)-3-amino-1-[9-(trifluoromethyl)-1,4,7,8-tetrazabicyclo[4.3.0]nona-6,8-dien-4-yl]-4-(2,4,5-trifluorophenyl)butan-1-one (sitagliptin), (1S,3S,5S)-2-[(2S)-2-amino-2-(3-hydroxy-1-adamantyl)acetyl]-2-azabicyclo[3.1.0]hexane-3-carbonitrile (saxagliptin), and 2-({6-[(3R)-3-aminopiperidin-1-yl]-3-methyl-2,4-dioxo-3,4-dihydropyrimidin-1(2H)-yl}methyl)benzonitrile (alogliptin). Another therapy that is current standard of care for the treatment of diabetes is metformin, or a combination of metformin and sitagliptin (Janumet®).

In some embodiments, the particular choice of compounds depends upon the diagnosis of the attending physicians and their judgment of the condition of the individual and the appropriate treatment protocol. The compounds are optionally administered concurrently (e.g., simultaneously, essentially simultaneously or within the same treatment protocol) or sequentially, depending upon the nature of the disease, disorder, or condition, the condition of the individual, and the actual choice of compounds used. In certain instances, the determination of the order of administration, and the number of repetitions of administration of each therapeutic agent during a treatment protocol, is based on an evaluation of the disease being treated and the condition of the individual.

In some embodiments, therapeutically-effective dosages vary when the drugs are used in treatment combinations. Methods for experimentally determining therapeutically-effective dosages of drugs and other agents for use in combination treatment regimens are described in the literature.

In some embodiments of the combination therapies described herein, dosages of the co-administered compounds vary depending on the type of co-drug employed, on the specific drug employed, on the disease or condition being treated and so forth. In addition, when co-administered with one or more biologically active agents, the compound provided herein is optionally administered either simultaneously with the biologically active agent(s), or sequentially. In certain instances, if administered sequentially, the attending physician will decide on the appropriate sequence of therapeutic compound described herein in combination with the additional therapeutic agent.

The multiple therapeutic agents are optionally administered in any order or even simultaneously. If simultaneously, the therapeutic agents are optionally provided in a single, unified form, or in multiple forms (by way of example only, either as a single pill or as two separate pills). In certain instances, one of the therapeutic agents is optionally given in multiple doses. In other instances, both are optionally given as multiple doses. If not simultaneous, the timing between the multiple doses is any suitable timing, e.g., from more than zero weeks to less than four weeks. In addition, the combination methods, compositions and formulations are not to be limited to the use of only two agents; the use of multiple therapeutic combinations are also envisioned (including two or more compounds described herein).

In certain embodiments, a dosage regimen to treat, prevent, or ameliorate the condition(s) for which relief is sought, is modified in accordance with a variety of factors. These factors include the disorder from which the subject suffers, as well as the age, weight, sex, diet, and medical condition of the subject. Thus, in various embodiments, the dosage regimen actually employed varies and deviates from the dosage regimens set forth herein.

In some embodiments, the pharmaceutical agents which make up the combination therapy described herein are provided in a combined dosage form or in separate dosage forms intended for substantially simultaneous administration. In certain embodiments, the pharmaceutical agents that make up the combination therapy are administered sequentially, with either therapeutic compound being administered by a regimen calling for two-step administration. In some embodiments, two-step administration regimen calls for sequential administration of the active agents or spaced-apart administration of the separate active agents. In certain embodiments, the time period between the multiple administration steps varies, by way of non-limiting example, from a few minutes to several hours, depending upon the properties of each pharmaceutical agent, such as potency, solubility, bioavailability, plasma half-life and kinetic profile of the pharmaceutical agent.

In some embodiments, the methods herein comprise administration of a composition described herein and a physical activity regimen. The physical activity regimen can be an exercise regimen. The physical activity regimen can be recommended to the subject by, e.g., a caregiver, or can be undertaken by the subject under the subject's own initiative. The physical activity regimen can comprise one or more episodes or bouts of any kind of physical activity or exercise, including, by way of example only, walking, power walking, hiking, backpacking, running, jogging, freerunning, parkour, biking, swimming, strolling, treadmilling, spinning, rowing, yoga, zumba, weightlifting, dancing, gymnastics, martial arts, track and field activities, athletic activity, sports such as, e.g., football, baseball, softball, cricket, kickball, dodgeball, soccer, basketball, hockey, ice skating, rollerskating, rollerblading, skateboarding, surfing, bowling, skiing, polo, water polo, lacrosse, snowboarding, rugby, wrestling, boxing, aerobatics, archery, fencing, badminton, tennis, table tennis, squash, diving, Frisbee, Ultimate Frisbee, climbing, e.g., rock climbing, billiards, horseback riding, golf, orienteering, circus arts such as, e.g., trampolining, trapeze, contortion, juggling, aerial fabrics, and the like. An episode or bout of physical activity can be undertaken for a length of time, e.g., 1-10 minutes, 5-20 minutes, 15-30 minutes, 30-60 minutes (1 hours), 2 hours, 4 hours, 8 hours, 12 hours, 24 hours, or more than 24 hours. A bout of physical activity can be less than 30 minutes. The subject can engage in one bout of physical activity per month, per week, 2 bouts per week, 3 bouts per week or more, one bout of activity a day, twice a day, or more than twice a day. The physical activity regimen can comprise, by way of example only, 1 bout of physical activity per day, wherein a bout of physical activity is for, e.g., 20 minutes. Administration of a composition as described herein in combination with a physical activity regimen can have synergistic beneficial effects on the subject, e.g., synergistic therapeutic effects.

The administration of a composition described herein, such as a combination composition, to a subject can allow for the regulation or maintenance of the subject's energy metabolism. The regulation or maintenance of energy metabolism can allow for a subject to experience a number of beneficial effects. These beneficial effects include a reduction in weight, a reduction in adipose tissue, an increase in fatty acid oxidation, an increase in insulin sensitivity, a decrease in oxidative stress, and/or a decrease in inflammation. Compared to a baseline prior to treatment, these effects can result in an improvement of about or greater than about 5, 10, 15, 20, 30, 40, 50, 75, 100, 125, 150, 200, 250, 300, 400, or 500%. Alternatively, administration of a composition described herein can allow for maintenance of the subject's weight, amount of adipose tissue, amount of fatty acid oxidation, level of insulin sensitivity, oxidative stress level, and/or level of inflammation. These amounts and/or levels can be maintained within 0, 1, 5, or 10% of the amounts and/or levels at the initiation of administration.

Another aspect of the invention provides for achieving desired effects in one or more subjects after administration of a combination composition described herein for a specified time period.

After a period of 6 weeks of administration of the composition, a combination composition comprising (a) a dosing level of a PDE 5 inhibitor and a dosing level of HMB or (b) a dosing level of a PDE inhibitor, e.g., a PDE 5 inhibitor and a dosing level of leucine (e.g., free leucine), can reduce weight gain in the one or more subjects by at least about 10, 15, 20, or 20.5%. The p-value can be less than 0.05 (e.g. less than about 0.05, 0.03, 0.02, 0.01, 0.001, 0.0001, or lower). The one or more subjects treated with the same dosing level of one of the components (sildenafil, icariin, resveratrol, leucine, or HMB) may have insignificant weight reduction, or a weight reduction that is less than about 0, 5, or 10%.

After a period of 2 weeks of administration, a composition comprising (a) a dosing level of PDE inhibitor, e.g., a PDE 5 inhibitor and a dosing level of HMB or (b) a dosing level of resveratrol and a dosing level of leucine (e.g., free leucine), can increase whole body fat oxidation in the one or more subjects by at least about 10, 15, or 20%. The p-value can be less than 0.05 (e.g. less than about 0.05, 0.03, 0.02, 0.01, 0.001, 0.0001, or lower). The increase in whole body fat oxidation can be sustained while the subjects are administered the composition, or for a period of at least 2, 4, 6, 10, 13, 26, or 52 weeks. The one or more subjects treated with the same dosing level of one of the components (sildenafil, icariin, resveratrol, leucine, or HMB) may have insignificant increase in whole body fat oxidation, or an increase in whole body fat oxidation that is less than about 0, 5, or 10%.

After a period of 2 weeks of administration, a composition comprising (a) a dosing level of a PDE inhibitor, e.g., a PDE 5 inhibitor and a dosing level of HMB or (b) a dosing level of resveratrol and a dosing level of leucine (e.g., free leucine), can increase the thermic effect of food in the one or more subjects by at least about 10, 15, 17, or 20%. The p-value can be less than 0.05 (e.g. less than about 0.05, 0.03, 0.02, 0.01, 0.001, 0.0001, or lower). The increase in the thermic effect of food can be sustained while the subjects are administered the composition, or for a period of at least 2, 4, 6, 10, 13, 26, or 52 weeks. The one or more subjects treated with the same dosing level of one of the components (sildenafil, icariin, resveratrol, leucine, or HMB) may have insignificant increase the thermic effect of food, or an increase the thermic effect of food that is less than about 0, 5, or 10%.

After a period of 2 weeks of administration, a composition comprising (a) a dosing level of a PDE inhibitor, e.g., a PDE 5 inhibitor and a dosing level of HMB or (b) a dosing level of a PDE inhibitor, e.g., a PDE 5 inhibitor and a dosing level of leucine (e.g., free leucine), can increase total energy expenditure in the one or more subjects by at least about 10, 15, 17, or 20%. The p-value can be less than 0.05 (e.g. less than about 0.05, 0.03, 0.02, 0.01, 0.001, 0.0001, or lower). The increase total energy expenditure can be sustained while the subjects are administered the composition, or for a period of at least 2, 4, 6, 10, 13, 26, or 52 weeks. The one or more subjects treated with the same dosing level of one of the components (sildenafil, icariin, resveratrol, leucine, or HMB) may have insignificant increase total energy expenditure, or an increase total energy expenditure that is less than about 0, 5, or 10%.

The administration of a composition described herein, such as a combination composition, to a subject can allow for the regulation or maintenance of the subject's energy metabolism. The regulation or maintenance of energy metabolism can allow for a subject to experience a number of beneficial effects. These beneficial effects include a reduction in weight, a reduction in adipose tissue, an increase in fatty acid oxidation, an increase in browning of adipose tissue (as indicated by one or more indicia of fat cell browning), an increase in insulin sensitivity, a decrease in oxidative stress, and/or a decrease in inflammation. Compared to a baseline prior to treatment, these effects can result in an improvement of about or greater than about 5%, 10%, 15%, 20%, 30%, 40%, 50%, 75%, or more. In some embodiments, compared to a baseline prior to treatment, these effects can result in an improvement of about or greater than about 100%, 125%, 150%, 200%, 250%, 300%, 400%, 500%, or more. Alternatively, administration of a composition described herein can allow for maintenance of the subject's weight, amount of adipose tissue, amount of fatty acid oxidation, level of insulin sensitivity, oxidative stress level, and/or level of inflammation. These amounts and/or levels can be maintained within about 0%, 1%, 5%, or 10% of the amounts and/or levels at the initiation of administration.

The invention provides for a method of treating subjects, comprising identifying a pool of subjects amenable to treatment. The identifying step can include one or more screening tests or assays. For example, subjects that are identified as diabetic, as having insulin resistance, or that have above average or significantly greater than average body mass indices and/or weight can be selected for treatment. The identifying step can include a genetic test that identifies one or more genetic variants that suggest that the subject is amenable to treatment. The identified subjects can then be treated with one or more compositions described herein. In one embodiment, the invention provides a method of regulating energy metabolism comprising: (a) identifying a subject having or prone to obesity or diabetes; and (b) administering to the subject a composition described herein, for example any composition of originally filed claims 1-29. For example, they may be treated with a combination composition comprising a selective PDE inhibitor, such as a PDE 5 inhibitor, and a branched-chain amino acid.

The invention also provides for methods of manufacturing the compositions described herein. In some embodiments, the manufacture of a composition described herein comprises mixing or combining two or more components. These components can include a selective PDE inhibitor, including but not limited to PDE 5 inhibitor in combination with leucine (e.g., free leucine) and/or leucine metabolites. The composition can further include additional a sirtuin or AMPK pathway activator (such as a polyphenol or polyphenol precursor like resveratrol, chlorogenic acid, caffeic acid, cinnamic acid, ferulic acid, EGCG, piceatannol, or grape seed extract, or another agent like quinic acid and fucoxanthin. In some embodiments, the sirtuin activator is a polyphenol. In other embodiments, the sirtuin activator is a polyphenol precursor. The amount or ratio of components can be that as described herein.

In some embodiments, the compositions can be combined or mixed with a pharmaceutically active agent other than a PDE-5 inhibitor, a carrier, and/or an excipient. Examples of such components are described herein. The combined compositions can be formed into a unit dosage as tablets, capsules, gel capsules, slow-release tablets, or the like.

In some embodiments, the composition is prepared such that a solid composition containing a substantially homogeneous mixture of the one or more components is achieved, such that the one or more components are dispersed evenly throughout the composition so that the composition may be readily subdivided into equally effective unit dosage forms such as tablets, pills and capsules.

Kits

The invention also provides kits. The kits include one or more compositions described herein, in suitable packaging, and written material that can include instructions for use, discussion of clinical studies, listing of side effects, and the like. Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. The kit may further contain another agent. In some embodiments, the compound of the present invention and the agent are provided as separate compositions in separate containers within the kit. In some embodiments, the compound of the present invention and the agent are provided as a single composition within a container in the kit. Suitable packaging and additional articles for use (e.g., measuring cup for liquid preparations, foil wrapping to minimize exposure to air, and the like) are known in the art and may be included in the kit. Kits described herein can be provided, marketed and/or promoted to health providers, including physicians, nurses, pharmacists, formulary officials, and the like. Kits may also, in some embodiments, be marketed directly to the consumer.

In some embodiments, a kit can comprise a multi-day supply of unit dosages. The unit dosages can be any unit dosage described herein. The kit can comprise instructions directing the administration of the multi-day supply of unit dosages over a period of multiple days. The multi-day supply can be a one-month supply, a 30-day supply, or a multi-week supply. The multi-day supply can be a 90-day, 180-day, 3-month or 6-month supply. The kit can include packaged daily unit dosages, such as packages of 1, 2, 3, 4, or 5 unit dosages. The kit can be packaged with other dietary supplements, vitamins, and meal replacement bars, mixes, and beverages.

In some embodiments, a kit can further comprise a wearable activity monitor. The wearable activity monitor can monitor physical and/or ambulatory activity via a pedometer, accelerometer, or Exemplary wearable activity monitors include, e.g.; a Fitbit®, Jawbone UP®, LarkLife™, Nike FuelBand, Striiv Play, BodyMedia Fit-Core, among others. Such wearable activity monitors are described in U.S. Pat. Nos. 8,403,845; 8,398,546; 8,382,590; 8,369,936; 8,275,635; 8,157,731; 8,073,707; 7,959,567; 7,689,437; 7,502,643; 7,285,090; 7,261,690; 7,153,262; 7,020,508; 6,605,038; 6,595,929; 6,527,711; 8,562,489; 8,517,896; 8,469,862; 8,408,436; 8,370,549; 8,088,044; 8,088,043, and US Patent Application Publication Nos. 20130158369 and 20130151196, all of which are hereby incorporated by reference. Such kits can further comprise instructions for the subject to engage in a physical activity regimen in addition to instructions for use of the composition. Such kits can further comprise instructions for use of the wearable activity monitors. Such kits can also comprise wearable activity monitor accessories, such as, e.g., a charger, and/or a port or wireless for communicating data from the activity monitor to a computer or server.

EXAMPLES

Example 1—PDE 1 Inhibitors for Regulating Energy Metabolism

Vinopocetine, which is a PDE 1 inhibitor, was tested in combination with leucine, HMB, and resveratrol for its effects on energy metabolism. Dose-response indicates that concentrations of 0.1 nM or below of vinopocetine exert no effect; accordingly, this was the concentration used in these experiments. Vinopocetine exhibited no synergy with either leucine (0.5 mM) or HMB (5 µM) with respect to either fat oxidation or glucose utilization, although it did exhibit a synergistic effect with low-dose resveratrol 200 nM), resulting in a 70% increase in glucose utilization in adipocytes (p=0.03).

Example 2—PDE 3 Inhibitors for Regulating Energy Metabolism

Two PDE 3 inhibitors were studied, amrinone and cilostamide, in combination with leucine and HMB for their effects on energy metabolism. Dose-response indicates that concentrations of 10 nM or below for either PDE 3 inhibitor exert no effect; accordingly, this concentration for the PDE 3 inhibitors was used in these experiments. Amrinone exerted no significant synergy with either leucine or HMB. However, combining either leucine (0.5 mM) or HMB (5 µM) with cilostamide resulted in a 92% increase in fat oxidation (p<0.05) in muscle cells and a 58% increase in adipocytes (p<0.05). The cilostamide-HMB blend synergistically increased glucose utilization by 202% in muscle cells (p=0.024) and by 83% in adipocytes (p=0.05), while the cilostamide-leucine blend exerted no effect.

Example 3—PDE 4 Inhibitors for Regulating Energy Metabolism

Two PDE 4 inhibitors were studied, rolipram and YM796, in combination with leucine and HMB for their effects on energy metabolism. Dose-response indicate concentrations of 0.1 nM or below of rolipram and YM796 exert no effect; accordingly, this was the concentration used in these experiments. There was no synergistic effect of rolipram with leucine, HMB or resveratrol with respect to fat oxidation, glucose utilization or AMPK activity in muscle cells; although rolipram activated AMPK phosphorylation, this effect was not augmented by the presence of either leucine or HMB. However, fat oxidation synergy was evident in adipocytes, with a 125% increase in fat oxidation in response to the rolipram-leucine combination (p=0.026) and a 63% increase in response to the rolipram-HMB combination. However, no synergy was found for glucose utilization or AMPK activation.

Example 4—PDE 5 Inhibitors for Regulating Energy Metabolism

Cells were treated with combinations of sildenafil (1 nM), icariin (1 nM), leucine (0.5 mM), HMB (5 µM), and resveratrol (200 nM). Treatment with 0.5 mM leucine corresponds to a circulating level of the same molarity achieved by administering about 1,125 mg of dietary leucine to a human subject. Treatment with 0.25 mM leucine corresponds to a circulating level of the same molarity achieved by administering about 300 mg of dietary leucine to a human subject. Treatment with 1 nM sildenafil corresponds to a circulating level of the same molarity achieved by administering about 0.2 mg of dietary sildenafil to a human subject. Treatment with 1 nM sildenafil corresponds to a circulating level of the same molarity achieved by administering about 0.1 mg of dietary sildenafil to a human subject.

Figure 2:
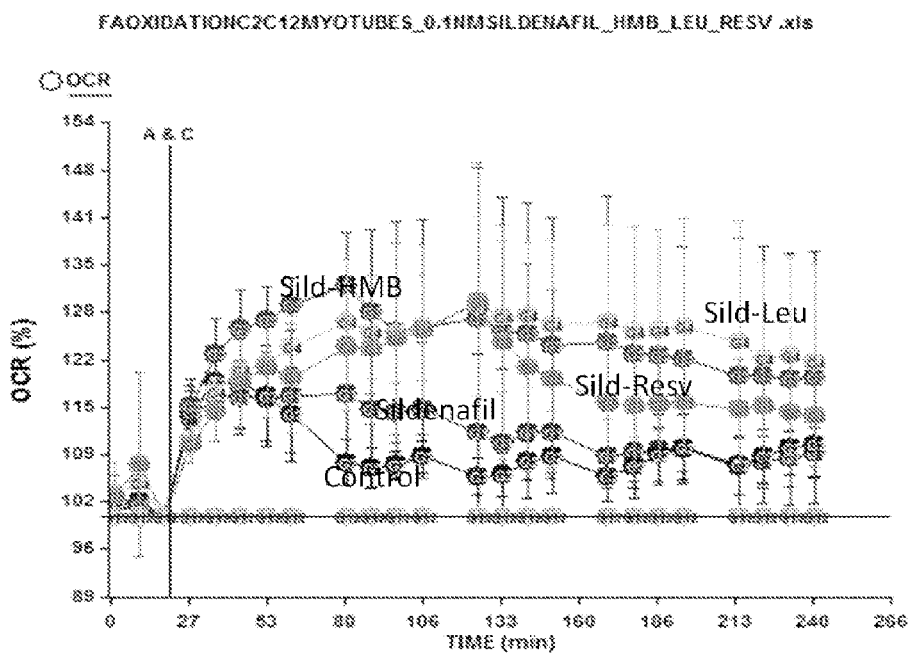
FIG. 2 shows the interactive effects of sildenafil with HMB, leucine and resveratrol on fatty acid oxidation in C2C12 myotubes. Fatty acid oxidation was measured as $O_2$ consumption response to palmitate injection and is expressed as % change from pre-injection baseline. The vertical line shows the time of palmitate injection; data points to the left of this line are baseline measurements and those to the right of the line show the $O_2$ consumption response.
Figure 3:
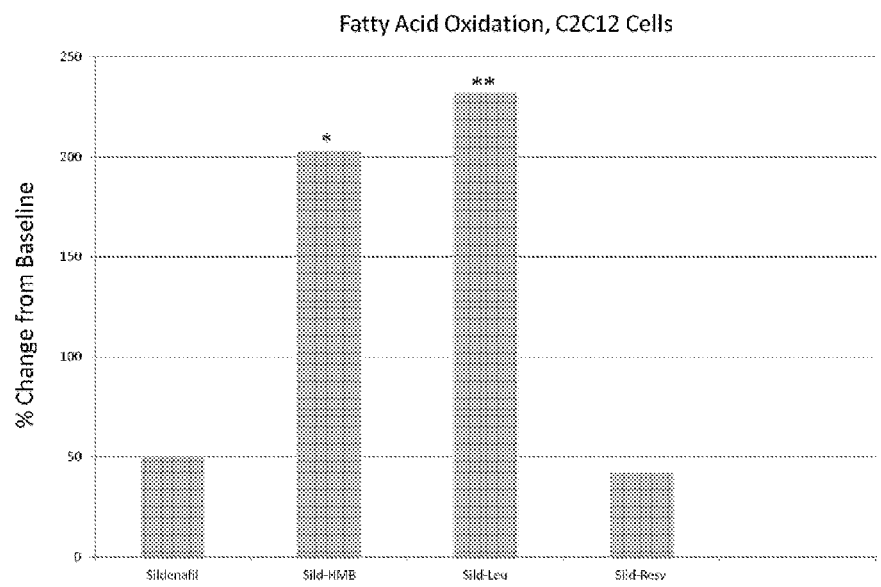
FIG. 3 shows the interactive effects of sildenafil with HMB, leucine and resveratrol on fatty acid oxidation in C2C12 myotubes. Data expressed as % change from control value. *p=0.013; **p=0.015.

Sildenafil dose-response curves indicate concentrations below 1 nM exert no effect; accordingly, this was the concentration used in synergy experiments. This is approximately 1% of the peak plasma concentration (~100 nM) achieved in response to a low dose of the drug (20 mg). Treatment of C2C12 myotubes with Sildenafil alone resulted in a fatty acid oxidation change from baseline of about 50%. Treatment with leucine alone stimulates fatty acid oxidation to 73%, p<0.05. Sildenafil at this concentration exerted a significant synergy in stimulating myotube fat oxidation with both HMB (203% increase, p=0.003) and leucine (232% increase, p=0.015), but exhibited no interaction with resveratrol in muscle cells (FIG. 2 and FIG. 3).

Figure 4:
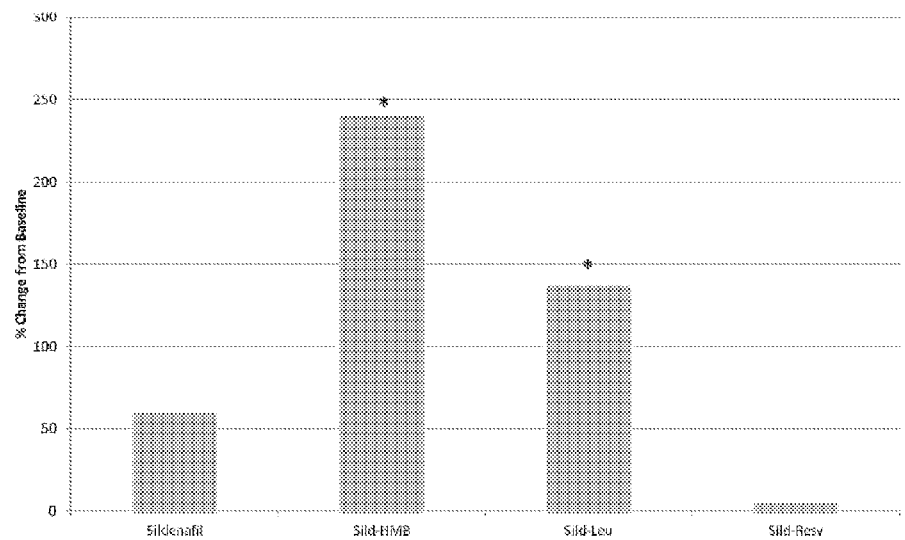
FIG. 4 shows the interactive effects of sildenafil with HMB, leucine and resveratrol on fatty acid oxidation in 3T3-L1 adipocytes. Data expressed as % change from control value.*p<0.05.

In 3T3-L1 adipocytes, treatment with leucine increases fatty acid oxidation to 27%, p<0.05 and treatment with HMB stimulates fatty acid oxidation to 29%, p<0.05. As with C2C12 cells, sildenafil-leucine and sildenafil-HMB synergistically increased fat oxidation in adipocytes by 137% and 240%, respectively (p<0.05; FIG. 4). Addition of resveratrol (200 nM) to either the sildenafil-leucine or sildenafil-HMB exerted no additional effect and was not significantly different from these mixtures in the absence of resveratrol.

Figure 5:
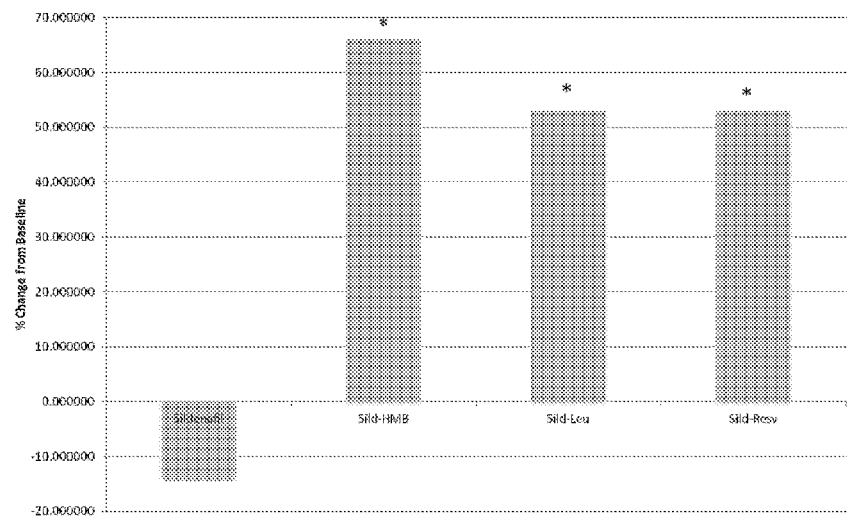
FIG. 5 shows the interactive effects of sildenafil with HMB, leucine and resveratrol on glucose utilization in C2C12 myotubes. Glucose utilization was measured as extracellular acidification response to glucose injection. *p=0.04.
Figure 6:
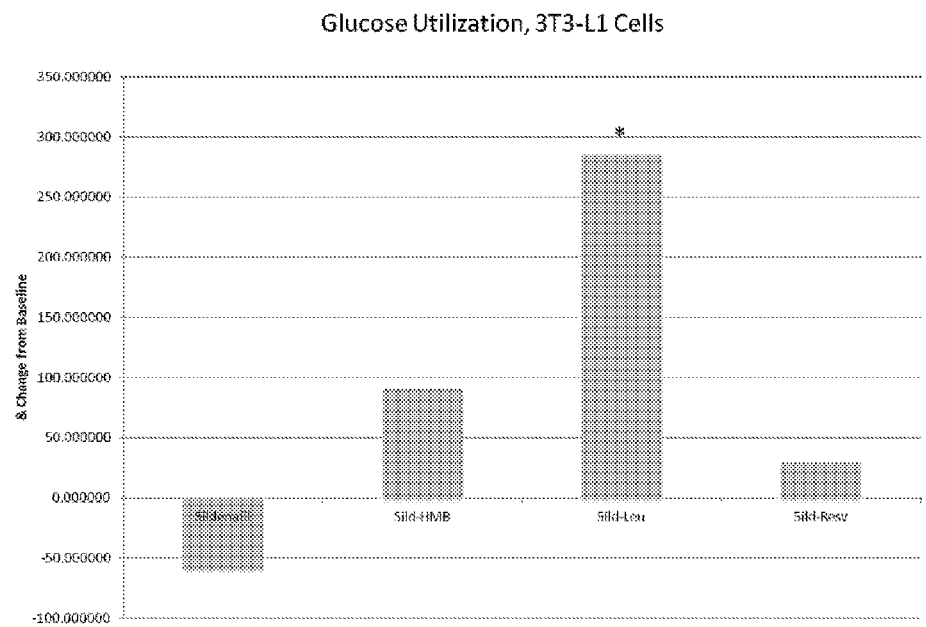
FIG. 6 shows the interactive effects of sildenafil with HMB, leucine and resveratrol on glucose utilization in 3T3-L1 adipocytes. Glucose utilization was measured as extracellular acidification response to glucose injection. *p=0.05.

Sildenafil also exhibited synergy with leucine and HMB in stimulating glucose utilization in both myotubes and adipocytes. Treatment of C2C12 myotubes with leucine alone increases glucose utilization to 9.3%. Sildenafil-leucine and sildenafil-HMB synergistically augmented myotube glucose utilization by 53 and 66%, respectively (p=0.04, FIG. 5), and sildenafil also exhibited synergy with resveratrol to produce a similar augmentation (53%, p=0.04). Treatment with leucine stimulates glucose utilization in 3T3-L1 cells to 48.6%, p<0.05. In 3T3-L1 adipocytes, sildenafil-leucine increased glucose utilization by 285% (p=0.05, FIG. 6), while neither HMB nor resveratrol exerted any significant synergy with sildenafil.

Figure 7:
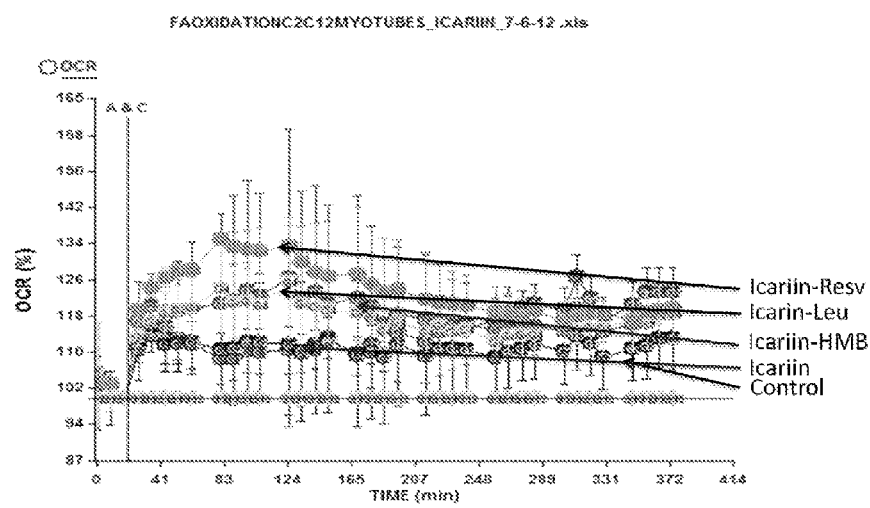
FIG. 7 shows the interactive effects of icariin with HMB, leucine and resveratrol on fatty acid oxidation in C2C12 myotubes. Fatty acid oxidation was measured as $O_2$ consumption response to palmitate injection and is expressed as % change from pre-injection baseline. The vertical line shows the time of palmitate injection; data points to the left of this line are baseline measurements and those to the right of the line show the $O_2$ consumption response.
Figure 8:
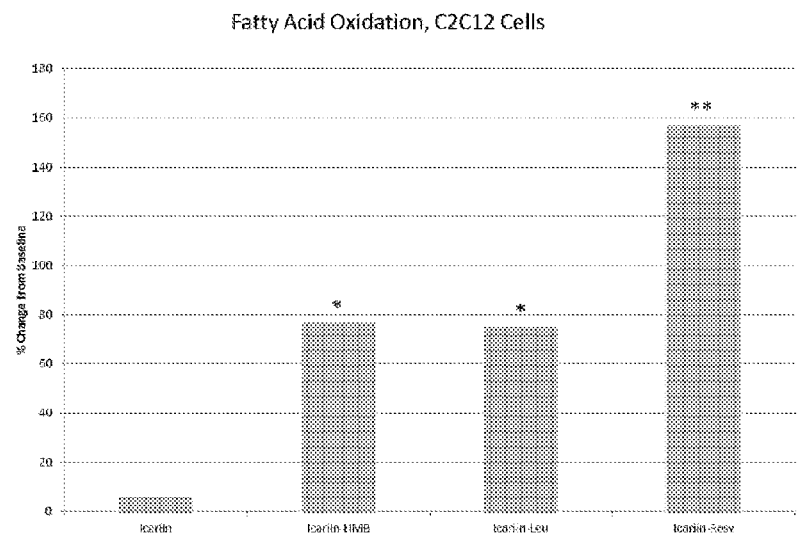
FIG. 8 shows the interactive effects of icariin with HMB, leucine and resveratrol on fatty acid oxidation in C2C12 myotubes. Data expressed as % change from control value. *p=0.03; **p=0.002.
Figure 9:
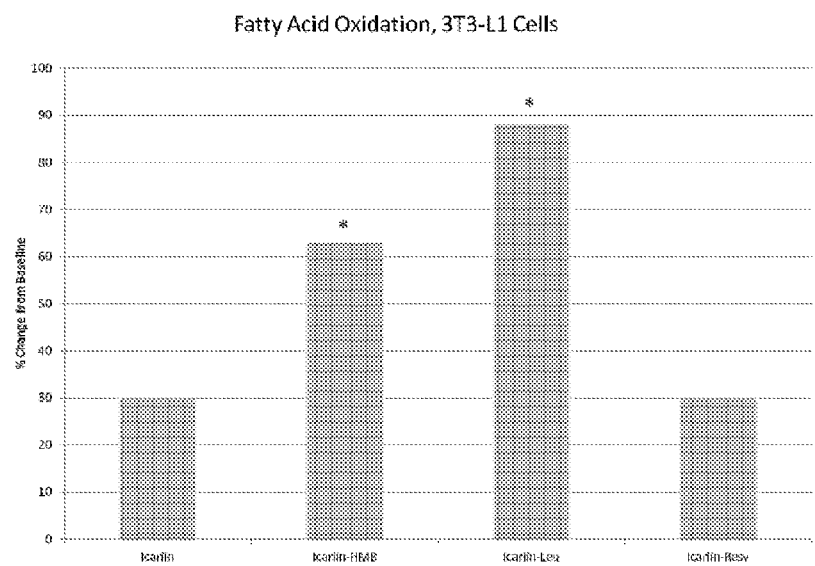
FIG. 9 shows the interactive effects of icariin with HMB, leucine and resveratrol on fatty acid oxidation in 3T3-L1 adipocytes. Data expressed as % change from control value. *p<0.05.

Icariin is a naturally occurring flavonol with significant PDE 5 inhibitory activity. Dose-response curves indicate icariin concentrations below 1 nM exert no effect; accordingly, this was the concentration used in synergy experiments. Treatment of C2C12 myotubes with leucine alone stimulates fatty acid oxidation to 73%, p<0.05. Icariin at this concentration exerted a significant synergy in stimulating C2C12 myotube fat oxidation with both HMB (75% increase) and leucine (77% increase) (p=0.03, FIG. 7 and FIG. 8), while resveratrol exerted an independent synergistic effect (157% increase, p=0.002, FIG. 8). Similar data were obtained in adipocytes (p<0.05; FIG. 9); however, icariin did not exhibit significant synergy with respect to glucose utilization.

Figure 10:
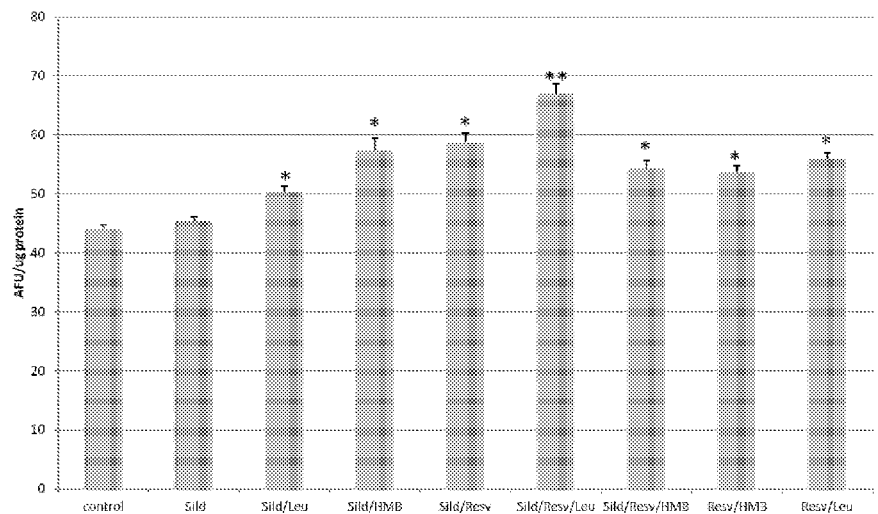
FIG. 10 shows the interactive effects of sildenafil with HMB, leucine and resveratrol on nitric oxide production in C2C12 myotubes. *p<0.0001 vs. control; **p=0.0003 vs. all other treatments.
Figure 11:
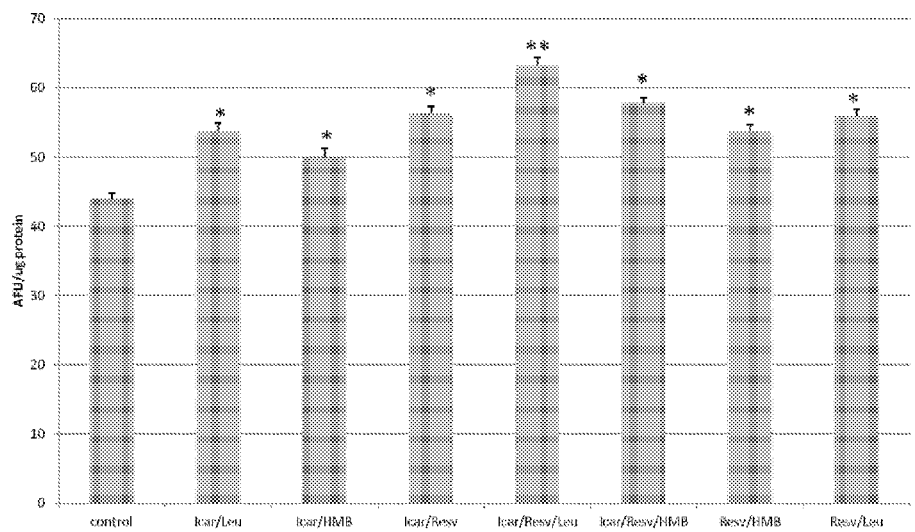
FIG. 11 shows the interactive effects of icariin with HMB, leucine and resveratrol on nitric oxide production in C2C12 myotubes. p<0.0001 vs. control; **p=0.00013 vs. all other treatments.

There were significant synergistic interactions between both sildenafil and icariin with leucine, HMB, resveratrol, and combinations thereof on nitric oxide production. FIG. 10 shows the interaction between sildenafil and leucine, HMB and resveratrol, and FIG. 11 shows the interaction between icariin and leucine, HMB and resveratrol. Leucine, HMB and resveratrol each interacted with low dose sildenafil (1 nM) to produce modest, significant increases in nitric oxide production (15-30% increases, p<0.0001), while the combination of sildenafil, leucine and resveratrol produced a more robust response (52% increase, p=0.0003 vs. all other treatments, FIG. 10). Similar effects were noted with icariin, with leucine, HMB and resveratrol each interacting to elicit modest, significant effects (p<0.0001), with a more robust effect found with the combination of sildenafil, leucine and resveratrol (FIG. 11; p=0.00013).

Figure 12:
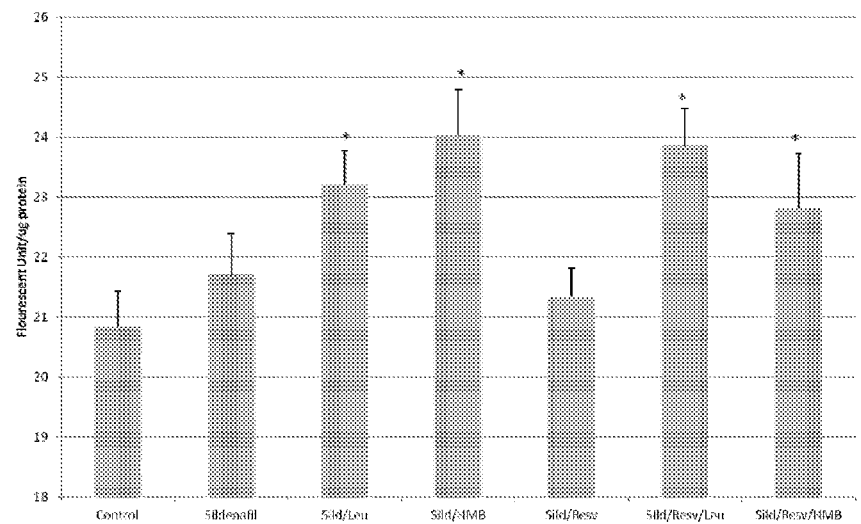
FIG. 12 shows the interactive effects of sildenafil with HMB, leucine and resveratrol on mitochondrial biogenesis, measured as mitochondrial mass, in C2C12 myotubes. *p<0.0001 vs. control; **p=0.0003 vs. all other treatments.
Figure 13:
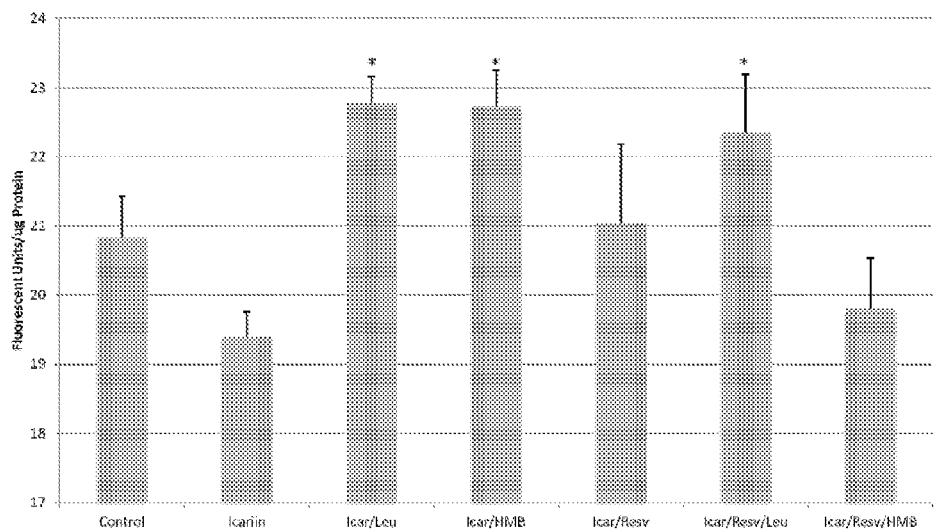
FIG. 13 shows the interactive effects of icariin (1 nM) with HMB (5 μM), leucine and resveratrol on mitochondrial biogenesis, measured as mitochondrial mass, in C2C12 myotubes. p<0.0001 vs. control; **p=0.00013 vs. all other treatments.

Nitric oxide has been demonstrated to regulate PGC1α and thereby stimulate mitochondrial biogenesis; accordingly, we evaluated the effects of sildenafil and icariin combinations with leucine, HMB and resveratrol on mitochondrial biogenesis, as measured mitochondrial biomass. C2C12 cells treated with leucine alone have a mitochondrial biomass of 22.05+/−0.4 AFU/µg protein, p<0.05, FIG. 12 demonstrates a significant synergy between sildenafil (1 nM) and either leucine or HMB, as leucine-sildenafil and leucine-HMB each stimulated significant increases in mitochondrial biomass (p<0.01), while there was no significant effect of resveratrol on this interaction. Similarly, icariin exhibited a significant synergy with both leucine and HMB to up regulate mitochondrial biogenesis (p<0.001), while resveratrol did not exhibit a significant interaction (FIG. 13).

The observed synergy between leucine/HMB and sildenafil in augmenting oxidative metabolism is non-obvious, as a recent report indicates that a closely related member of this drug class, Tadalafil (trade name Cialis) has been reported to suppress aerobic metabolism in the same cell system (C2C12 myotubes). However, chronic (12-week) administration of sildenafil resulted in increased energy expenditure, reduced weight and fat gain, and increased insulin sensitivity, although acute administration was without effect. Our data suggest that combining substantially lower concentrations than those used for treatment of erectile dysfunction with either leucine or HMB will be a useful therapeutic strategy for diabetes management. As an alternative to sildenafil, icariin is a naturally occurring flavonol found in plants of the Epimedium family (horny goat weed) which also has PDE5 inhibitory activity and exerts similar effects.

Example 5—In Vivo Effect of PDE 5 Inhibitors on Glycemia and Insulin Sensitivity The interactive effects of icariin, a flavanol with specific PDE5 inhibitory properties, on glycemia and insulin sensitivity were assessed in the diet-induced obese mouse, which can be used as a murine model of type 2 diabetes.

Methods

Figure 14:
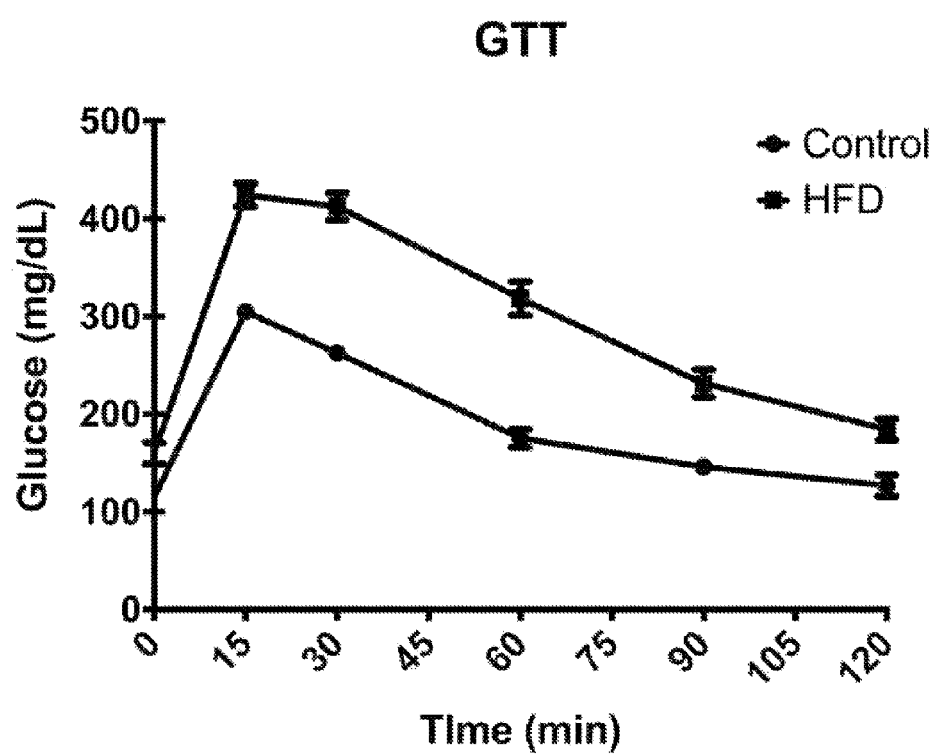
FIG. 14 shows results from an intraperitoneal glucose tolerance test in mice following six weeks on low or high fat diet.

Male C57/BL6 mice were placed on standard low-fat chow (control; 10% energy from fat) or high fat (60% energy from fat, Research Diets #D12492, Research Diets, Inc, New Brunswick, N.J.) at six weeks of age to induce insulin resistance. The mice on the high fat diet exhibited impaired glucose tolerance after 6 weeks of exposure, as compared to low fat diet mice (see FIG. 14).

The animals were then randomized to the following diets for an additional six weeks, with 10 animals per group: Low fat diet (LFD) control; High fat diet (HFD) control; HFD+ leucine (24 g/kg diet, a two-fold increase over control levels) 1 HFD+leucine (24 g/kg diet)+icariin (25 mg/kg diet). Previous published studies of icariin have demonstrated no effect of the selected level (25 mg/kg diet; ~4 mg/kg body weight).

Mice were fasted overnight (~16 hours) prior to measurement of fasting blood glucose, insulin and glucose tolerance. Glucose tolerance was determined following measurement of fasting glucose via intraperitoneal administration of glucose (1.2 g/kg body weight) followed by blood glucose measurement at 15, 30, 60, 90 and 120 minutes. Post-prandial glucose was measured within one hour of cessation of eating. Insulin tolerance was measured via an insulin tolerance test (ITT). Food was removed 4-6 hours prior to ITT, and baseline blood glucose measured. The mice were then injected intraperitoneally with insulin (1.2 U/kg body weight) and blood glucose was measured 15, 30, 60, 90 and 120 minutes following insulin injection. The homeostasis model assessment of insulin resistance ($HOMA_{IR}$) was used as a screening index of changes in insulin sensitivity. $HOMA_{IR}$ is calculated via standard formula from fasting plasma insulin and glucose as follows: $HOMA_{IR}$=[Insulin (uU/mL)×glucose (mM)]/22.5. The plasma glucose and insulin concentrations were measured using the Glucose Assay Kit from Biovision (Milpitas, Calif.) and the Insulin kit from Millipore (Billerica, Mass.), respectively. CRP levels in plasma were determined by ELISA (CRP: Life Diagnostics, West Chester, Pa.).

Data were analyzed via one-way analysis of variance; when ANOVA showed significant differences, means were separated via Tukey's multiple comparison test (Graphpad Prism, Version 6.0). p-values of less than 0.05 are generally considered statistically significant.

Results

Figure 15:
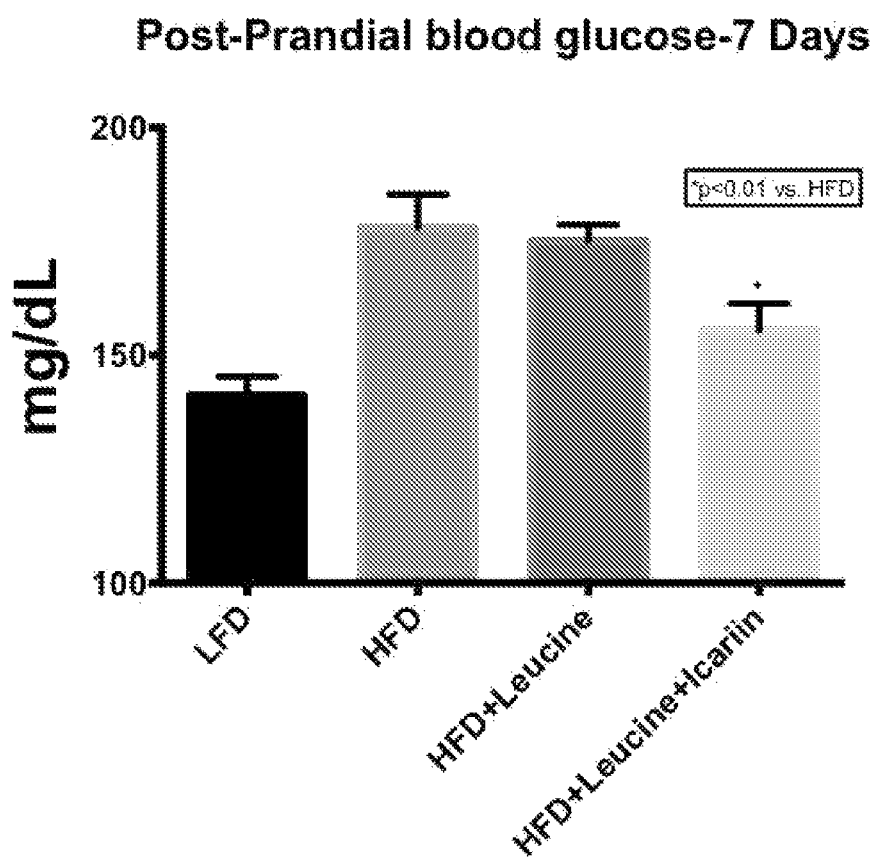
FIG. 15 shows effects of seven days of leucine or leucine+ icariin treatment on post-prandial blood glucose levels in high fat diet mice, as compared to untreated low fat diet mice.
Figure 16:
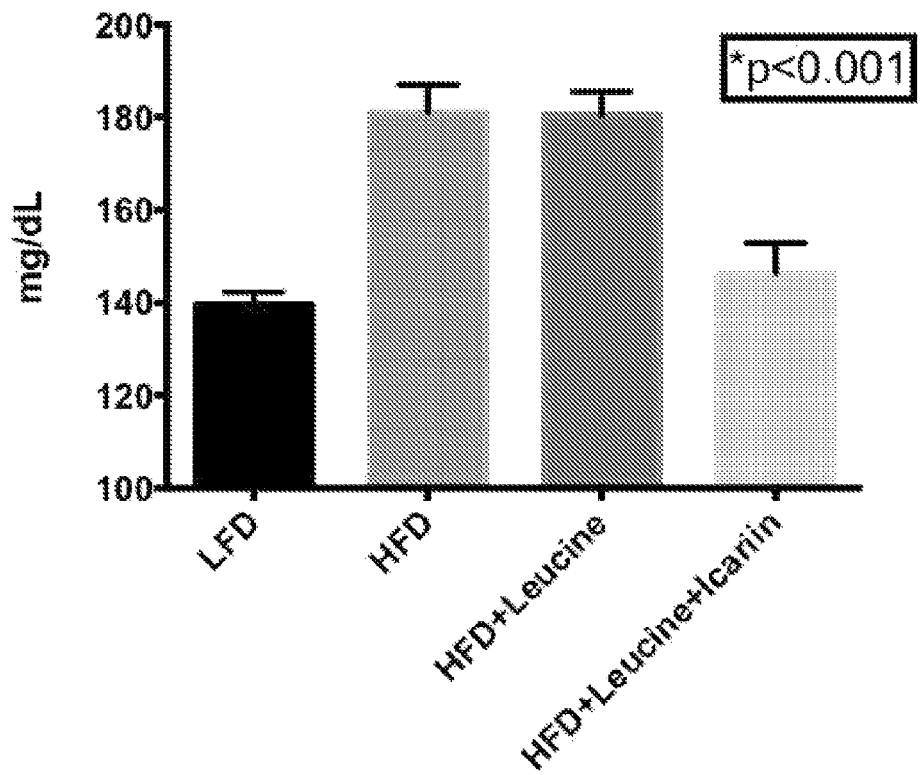
FIG. 16 shows effects of fourteen days of leucine or leucine+icariin treatment on post-prandial blood glucose levels in high fat diet mice, as compared to untreated low fat diet mice.

Post-prandial glucose was markedly elevated in response to the high fat diet by day 7 of treatment (FIG. 15). Although leucine exerted no independent effect on glucose, the combination of leucine and icariin caused a significant reduction of about 10% in post-prandial glucose after 7 day of treatment as compared to untreated HFD mice (p<0.01 vs. HFD, FIG. 15). This effect increased in magnitude after 14 days to about 20%, such that the leucine-icariin combination treatment in HFD mice reduced post-prandial glucose to levels found in the low-fat diet mice (p<0.001 vs. HFD, FIG. 16).

Figure 17:
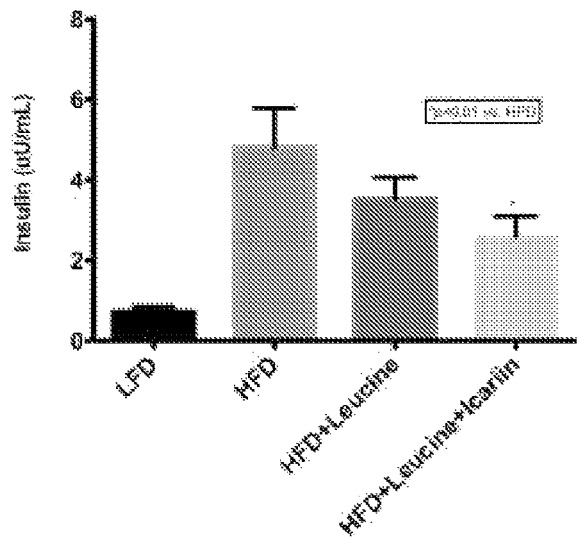
FIG. 17 shows effects of fourteen days of leucine or leucine+icariin treatment on post-prandial plasma insulin in high fat diet mice, as compared to untreated low fat diet mice.

Post-prandial insulin, or circulating insulin, levels were measured in all experimental groups following 14 days of treatment. HFD mice exhibited a ~5-fold elevation in circulating insulin as compared to the LFD mice (FIG. 17). However, 14-day treatment of HFD mice with insulin alone decreased circulating insulin by ~30% as compared to untreated HFD mice (FIG. 17). 14-day treatment of HFD mice with leucine and icariin further decreased circulating insulin levels by about 50% as compared to untreated HFD mice (p<0.01 vs. HFD, FIG. 17).

Figure 18:
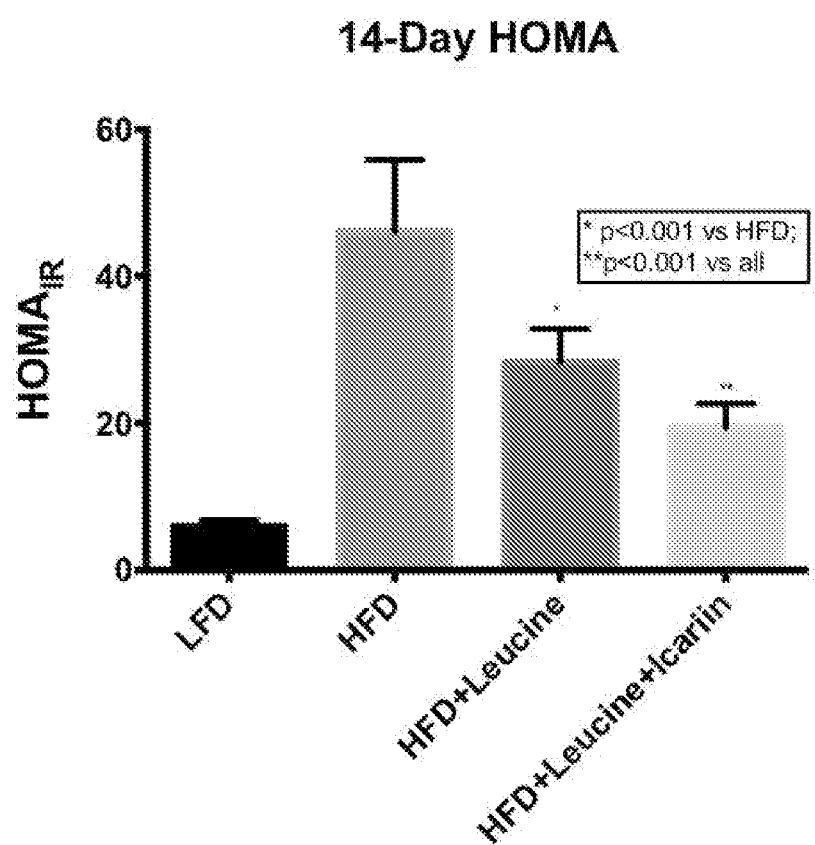
FIG. 18 show effects of fourteen days of leucine or leucine+icariin treatment on homeostatic assessment of insulin resistance measures in high fat diet mice, as compared to untreated low fat diet mice.

Insulin sensitivity was measured via Homeostatic Assessment of Insulin Resistance ($HOMA_{IR}$) in all experimental groups following 14 days of treatment. ($HOMA_{IR}$=insulin (uU/mL)×glucose (mM)/22.5). HFD mice exhibited a 10-fold elevation in $HOMA_{IR}$ as compared to LFD mice (FIG. 18). However, 14-day treatment of HFD mice with insulin alone decreased $HOMA_{IR}$ by ~40% as compared to untreated HFD mice (p<0.001 vs. HFD, FIG. 18). 14-day treatment of HFD mice with leucine and icariin further decreased $HOMA_{IR}$ levels by about 65% as compared to untreated HFD mice (p<0.001 vs. all, FIG. 18).

Figure 19:
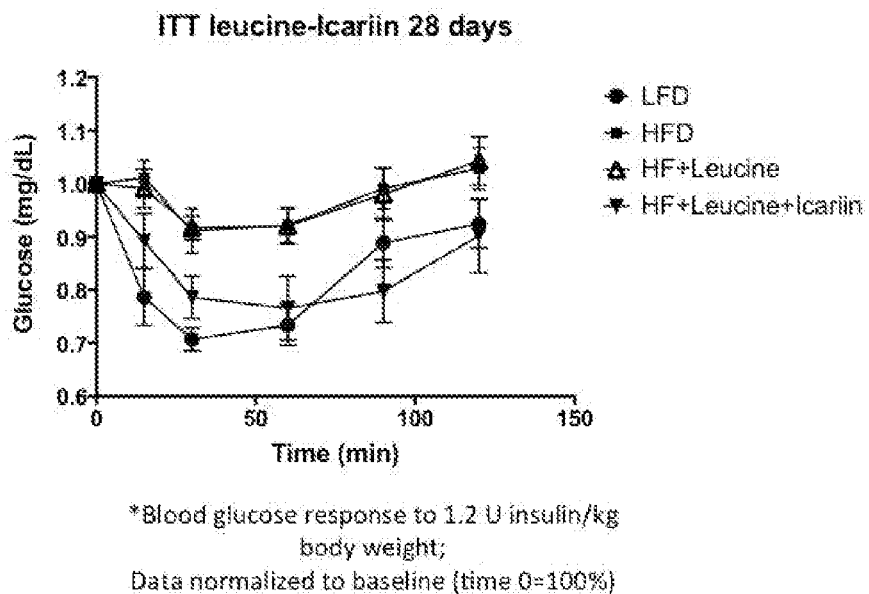
FIG. 19 shows blood glucose response to 1.2 U insulin/kg body weight following 28 days of leucine or leucine+icariin treatment in high fat diet mice, as compared to untreated low fat diet mice.
Figure 20:
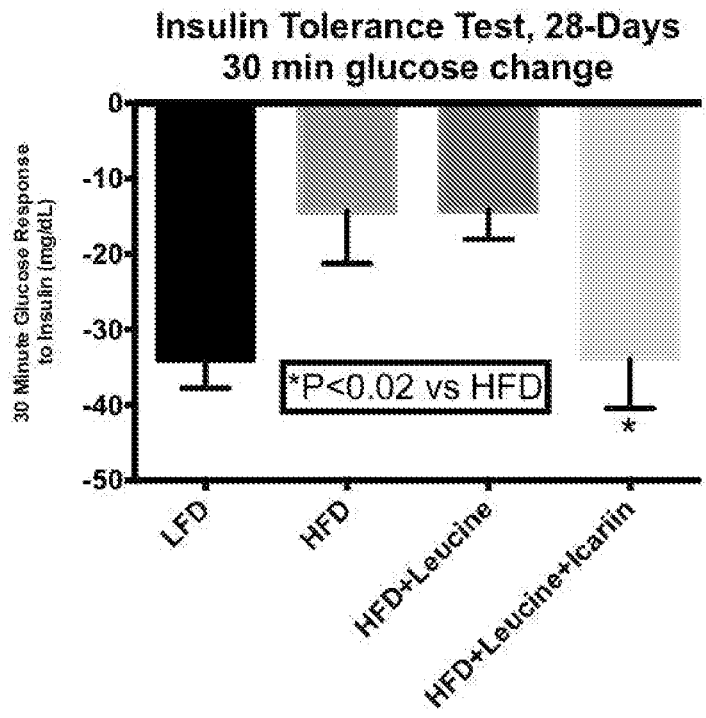
FIG. 20 shows the 30-minute blood glucose response to 1.2 U insulin/kg body weight following 28 days of leucine or leucine+icariin treatment in high fat diet mice, as compared to untreated low fat diet mice.

Insulin sensitivity was measured via insulin tolerance testing in all experimental groups following 28 days of treatment. As shown in FIG. 19, the addition of leucine and icariin to the high fat diet improved the response to insulin to a level that matched that found in the low fat diet. Since the maximum decrease in blood glucose was found at 30 minutes, statistical analysis was performed on the change in blood glucose at 30 minutes (FIG. 20). Analysis of the insulin tolerance test 30 minute time point shows that glucose clearance in HFD mice was reduced by about 50% as compared to LFD mice (FIG. 20). However, treatment of HFD mice with leucine and icariin fully rescued glucose clearance to levels found in the LFD mice, a two-fold change relative to HFD mice not treated with leucine and icariin (p<0.02 vs. HFD, FIG. 20). This analysis shows that the blunted response to insulin caused by the high fat diet was fully reversed by the addition of the leucine-icariin combination.

Figure 21:
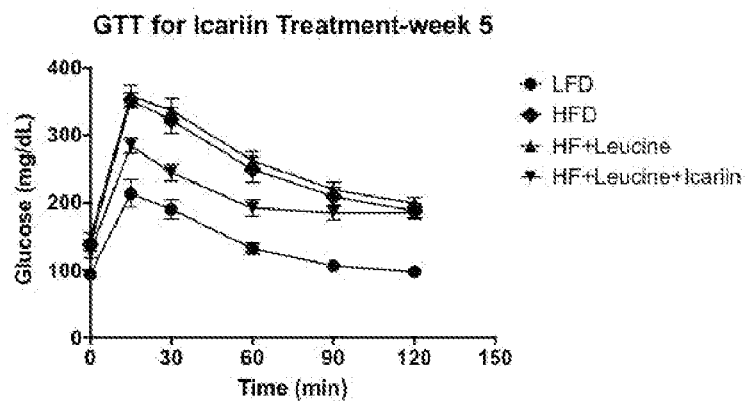
FIG. 21 shows results from a glucose tolerance test measured at 5 weeks of treatment with leucine or leucine+ icariin in high fat diet mice, as compared to untreated low fat diet mice.
Figure 22:
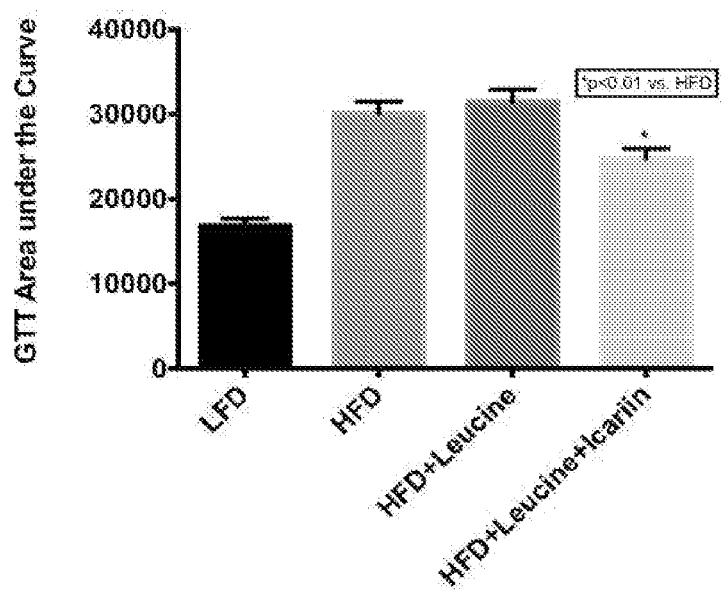
FIG. 22 shows the calculated integrated blood glucose response to glucose load over time obtained from the glucose tolerance test depicted in FIG. 21.
Figure 23:
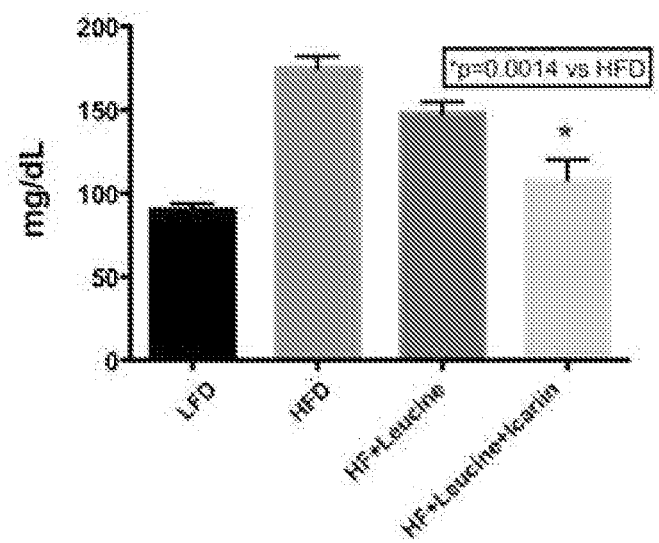
FIG. 23 shows fasting blood glucose levels following 6 weeks of treatment with leucine or leucine+icariin in high fat diet mice, as compared to untreated low fat diet mice.
Figure 24:
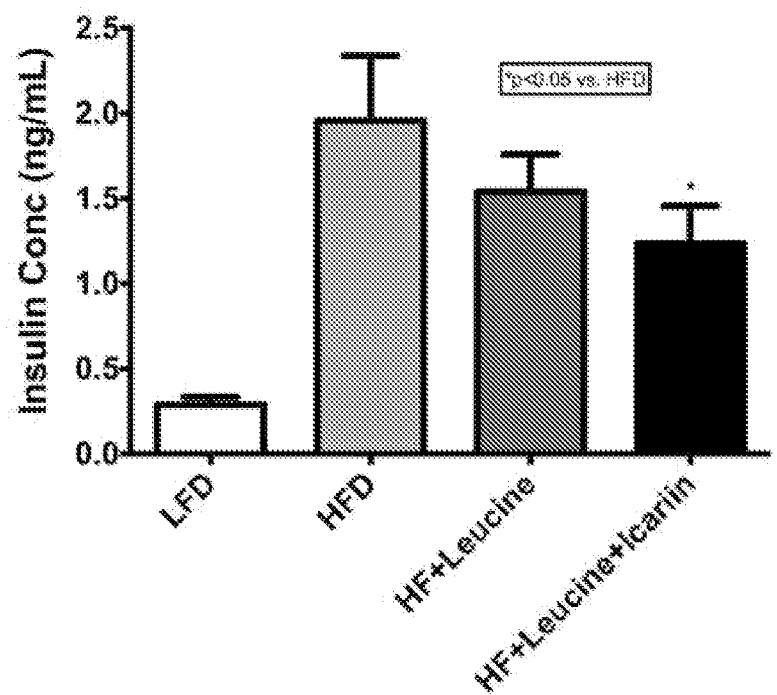
FIG. 24 shows fasting insulin levels following 6 weeks of treatment with leucine or leucine+icariin in high fat diet mice, as compared to untreated low fat diet mice.
Figure 25:
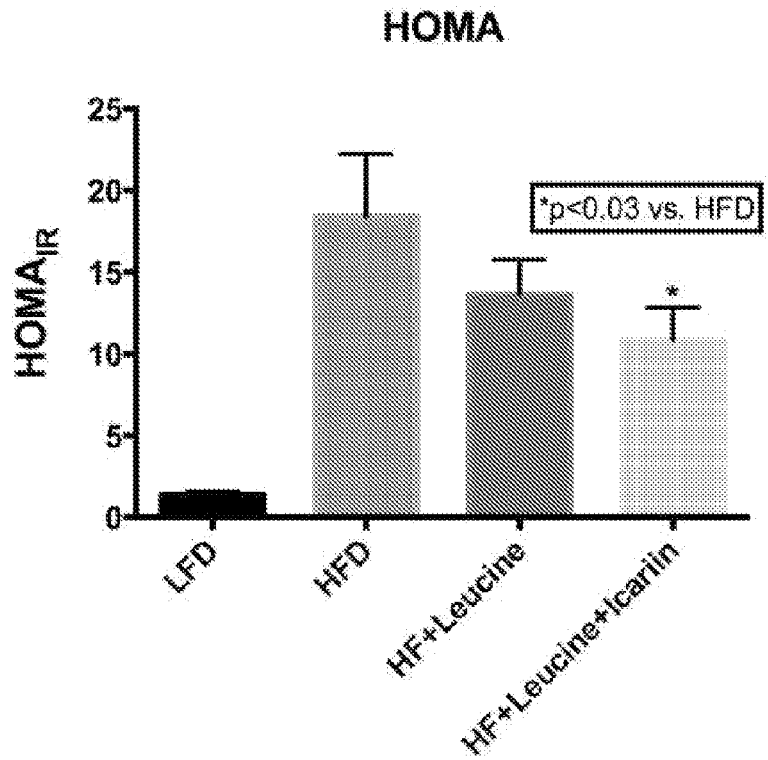
FIG. 25 shows Homeostatic Assessment of Insulin Resistance following 6 weeks of treatment with leucine or leucine+icariin in high fat diet mice, as compared to untreated low fat diet mice.
Figure 26:
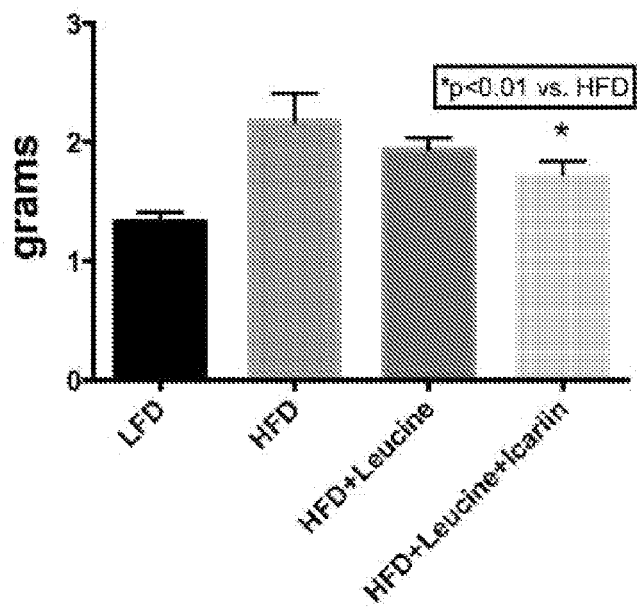
FIG. 26 shows liver mass following 6 weeks of treatment with leucine or leucine+icariin in high fat diet mice, as compared to untreated low fat diet mice.
Figure 27:
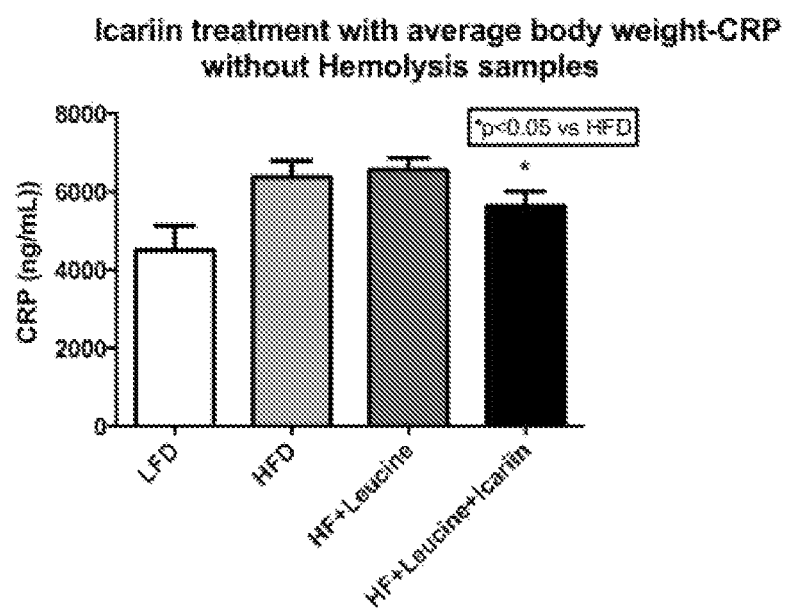
FIG. 27 shows levels of the inflammatory marker C-reactive protein following 6 weeks of treatment with leucine or leucine+icariin in high fat diet mice, as compared to untreated low fat diet mice.

Glucose tolerance was assessed in all experimental groups after five weeks of treatment. FIG. 21 depicts results from the glucose tolerance test measured at five weeks of treatment and demonstrates significant reduction in the blood glucose response to the glucose challenge. Area under the curve (AUC) measures were performed on the glucose concentration curves of FIG. 21 to obtain a measure of integrated glucose response to glucose load over time. AUC was increased by ~75% as compared to LFD mice (p<0.01, FIG. 22). Treatment of the HFD mice with leucine and icariin significantly decreased glucose load by about 40% as compared to untreated HFD mice (p<0.01 vs. HFD mice, FIG. 22).

At the end of the 6 week study, fasting blood glucose levels, insulin levels, $HOMA_{IR}$, liver mass, and circulating C-reactive protein (a biomarker of inflammation) were assessed in all experimental groups (FIG. 23-27). Assessment of fasting blood glucose at the end of the 6 week study revealed that HFD mice exhibited a ~1-fold increase in fasting glucose as compared to LFD mice (FIG. 23). 6 week treatment of the HFD mice with leucine alone reduced fasting glucose by ~20% as compared to untreated HFD mice (FIG. 23). 6 week treatment of the HFD mice with leucine+icariin reduced fasting glucose by about 40% as compared to untreated HFD mice (p=0.0014 vs. HFD, FIG. 23). Assessment of fasting insulin levels at the end of the 6 week study revealed that HFD mice exhibited an 8-fold increase in circulating insulin as compared to LFD mice (FIG. 24). 6 week treatment of the HFD mice with leucine alone reduced circulating insulin during fasting by ~25% as compared to untreated HFD mice (FIG. 24). 6 week treatment of the HFD mice with leucine+icariin reduced circulating insulin during fasting by about 40% as compared to untreated HFD mice (p<0.05 vs. HFD, FIG. 24). Assessment of $HOMA_{IR}$ at the end of the 6 week study revealed that HFD mice exhibited a ~10-fold increase in circulating insulin as compared to LFD mice (FIG. 25). 6 week treatment of the HFD mice with leucine alone reduced $HOMA_{IR}$ by ~30% as compared to untreated HFD mice (FIG. 25). 6 week treatment of the HFD mice with leucine+icariin reduced HOMA$_{IR}$ by about 45% as compared to untreated HFD mice (p<0.03 vs. HFD, FIG. 25). These results demonstrated that combined administration of a branched amino acid (e.g., free leucine) and a PDE5 inhibitor remain therapeutically effective against diabetes for a long term, without losing effectiveness even after 6 weeks of administration in mice. Taking into account the life expectancy of laboratory mice vs. life expectancy of an average human, this effectiveness in mice suggests that the combined administration of a branched amino acid (e.g., free leucine) and a PDE5 inhibitor can remain therapeutically effective (e.g., against diabetes) for four years or more.

A chronic high fat diet is associated with other deleterious consequences. For example, a chronic high fat diet can increase liver mass, likely resulting from fatty accumulation in the liver. Chronic high fat feeding is also associated with chronic inflammation, which can contribute to a number of diseases. To determine the effects of leucine or leucine+icariin administration on additional consequences of high fat feeding, liver mass and C-reactive protein (a biomarker of inflammation) were assessed in all experimental groups at the end of the 6 week study. Assessment of liver mass at the end of the 6 week study revealed that HFD mice exhibited a ~40% increase in liver mass as compared to LFD mice (p=0.01, FIG. 26). 6 week treatment of the HFD mice with leucine alone reduced liver mass by ~10% as compared to untreated HFD mice (FIG. 26). 6 week treatment of the HFD mice with leucine+icariin reduced liver mass by about 25% as compared to untreated HFD mice (p<0.01 vs. HFD, FIG. 26). Assessment of c-reactive protein at the end of the 6 week study revealed that HFD mice exhibited a ~30% increase in liver mass as compared to LFD mice (FIG. 27). 6 week treatment of the HFD mice with leucine+icariin reduced C-reactive protein levels by about 20% as compared to untreated HFD mice (p<0.05 vs. HFD, FIG. 27).

All together, these data demonstrate significant, robust improvements in fasting and post-prandial glucose, glucose tolerance and insulin sensitivity in response to a low dose of icariin in combination with leucine. These improvements are comparable to those of anti-diabetic pharmaceuticals in this animal model, indicating the therapeutic potential of this combination. Moreover, this combination resulted in a significant improvement in liver mass and the inflammatory biomarker c-reactive protein.

It should be understood from the foregoing that, while particular implementations have been illustrated and described, various modifications can be made thereto and are contemplated herein. It is also not intended that the invention be limited by the specific examples provided within the specification. While the invention has been described with reference to the aforementioned specification, the descriptions and illustrations of the preferable embodiments herein are not meant to be construed in a limiting sense. Furthermore, it shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art. It is therefore contemplated that the invention shall also cover any such modifications, variations and equivalents.

What is claimed is:

1. A composition comprising:
    (a) a synergistically effective amount of a phosphodiesterase 5 (PDE 5) inhibitor; and
    (b) at least 500 mg of leucine and/or at least 200 mg of a leucine metabolite, wherein the PDE 5 inhibitor comprises sildenafil.

2. The composition of claim 1, wherein the amount of phosphodiesterase 5 (PDE 5) inhibitor is a sub-therapeutic amount.

3. The composition of claim 1, wherein the composition is formulated as a unit dosage.

4. The composition of claim 3, wherein the unit dosage comprises a sub-therapeutic amount of component (a) that is between 0.1 and 20 mg of sildenafil.

5. The composition of claim 3, wherein the unit dosage comprises a sub-therapeutic amount of component (a) that is between 0.1 and 10 mg of sildenafil.

6. The composition of claim 2, wherein the sub-therapeutic amount of component (a) further comprises between 0.5-50 mg of avanafil, 0.05-10 mg of iodenafil, 0.25-25 mg of mirodenafil, 0.01-1.25 mg of tadalafil, 0.01-1.25 mg of vardenafil, 0.5-50 mg of udenafil, 0.5-50 mg of zaprinst, or 0.05-100 mg of icariin.

7. The composition of claim 1, wherein the component (b) is free leucine.

8. The composition of claim 1, wherein the component (b) comprises between 500 to 2000 mg of free leucine.

9. The composition of claim 1, wherein the component (b) comprises at least 200 mg of a leucine metabolite comprising beta-hydroxymethylbutyrate (HMB).

10. The composition of claim 1, further comprising an anti-diabetic agent.

11. The composition of claim 1, further comprising a sub-therapeutic amount of an anti-diabetic agent.

12. The composition of claim 10, wherein the anti-diabetic agent is a biguanide or thiazoladinedione.

13. The composition of claim 10, wherein the anti-diabetic agent is metformin or rosiglitazone.

14. The composition of claim 10, wherein the anti-diabetic agent comprises at least 25 mg of metformin.

15. The composition of claim 1, further comprising resveratrol.

16. The composition of claim 10, wherein component (a) comprises between 0.1 and 10 mg of sildenafil, component (b) comprises between 500 and 2000 mg of free leucine, and the anti-diabetic agent comprises at least 250 mg of metformin.

17. The composition of claim 1, further comprising a pharmaceutically active agent other than the PDE 5 inhibitor and the leucine and/or the leucine metabolite.

18. The composition of claim 1, wherein the composition further comprises less than 1% by weight of an amino acid selected from the group consisting of alanine, arginine, asparagine, aspartic acid, cysteine, glutamic acid, glutamine, glycine, histidine, isoleucine, lysine, methionine, phenylalanine, proline, serine, threonine, tryptophan, tyrosine, and valine in free amino acid form.

19. The composition of claim 1, wherein the composition further comprises less than 1% by weight of isoleucine and valine.

20. The composition of claim 1, wherein the composition is free of isoleucine and valine.

21. The composition of claim 1, wherein the composition is formulated in tablets or capsules.

* * * * *